(12) United States Patent
Hibner et al.

(10) Patent No.: US 8,911,381 B2
(45) Date of Patent: *Dec. 16, 2014

(54) BIOPSY DEVICE WITH TRANSLATING VALVE MEMBER

(75) Inventors: John A. Hibner, Mason, OH (US);
Andrew T. Beckman, Cincinnati, OH (US); Lee Reichel, Springboro, OH (US); Chris W. Cicenas, Columbus, OH (US); Luke C. Stonis, Columbus, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 271 days.

This patent is subject to a terminal disclaimer.

(21) Appl. No.: 13/490,613

(22) Filed: Jun. 7, 2012

(65) Prior Publication Data

US 2012/0245485 A1  Sep. 27, 2012

Related U.S. Application Data

(63) Continuation of application No. 12/959,506, filed on Dec. 3, 2010, now Pat. No. 8,235,913, which is a continuation of application No. 11/198,558, filed on Aug. 5, 2005, now Pat. No. 7,867,173.

(51) Int. Cl.
*A61B 10/00* (2006.01)
*A61B 10/02* (2006.01)
*A61B 17/00* (2006.01)

(52) U.S. Cl.
CPC ..... *A61B 10/0266* (2013.01); *A61B 2017/0046* (2013.01); *A61B 10/0275* (2013.01); *A61B 10/0283* (2013.01); *A61B 2010/0225* (2013.01)
USPC .......................................................... 600/568

(58) Field of Classification Search
USPC ................................... 600/562–567; 604/160
See application file for complete search history.

(56) References Cited

U.S. PATENT DOCUMENTS

| 2,853,071 A | 9/1958 | Saffir |
| 3,630,192 A | 12/1971 | Jamshidi |

(Continued)

FOREIGN PATENT DOCUMENTS

| EP | 0890339 | 1/1999 |
| EP | 0 995 400 | 4/2000 |

(Continued)

OTHER PUBLICATIONS

U.S. Appl. No. 60/869,736, filed Dec. 13, 2006, Hibner.

(Continued)

*Primary Examiner* — Brian Szmal
(74) *Attorney, Agent, or Firm* — Frost Brown Todd LLC

(57) ABSTRACT

A biopsy device includes a needle extending distally from a body. The needle includes a transverse aperture, a first lumen, and a second lumen. A cutter is movable within the first lumen to sever tissue protruding through the transverse aperture. A valve assembly is operable to change the pneumatic state of the second lumen. The valve assembly includes a valve body and a translating member slidably disposed in a bore of the valve body. The valve body includes a first port and a second port. The first port is in fluid communication with the second lumen of the needle. The second port is in fluid communication with atmospheric air. The translating member selectively couples the first port with the second port based on the longitudinal position of the translating member within the bore. The translating member translates relative to the valve body based on the position of the cutter.

20 Claims, 44 Drawing Sheets

(56) References Cited

U.S. PATENT DOCUMENTS

| | | |
|---|---|---|
| 3,719,086 A | 3/1973 | Bannister et al. |
| 3,994,297 A | 11/1976 | Kopf |
| 4,051,852 A | 10/1977 | Villari |
| 4,600,014 A | 7/1986 | Beraha |
| 4,782,833 A | 11/1988 | Einhorn |
| 5,234,000 A | 8/1993 | Hakky et al. |
| 5,406,959 A | 4/1995 | Mann |
| 5,439,457 A | 8/1995 | Yoon |
| 5,526,822 A | 6/1996 | Burbank et al. |
| 5,532,168 A | 7/1996 | Marantz |
| 5,601,585 A | 2/1997 | Banik et al. |
| 5,645,209 A | 7/1997 | Green et al. |
| 5,649,547 A | 7/1997 | Ritchart et al. |
| 5,769,086 A | 6/1998 | Ritchart et al. |
| 5,775,333 A | 7/1998 | Burbank et al. |
| 5,873,967 A | 2/1999 | Clark et al. |
| 5,876,329 A | 3/1999 | Harhen |
| 5,928,164 A | 7/1999 | Burbank et al. |
| 5,964,716 A | 10/1999 | Gregoire et al. |
| 5,980,469 A | 11/1999 | Burbank et al. |
| 6,007,230 A | 12/1999 | Beckett et al. |
| 6,017,316 A | 1/2000 | Ritchart et al. |
| 6,042,593 A | 3/2000 | Storz et al. |
| 6,077,230 A | 6/2000 | Gregoire et al. |
| 6,083,177 A | 7/2000 | Kobren et al. |
| 6,086,544 A | 7/2000 | Hibner et al. |
| 6,120,462 A | 9/2000 | Hibner et al. |
| 6,142,946 A | 11/2000 | Hwang et al. |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,402,701 B1 | 6/2002 | Kaplan et al. |
| 6,409,970 B1 | 6/2002 | Phifer |
| 6,428,486 B2 | 8/2002 | Ritchart et al. |
| 6,436,054 B1 | 8/2002 | Viola et al. |
| 6,485,436 B1 | 11/2002 | Truckai et al. |
| 6,488,636 B2 | 12/2002 | Bryan et al. |
| 6,544,194 B1 | 4/2003 | Kortenbach |
| 6,620,111 B2 | 9/2003 | Stephens et al. |
| 6,626,849 B2 | 9/2003 | Huitema et al. |
| 6,638,235 B2 | 10/2003 | Miller et al. |
| 6,659,338 B1 | 12/2003 | Dittmann et al. |
| 6,758,824 B1 | 7/2004 | Miller |
| 6,849,080 B2 | 2/2005 | Lee et al. |
| 6,986,748 B2 | 1/2006 | McAlister et al. |
| 7,025,098 B2 | 4/2006 | Osborne |
| 7,025,732 B2 | 4/2006 | Thompson et al. |
| 7,185,681 B2 | 3/2007 | Romano |
| 7,189,206 B2 | 3/2007 | Quick et al. |
| 7,204,811 B2 | 4/2007 | Kortenbach et al. |
| 7,226,424 B2 | 6/2007 | Ritchart |
| 7,252,641 B2 | 8/2007 | Thompson et al. |
| 7,276,032 B2 | 10/2007 | Hibner |
| 7,278,991 B2 | 10/2007 | Morris et al. |
| 7,419,472 B2 | 9/2008 | Hibner et al. |
| 7,442,171 B2 | 10/2008 | Stephens et al. |
| 7,445,739 B2 | 11/2008 | Tsonton et al. |
| 7,470,237 B2 | 12/2008 | Beckman et al. |
| 7,497,833 B2 | 3/2009 | Miller |
| 7,556,622 B2 | 7/2009 | Mark et al. |
| 7,575,556 B2 | 8/2009 | Speeg et al. |
| 7,662,109 B2 | 2/2010 | Hibner |
| 7,740,594 B2 | 6/2010 | Hibner |
| 7,740,596 B2 | 6/2010 | Hibner |
| 7,749,172 B2 | 7/2010 | Schwindt |
| 7,753,857 B2 | 7/2010 | Hibner |
| 7,758,515 B2 | 7/2010 | Hibner |
| 7,819,819 B2 | 10/2010 | Quick et al. |
| 7,828,745 B2 | 11/2010 | McAlister et al. |
| 7,854,706 B2 | 12/2010 | Hibner |
| 7,854,707 B2 | 12/2010 | Hibner et al. |
| 7,867,173 B2 | 1/2011 | Hibner et al. |
| 7,896,817 B2 | 3/2011 | Garrison |
| 7,985,239 B2 | 7/2011 | Suzuki |
| 8,002,713 B2 | 8/2011 | Heske et al. |
| 8,016,772 B2 | 9/2011 | Heske et al. |
| 8,038,627 B2 | 10/2011 | Hibner |
| 8,118,755 B2 | 2/2012 | Hibner et al. |
| 8,177,728 B2 | 5/2012 | Hibner et al. |
| 8,177,729 B2 | 5/2012 | Hibner et al. |
| 8,235,913 B2 | 8/2012 | Hibner et al. |
| 8,241,226 B2 | 8/2012 | Hibner et al. |
| 8,262,586 B2 | 9/2012 | Almazan et al. |
| 2002/0076355 A1 | 6/2002 | Phifer |
| 2002/0082518 A1 | 6/2002 | Weiss et al. |
| 2002/0120212 A1 | 8/2002 | Ritchart et al. |
| 2003/0125639 A1 | 7/2003 | Fisher et al. |
| 2003/0199753 A1 | 10/2003 | Hibner et al. |
| 2004/0153003 A1 | 8/2004 | Cicenas et al. |
| 2005/0049521 A1 | 3/2005 | Miller et al. |
| 2005/0065453 A1 | 3/2005 | Shabaz et al. |
| 2005/0165328 A1 | 7/2005 | Heske et al. |
| 2005/0215921 A1 | 9/2005 | Hibner et al. |
| 2005/0215922 A1 | 9/2005 | Tsonton et al. |
| 2006/0041230 A1 | 2/2006 | Davis |
| 2006/0074344 A1 | 4/2006 | Hibner |
| 2006/0074345 A1 | 4/2006 | Hibner |
| 2006/0258955 A1 | 11/2006 | Hoffman et al. |
| 2007/0032741 A1 | 2/2007 | Hibner et al. |
| 2007/0032742 A1 | 2/2007 | Monson |
| 2007/0032743 A1 | 2/2007 | Hibner |
| 2007/0112751 A1 | 5/2007 | Pyun |
| 2007/0213630 A1 | 9/2007 | Beckman et al. |
| 2007/0239067 A1 | 10/2007 | Hibner et al. |
| 2008/0004545 A1 | 1/2008 | Garrison |
| 2008/0082021 A1 | 4/2008 | Ichikawa et al. |
| 2008/0195066 A1 | 8/2008 | Speeg et al. |
| 2008/0214955 A1 | 9/2008 | Speeg et al. |
| 2010/0075664 A1 | 3/2010 | Maucksch |
| 2010/0106053 A1 | 4/2010 | Videbaek et al. |
| 2010/0152610 A1 | 6/2010 | Parihar et al. |
| 2010/0160816 A1 | 6/2010 | Parihar et al. |
| 2010/0160819 A1 | 6/2010 | Parihar et al. |
| 2010/0160824 A1 | 6/2010 | Parihar et al. |
| 2010/0317997 A1 | 12/2010 | Hibner et al. |

FOREIGN PATENT DOCUMENTS

| | | |
|---|---|---|
| EP | 1 520 518 | 4/2005 |
| EP | 1 642 533 | 4/2006 |
| EP | 1 832 234 | 12/2007 |
| EP | 1 932 482 | 6/2008 |
| GB | 2 018 601 | 10/1979 |
| RU | 2021770 | 10/1994 |
| WO | WO 03/077768 | 9/2003 |
| WO | WO 2004/016177 | 2/2004 |
| WO | WO 2004/052179 | 6/2004 |
| WO | WO 2004/052212 | 6/2004 |
| WO | WO 2004/075728 | 9/2004 |
| WO | WO 2006/005342 | 1/2006 |
| WO | WO 2006/124489 | 11/2006 |
| WO | WO 2007/019152 | 2/2007 |
| WO | WO 2007/021904 | 2/2007 |
| WO | WO 2007/112751 | 10/2007 |

OTHER PUBLICATIONS

U.S. Appl. No. 60/874,792, filed Dec. 13, 2006, Hibner.
European Search Report dated Jun. 13, 2007 for Application No. 07250402.
European Search Report dated Nov. 14, 2007 for Application No. 07250926.
European Search Report dated Dec. 11, 2007 for PCT Application No. 07253220.
European Search Report dated Dec. 20, 2007 for EPO Application No. 07253220.
European Examination Report dated May 13, 2008 for Application No. EP 07250402.
European Examination Report dated Mar. 19, 2009 for Application No. 07250926.
European Search Report dated Apr. 3, 2009 for Application No. 08252518.

(56) References Cited

OTHER PUBLICATIONS

European Search Report dated Apr. 3, 2009 for Application No. 08252524.
European Search Report dated Sep. 29, 2010 for Application No. EP 10251076.
Supplemental European Search Report dated Dec. 16, 2009 for Application No. EP06789155.
Patentability Report and Written Opinion dated Feb. 5, 2008 for Application No. PCT/US2006/030022.
International Search Report dated Jul. 18, 2007 for Application No. PCT/US 06/30022.
International Search Report dated Sep. 27, 2007 for Application No. PCT/US06/30022.
International Search Report dated Dec. 18, 2008 for Application No. PCT/US2008/058627.
Written Opinion dated Apr. 26, 2010 for Application No. EP 08252524.
Non-final Rejection dated Mar. 20, 2008 for U.S. Appl. No. 11/782,963.
Non-final Rejection dated Apr. 4, 2008 for U.S. Appl. No. 11/736,117.
Final Rejection dated Sep. 26, 2008 for U.S. Appl. No. 11/782,963.
Non-Final Rejection dated Oct. 6, 2008 for U.S. Appl. No. 11/736,117.
EnCor MRI Specifications and Breast Biopsy System, SenoRx, 2005, pp. 102.
European Search Report dated Dec. 1, 2005 for Application No. EP 05256035.
European Communication dated Jun. 25, 2007 for Application No. EP 05256035.
European Search Report dated Apr. 5, 2012 for Application No. EP 11193357.

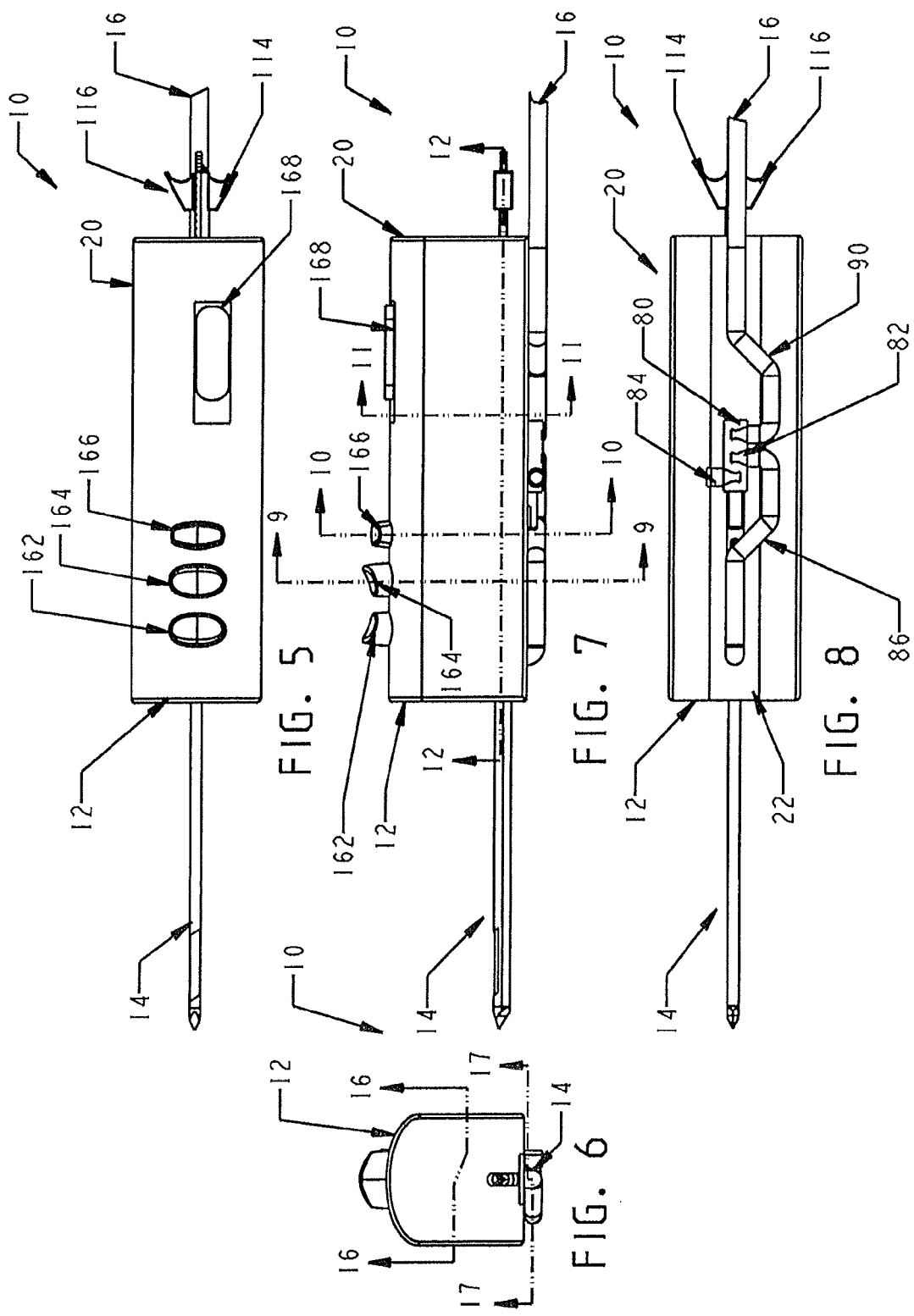

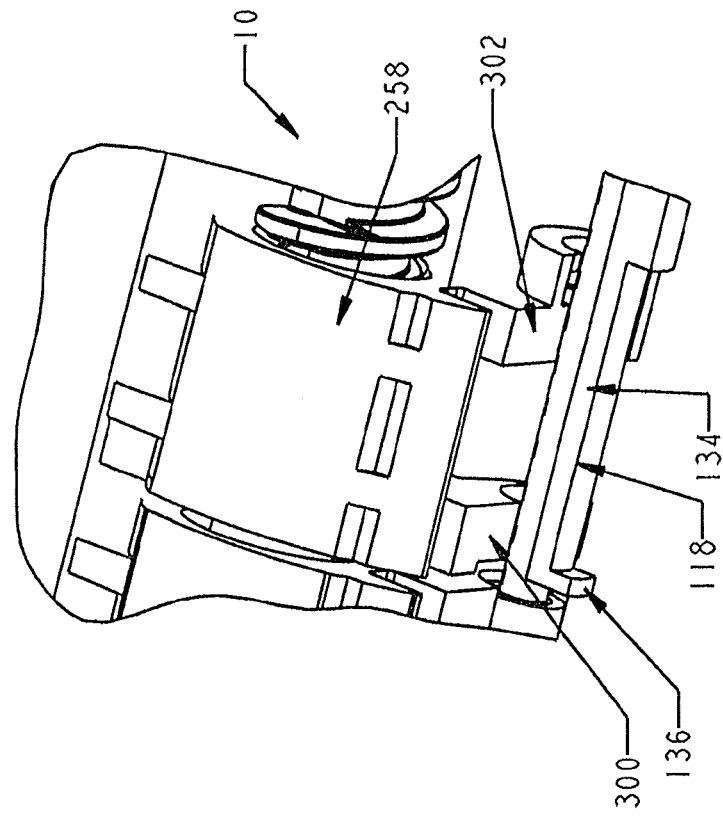
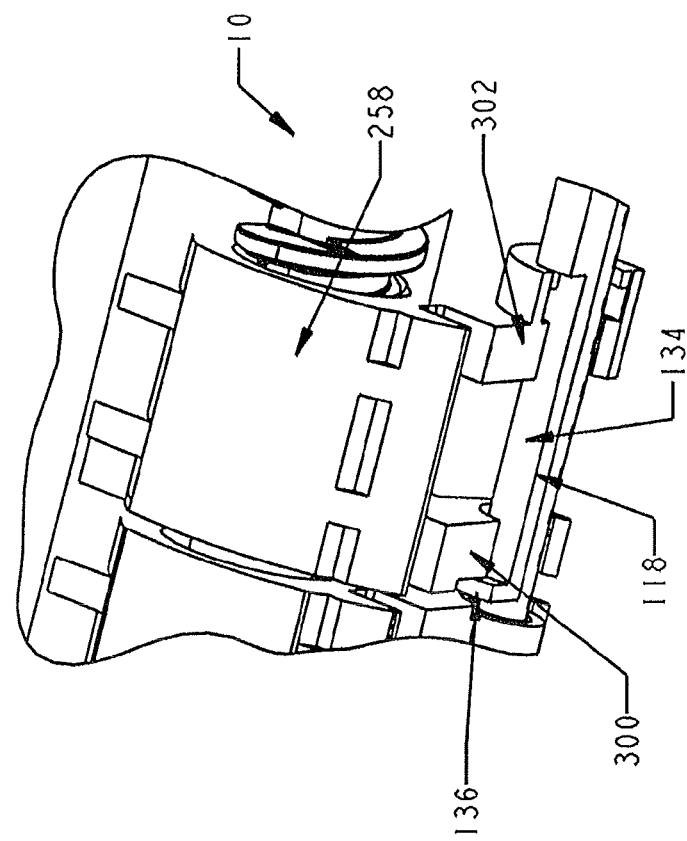

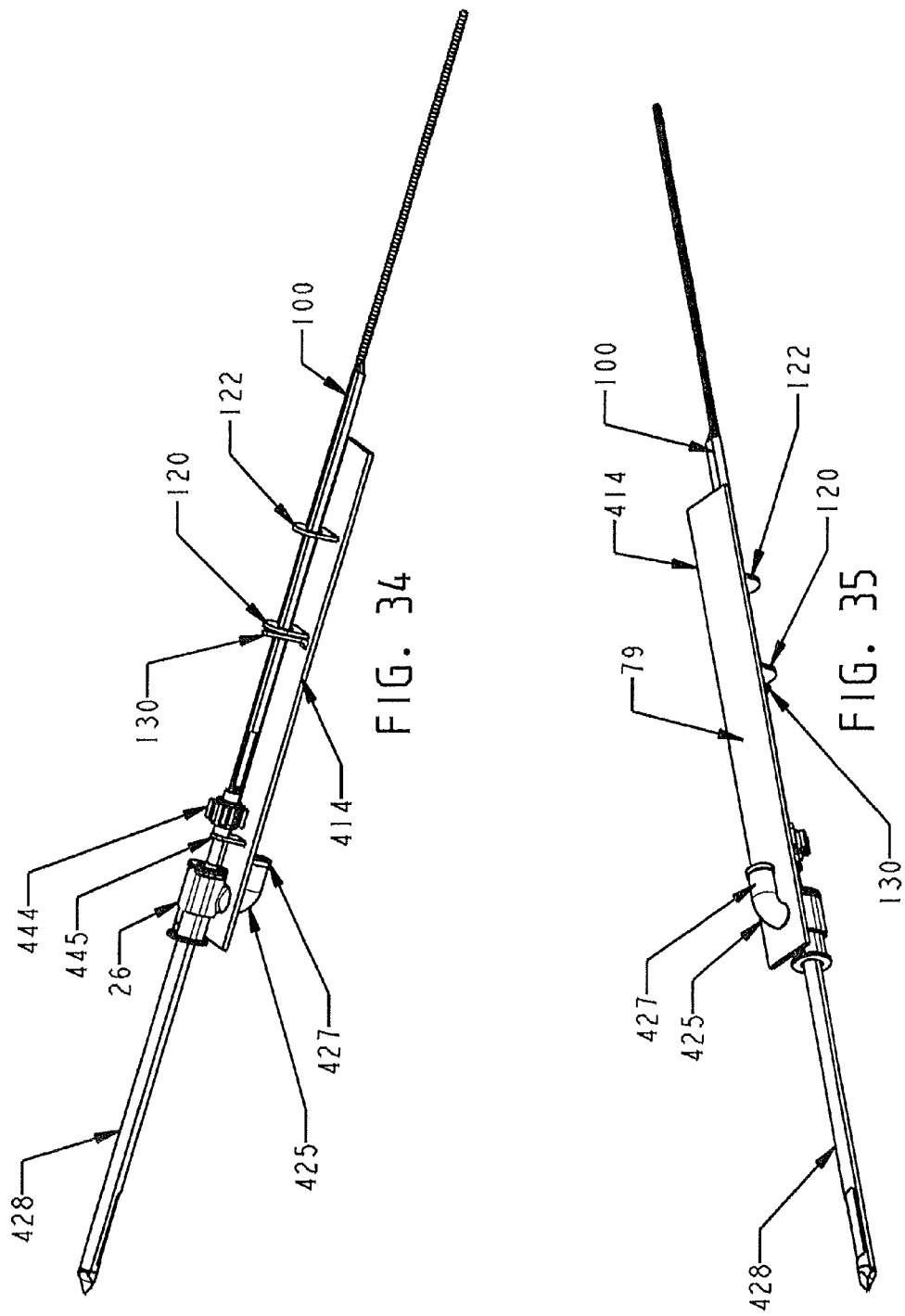

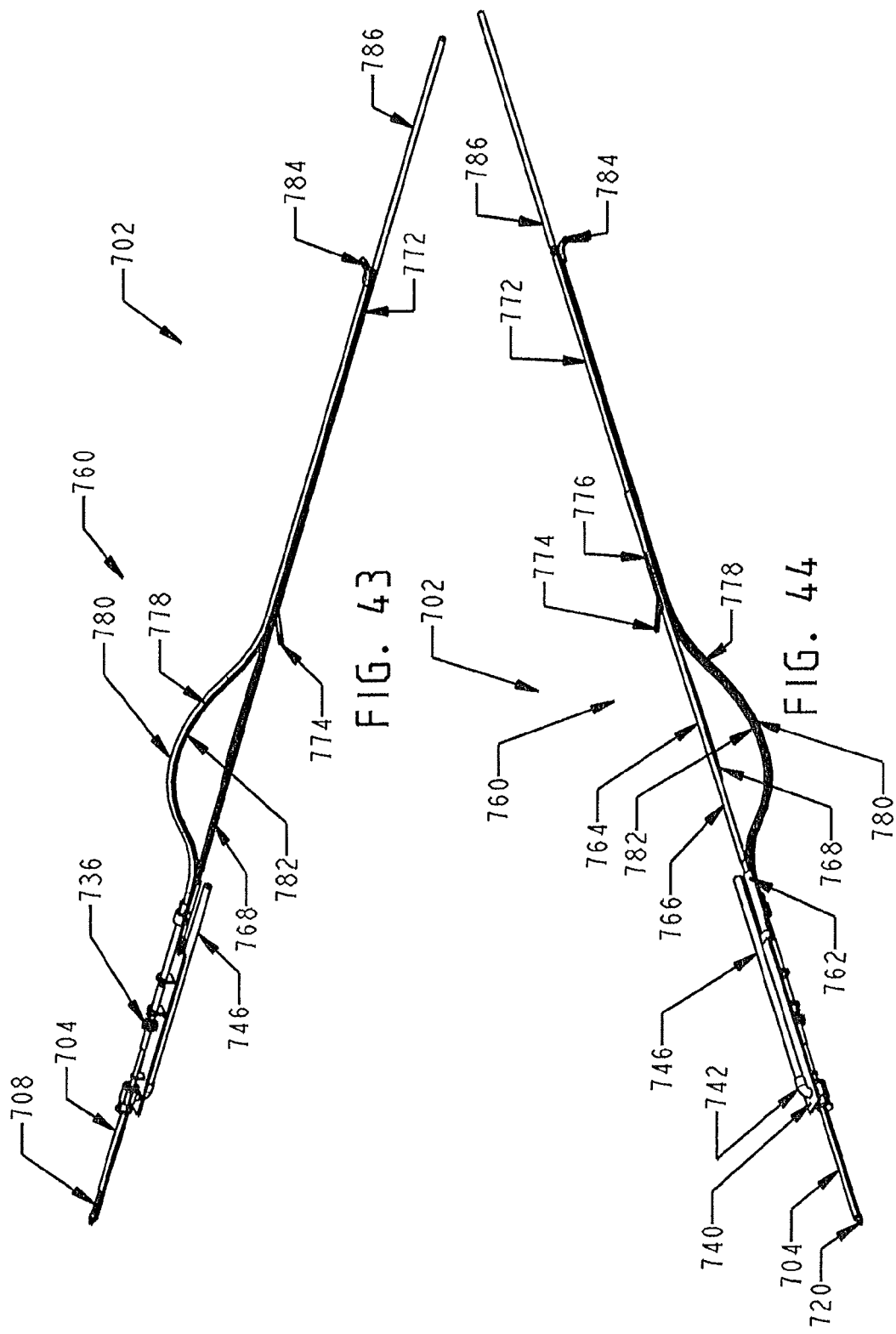

BIOPSY DEVICE WITH TRANSLATING VALVE MEMBER

PRIORITY

This application is a continuation of U.S. patent application Ser. No. 12/959,506, entitled "Biopsy Device With Translating Valve Member," filed Dec. 3, 2010, which is a continuation of U.S. patent application Ser. No. 11/198,558, entitled "Biopsy Device with Replaceable Probe and Incorporating Vibration Insertion Assist and Static Vacuum Source Sample Stacking Retrieval," filed Aug. 5, 2005, the disclosures of which are incorporated by reference herein.

FIELD OF THE INVENTION

The present invention relates in general to biopsy devices, and more particularly to biopsy devices having a cutter for severing tissue, and even more particularly to biopsy devices for multiple sampling with a probe remaining inserted.

BACKGROUND OF THE INVENTION

When a suspicious tissue mass is discovered in a patient's breast through examination, ultrasound, MRI, X-ray imaging or the like, it is often necessary to perform a biopsy procedure to remove one or more samples of that tissue in order to determine whether the mass contains cancerous cells. A biopsy may be performed using an open or percutaneous method.

An open biopsy is performed by making a large incision in the breast and removing either the entire mass, called an excisional biopsy, or a substantial portion of it, known as an incisional biopsy. An open biopsy is a surgical procedure that is usually done as an outpatient procedure in a hospital or a surgical center, involving both high cost and a high level of trauma to the patient. Open biopsy carries a relatively higher risk of infection and bleeding than does percutaneous biopsy, and the disfigurement that sometimes results from an open biopsy may make it difficult to read future mammograms. Further, the aesthetic considerations of the patient make open biopsy even less appealing due to the risk of disfigurement. Given that a high percentage of biopsies show that the suspicious tissue mass is not cancerous, the downsides of the open biopsy procedure render this method inappropriate in many cases.

Percutaneous biopsy, to the contrary, is much less invasive than open biopsy. Percutaneous biopsy may be performed using fine needle aspiration (FNA) or core needle biopsy. In FNA, a very thin needle is used to withdraw fluid and cells from the suspicious tissue mass. This method has an advantage in that it is very low-pain, so low-pain that local anesthetic is not always used because the application of it may be more painful than the FNA itself. However, a shortcoming of FNA is that only a small number of cells are obtained through the procedure, rendering it relatively less useful in analyzing the suspicious tissue and making an assessment of the progression of the cancer less simple if the sample is found to be malignant.

During a core needle biopsy, a small tissue sample is removed allowing for a pathological assessment of the tissue, including an assessment of the progression of any cancerous cells that are found. The following patent documents disclose various core biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; and US Patent Application 2003/0199753 published Oct. 23, 2003 to Hibner et al.

At present, a biopsy instrument marketed under the tradename MAMMOTOME is commercially available from ETHICON ENDO-SURGERY, INC. for use in obtaining breast biopsy samples. These devices generally retrieve multiple core biopsy samples from one insertion into breast tissue with vacuum assistance. In particular, a cutter tube is extended into a probe to cut tissue prolapsed into a side aperture under vacuum assistance and then the cutter tube is fully retracted between cuts to extract the sample.

With a long probe, the rate of sample taking is limited not only by the time required to rotate or reposition the probe but also by the time needed to translate the cutter. As an alternative to this "long stroke" biopsy device, a "short stroke" biopsy device is described in the following commonly assigned patent applications: U.S. patent application Ser. No. 10/676,944, "Biopsy Instrument with Internal Specimen Collection Mechanism" filed Sep. 30, 2003 in the name of Hibner et al.; and U.S. patent application Ser. No. 10/732,843, "Biopsy Device with Sample Tube" filed Dec. 10, 2003 in the name of Cicenas et al. The cutter is cycled across the side aperture, reducing the sample time. Several alternative specimen collection mechanisms are described that draw samples through the cutter tube, all of which allow for taking multiple samples without removing the probe from the breast.

Even given the many advantages of such multiple sample taking core biopsy devices, in certain applications some surgeons continue to use less expensive biopsy devices guided in real time by an ultrasonic system. These simple biopsy systems omit a full function control console that operates the cutter and vacuum assistance. Instead, a manually controlled hand piece advances a cutter by either stored spring force, a constant pneumatic pressure source, or motor power. Then the surgeon activates a cutter motor to effect the tissue sample. Thus, the surgeon is challenged to maintain the biopsy probe at a desired surgical site while manipulating the patient's breast.

Consequently, it would be desirable to provide for a core biopsy device with a motorized cutter that provides increased functionality such as one-handed operation with assisted multiple sample retrieval with only one insertion of the probe, yet be able to retain the economical aspects of simple core biopsy devices that lack elaborate remote control systems.

Spring-fired core needle biopsy devices rely upon a firing mechanism that thrusts forward a needle and a cutter to penetrate the tissue and to obtain a tissue sample rather than palpitating tissue to prolapse into a side aperture of a probe. Frequently, a surgeon may encounter an area of dense tissue that is more difficult to penetrate than the surrounding tissue during core needle biopsy. In particular, the lesion or tissue mass being targeted in the biopsy procedure may be difficult to penetrate, requiring the physician to push the biopsy needle with considerable force and/or speed in an attempt to penetrate the lesion and collect a sample.

When encountering such an area of dense tissue, it is common for surgeons using the type of firing core needle biopsy device described above to fire the device in order to penetrate the lesion and obtain a sample. However, due to the length of the firing stroke of such devices, which may be as long as 0.75 inches, it is nearly impossible for the surgeon to control the travel of the needle after firing. Consequently, the long needle stroke may cause uncertainty as to the needle tip location post fire. This may cause the surgeon to obtain a sample from the wrong area. In addition to missing the targeted tissue, long firing strokes may cause the needle to puncture the chest wall or pierce the skin, particularly when the targeted area is near the patient's chest wall. Even if the skin is not pierced, the long travel of the needle, along with the likelihood that the needle will be pushed off course by the force of the firing stroke, may lead to needlessly increased trauma for the patient. These spring-fired biopsy devices also yield a single sample per insertion, thus limiting the amount of diagnostic and therapeutic treatment that may be achieved without the increased discomfort and tissue trauma from repeated insertions. Based on surgeons' use of the long firing stroke feature of current devices to aid in penetrating tissue lesions, it is clear that the medical community sees the benefit of firing assistance when inserting a probe to the desired location.

In commonly-owned and co-pending U.S. patent application Ser. No. 11/035,873, BIOPSY INSTRUMENT WITH IMPROVED NEEDLE PENETRATION to Beckman, et al., filed on Jan. 10, 2005, manual mechanisms are disclosed that impart small reciprocating motions to the probe of a core biopsy device to render assistance in penetrating tissue, yet cutting is performed after the probe is properly positioned, thus avoiding taking samples from the wrong location. While there are advantages to having such cutting assistance imparted by manual actuation, it is generally desirable to alleviate the need for the surgeon to perform this additional action while having to manually position the biopsy device.

Additionally, it would be desirable to provide for a handheld core biopsy device that automatically imparts a motion to the probe that assists in penetrating dense tissue yet does not take a sample.

SUMMARY OF THE INVENTION

The present invention addresses these and other problems of the prior art by providing a core biopsy device having a probe assembly with a probe support structure that holds a probe having a side aperture. A cutter tube is slidingly received by the probe and sized to translate across the side aperture to sever prolapsed tissue. A hand piece includes a hand piece support structure having a lateral engaging portion that receives the probe assembly. A lead screw is attached for rotation to the hand piece support structure. A cutter carriage is longitudinally translated by rotation of the lead screw thereby translating the cutter tube. Thereby, an economical incorporation of a replaceable probe and cutter tube into a laterally mounted assembly allows reuse of a powered hand piece.

In one aspect consistent with other aspects of the invention, a biopsy device includes a frame supported core biopsy probe, the frame spring biased to a housing. A motor driven cam wheel coupled to the housing urges the frame against the spring bias, imparting a reciprocating longitudinal movement to the core biopsy probe to assist in penetrating dense tissue.

In another aspect of the invention, a biopsy device includes the replaceable probe assembly that engages a motor-driven carriage assembly that sequences distal translation of a rotated cutter tube with vacuum assistance sequenced from a constant vacuum source by the position of the cutter tube. Thereby, advantages of consistent prolapse of tissue into the probe is achieved with a commonly available vacuum source.

In yet another aspect of the invention, a biopsy device obtains tissue samples that prolapse into a sample aperture in a probe needle that are then severed by a translating cutter tube received in the probe needle. A sample straw is proximally received in the cutter tube to capture these severed tissue samples. As these severed tissue samples are sequentially stacked in the sample straw, an indicator tube is forced proximally out of the sample straw to give a visual indication as to the number of tissue samples obtained. The stored tissue samples advantageously are maintained in the order taken, which aids in further diagnostic assessment.

In yet a further aspect of the invention, a biopsy device obtains tissue samples that prolapse into a sample aperture in a probe needle that are then severed by a translating cutter tube received in the probe needle. A storage tube communicates with a proximal end of the cutter tube so that a vacuum control may apply a vacuum through the storage tube and the cutter tube to retract severed tissue samples there through. The stored tissue samples are also advantageously maintained in the order taken to aid in further diagnostic assessment.

In yet an additional aspect of the invention, a hand piece has a hand piece support structure having a lateral engaging portion operatively configured to engage a probe support structure of a selected one of a first and second probe assemblies. A lead screw translates a cutter carriage that advances a cutter tube within a probe needle of the selected probe assembly. One probe assembly includes a sample straw that is proximally advanced by a cutter carriage of the hand piece that is longitudinally translated by rotation of the lead screw to retract tissue samples. The other probe assembly has a storage tube that communicates with the cutter tube for pneumatically retracting tissue samples. Thereby, economical incorporation of a common hand piece may be realized while providing the clinical flexibility of choosing a disposable probe assembly with a desired approach to tissue sample retraction.

In yet another aspect of the invention, a method of obtaining core biopsy samples advantageously maintains samples taken in a sequential stack to enhance diagnostic assessment thereof. This orientation is achieved by inserting a core biopsy needle into tissue, prolapsing tissue into an opening of the core biopsy needle and then translating a cutter tube through the core biopsy needle to sever the prolapsed tissue to form a first tissue sample. These steps are repeated with each tissue sample being sequentially urged into a sample lumen that proximally communicates with the cutter tube. Thereby, the sequential stacking is maintained for lateral retrieval and analysis.

These and other objects and advantages of the present invention shall be made apparent from the accompanying drawings and the description thereof.

BRIEF DESCRIPTION OF THE DRAWINGS

While the specification concludes with claims particularly pointing out and distinctly claiming the present invention, it is believed the same will be better understood by reference to the following description, taken in conjunction with the accompanying drawings in which:

FIG. 5 is a top view of an assembled biopsy device of FIG. 1;

FIG. 6 is a front view of the biopsy device of FIG. 5;

FIG. 7 is a left side view in elevation of the biopsy device of FIG. 5;

FIG. 8 is a bottom view of the biopsy device of FIG. 5;

FIG. 29 is a perspective view of the straw carriage and an engaged stacking straw assembly;

FIG. 30 is a perspective view of the straw carriage and a disengaged stacking straw assembly;

FIG. 34 is a top perspective view of an alternative probe assembly with omitted vacuum assistance instead relying on external hand palpitation of tissue to prolapse the tissue into the side aperture of the probe for the biopsy device of FIG. 1 to acquire tissue samples;

FIG. 35 is a bottom perspective view of the alternative probe assembly of FIG. 34;

FIG. 43 is a top left perspective view of the alternative proximal stacking disposable assembly of FIG. 40 with a retrieved tissue sample and a retracted cutter;

FIG. 44 is a bottom right perspective view of the alternative proximal stacking disposable assembly of FIG. 43;

DETAILED DESCRIPTION OF THE INVENTION

Figure 1:
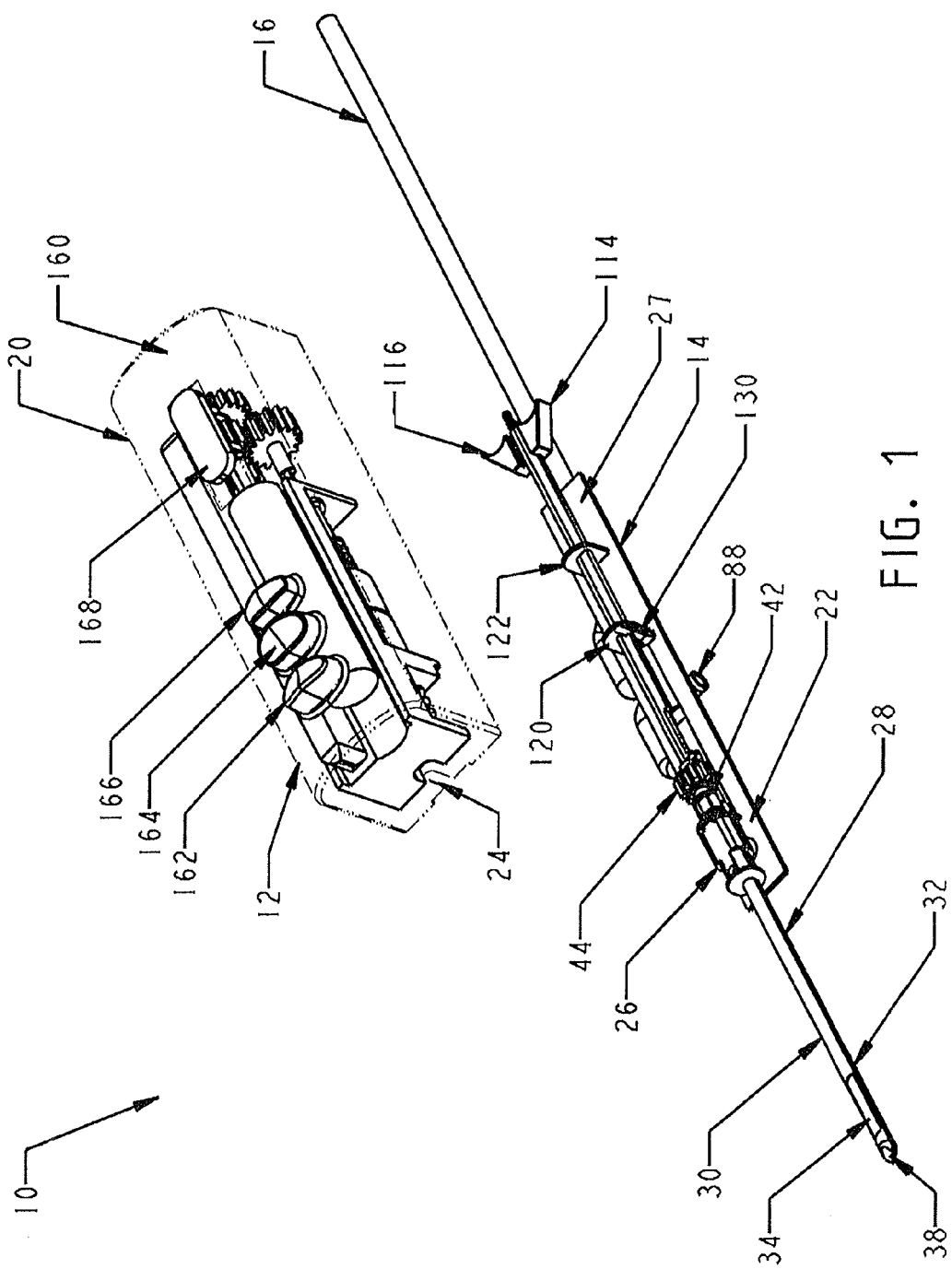
FIG. 1 is a top perspective view of a biopsy device with a disposable probe assembly detached from a reusable hand piece, the latter with a housing shown in phantom.

In FIGS. 1-4, a biopsy device 10 has a reusable hand piece 12 and a disposable probe 14 that enables economical taking of multiple percutaneous core biopsy samples by accessing a standard medical vacuum pump or wall-mounted vacuum access port (not shown) through an interfacing vacuum conduit 16. In the illustrative version, the hand piece 12 is self-powered and suitable for use in conjunction with ultrasonic diagnostic imaging. The disposable probe 14 reduces the portion of biopsy device 10 that requires protective packaging to avoid contact with sharp surfaces and to keep it sterile prior to use. Further economy is accomplished by reducing the portion of the biopsy device 10 that is disposed as medical waste between uses. Movable components of the disposable probe 14 are advantageously locked until mounted in an access trough 18 formed in a housing 20 of the reusable hand piece 12. It should be appreciated that one or more standard mechanical, pneumatic, or electrical latches (not shown) may be integrated into the biopsy device 10 to secure the disposable probe 14 to the reusable hand piece 12.

Figure 2:
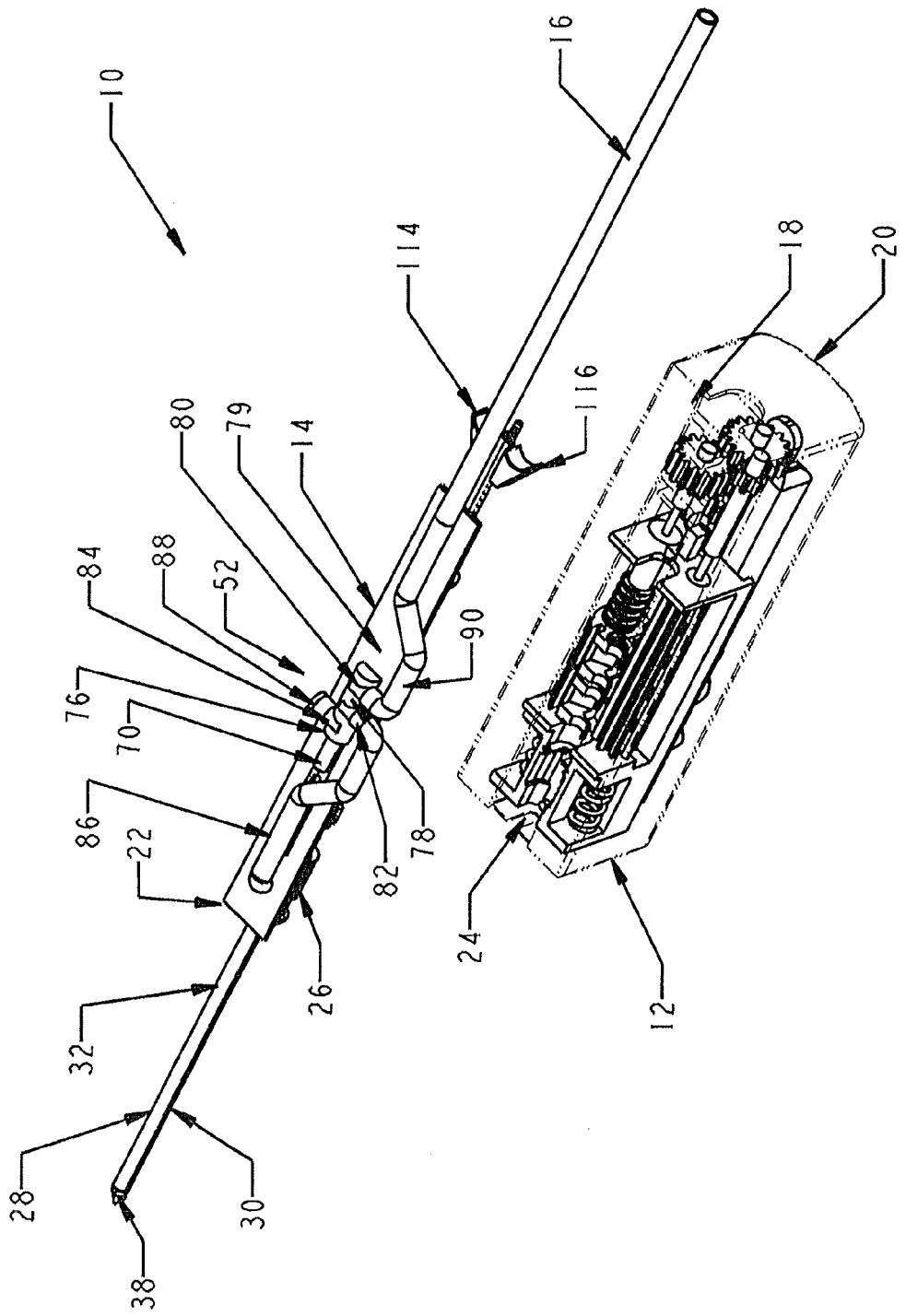
FIG. 2 is a bottom perspective view of the biopsy device of FIG. 1.
Figure 3:
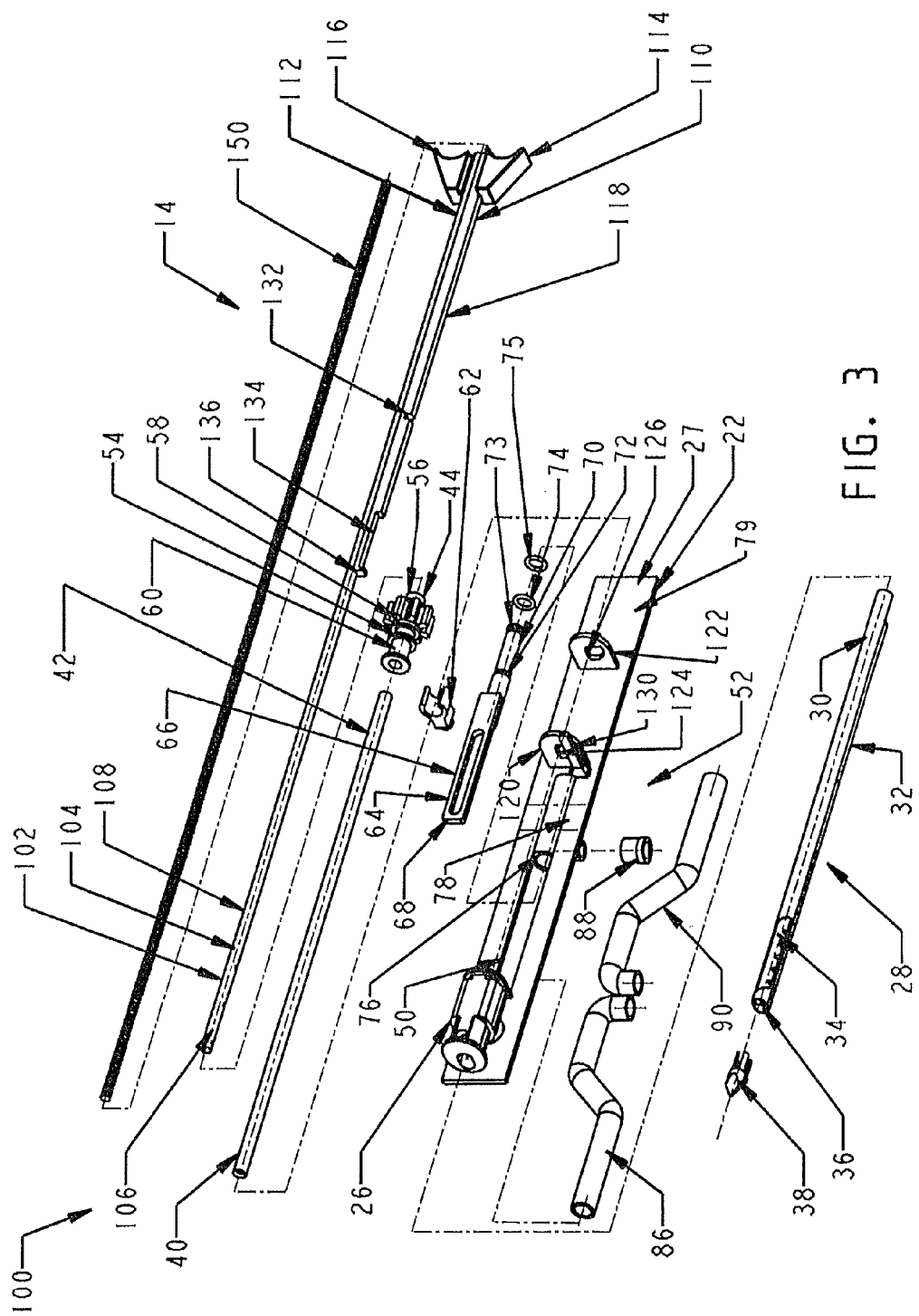
FIG. 3 is a disassembled perspective view of the disposable probe assembly of FIG. 1.
Figure 4:
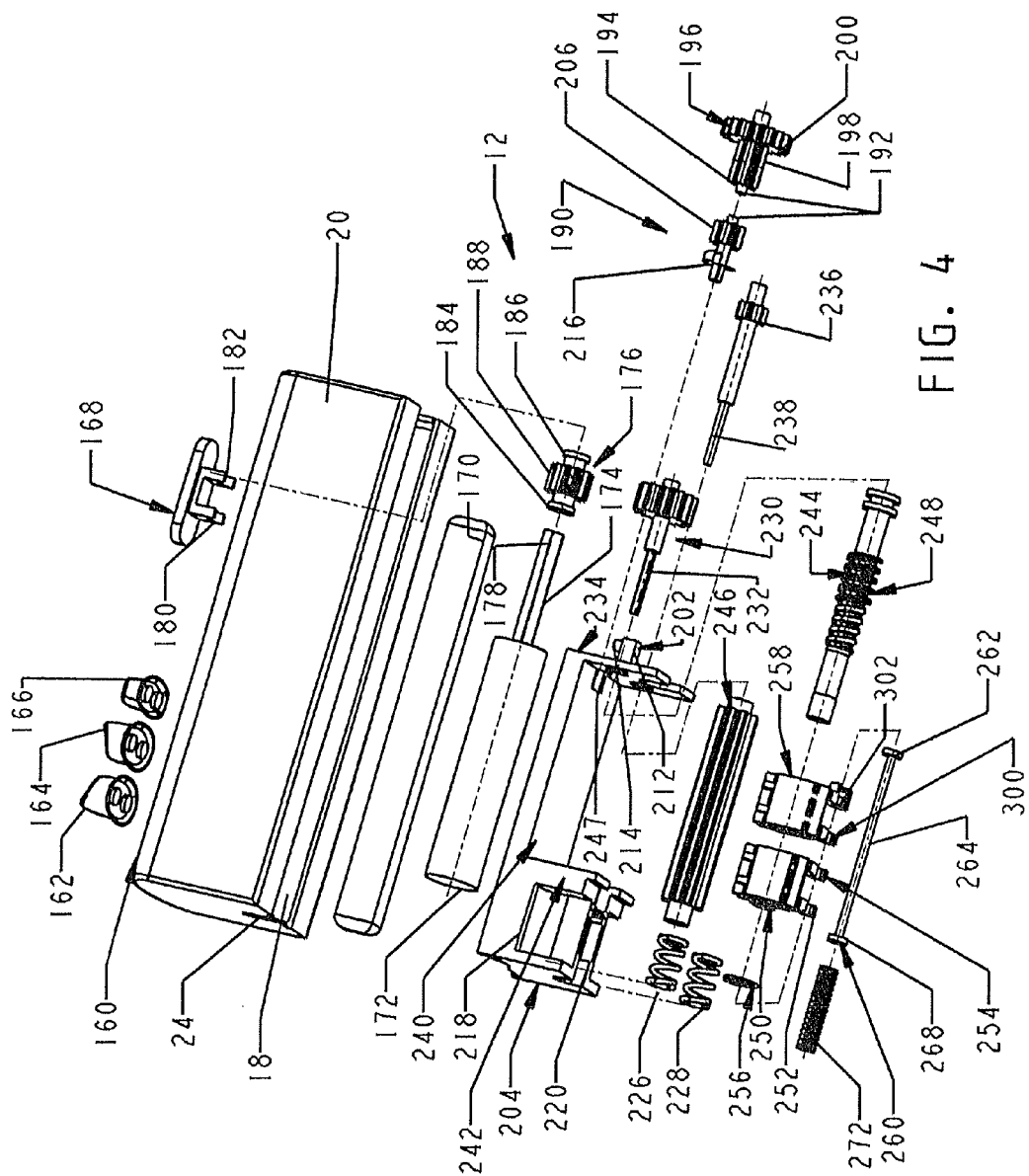
FIG. 4 is a disassembled perspective view of the reusable hand piece of FIG. 1.

With particular reference to FIG. 3, the disposable probe assembly 14 includes a substantially rectangular cover 22 sized to close the access trough recess 18 (FIGS. 2, 4). An end slot 24 formed in the cover 20 (FIGS. 1-2, 4) is closed by a probe union sleeve 26 attached to an inner surface 27 of the substantially rectangular cover 22. A core biopsy needle ("probe") assembly 28 passes longitudinally through the probe union sleeve 26 and is formed by a probe tube 30 with underlying vacuum lumen 32 that communicates with a side aperture 34 through holes 35 (FIG. 23) near a distal opening 36 of the probe tube 30 that is closed by a piercing tip 38. A cutter tube 40 is sized to closely fit and translate within an inner diameter (i.e., cutter lumen) of the probe tube 30 with a length sufficient to close the side aperture 34 with a proximal end 42 extending from the probe union sleeve 26 to attach to a cutter gear 44, as depicted in FIG. 1.

Proximal to the probe union sleeve 26 is an elongate slot 50 that is part of a vacuum assist valve assembly 52. The cutter gear 44 includes distal and proximal annular recesses 54, 56 flanking spur gear teeth 58 that engage the reusable hand piece 12 as described below. A more distal annular recess 60 is gripped by a post 62 that is engaged to longitudinally translate in an elongate post slot 64 of a distal portion 66 of a vacuum valve actuator 68. A cylindrical proximal portion 70 of the vacuum valve actuator 68 has distal and proximal O-ring grooves 72, 73 that respectively retain distal and proximal dynamic O-ring seals 74, 75 that move within a distally open cylindrical valve bore 76 of a valve body 78 molded onto an outer surface 79 of the substantially rectangular cover 22 (FIG. 2).

As described below, the vacuum valve actuator 68 selectively allows communication between a proximal port 80, a center port 82, and a distal port 84 (FIG. 2). In particular, with the cutter gear 44 retracted, the proximal and center ports 80, 82 are in communication. With the cutter gear translated distally, the center and distal ports 82, 84 communicate. The center port 82 is attached to a distal vacuum conduit 86 whose other end is connected through the rectangular cover 22 to the probe union sleeve 26. It should be appreciated that the probe union sleeve 26 includes pneumatic passages that communicate between a proximal end of the vacuum lumen 32 and the distal vacuum conduit 86. The distal port 84 is attached to a hose nib 88 that is exposed to atmospheric pressure. Hose nib 88 may include an air and/or saline filter. Alternatively, hose nib 88 may be connected to a positive pressure source (e.g., fluid pump) or a negative pressure source (e.g., vacuum pump, syringe) to aspirate fluids. Likewise, hose nib 88 may be used to lavage the tissue cavity with saline, pain medication, or bleeding control fluids. The proximal port 80 communicates through a proximal vacuum conduit 90 to the interfacing vacuum conduit 16.

With further reference to FIG. 3, a sample extraction feature is incorporated so that multiple samples may be made without the need to remove the probe assembly 28 from tissue nor even to full retract the cutter tube 40 to retract a tissue specimen to the reusable hand piece 12. In the illustrative version, this feature is accomplished with a stacking straw assembly 100. An elongate straw 102 is scored down its length on opposite sides by grooves 104 defining first and second straw halves 106, 108, whose respective proximal, outer surfaces 110, 112 are attached to triangular grips 114, 116, respectively. A locking strip 118 extends distally from one triangular grip 114 and is attached along a proximal portion of the first straw half 106.

Distal and proximal tabs 120, 122 extend from the inner surface 27 of the substantially rectangular cover 22, each having a respective through hole 124, 126 through which the stacking straw assembly 100 is inserted. The through holes 124, 126 are shaped to allow the locking strip 118 to rotate ninety (90) degrees. A bayonet locking member 130 also extends from the inner surface 27 of the substantially rectangular cover 22 just distal and laterally offset from the through hole 124 of the distal tab 120 to lock into an alignment locking slot 132 in the locking strip 118 when laterally rotated. The bayonet locking member 130 prevents axial movement of the stacking straw assembly 100. The cutter gear 44 and cutter tube 40 cannot move proximally due to contact with the stacking straw assembly 100 and cannot move distally due to contact with the probe union sleeve 26. By securing both the cutter gear 44 and the stacking straw assembly 100 in a full distal axial position, the disposable probe 14 is aligned to engage the components of the reusable hand piece 12 as described below. Distal to the alignment locking slot 132, a rectangular recess 134, formed in the locking strip 118, defines a distal-most locking finger 136 for engaging components of the reusable hand piece 12 that positions the stacking straw assembly 100 as described below. An indicator tube 150 has a stacked cone-shaped outer surface 152 (FIG. 14) that slides within the elongate straw 104 that in turn slides within the cutter tube 40.

With particular reference to FIG. 4, the reusable hand piece 12 includes four user controls aligned on a top surface 160 of the housing 20, specifically from most distal to most proximal: a forward motor rotation key 162, a reverse motor rotation key 164, a saline flush key 166 and a slide button 168 for selecting insertion mode or sample taking mode. The keys 162-166 control a control circuit 170, which may include integral power storage (e.g., batteries, fuel cell, etc.) for untethered use. The forward motor rotation key 162 causes a DC motor 172 to rotate its motor output shaft 174 in a forward rotation. A slide spur gear 176 includes an internal keyed engagement with a longitudinal key groove 178 on the motor output shaft 174 that allows longitudinal positioning by the slide button 168. In particular, fore and aft brackets 180, 182 of the slide button 168 engage distal and aft annular grooves 184, 186 that flank spur gear teeth 188 of the slide spur gear 176.

Figure 13:
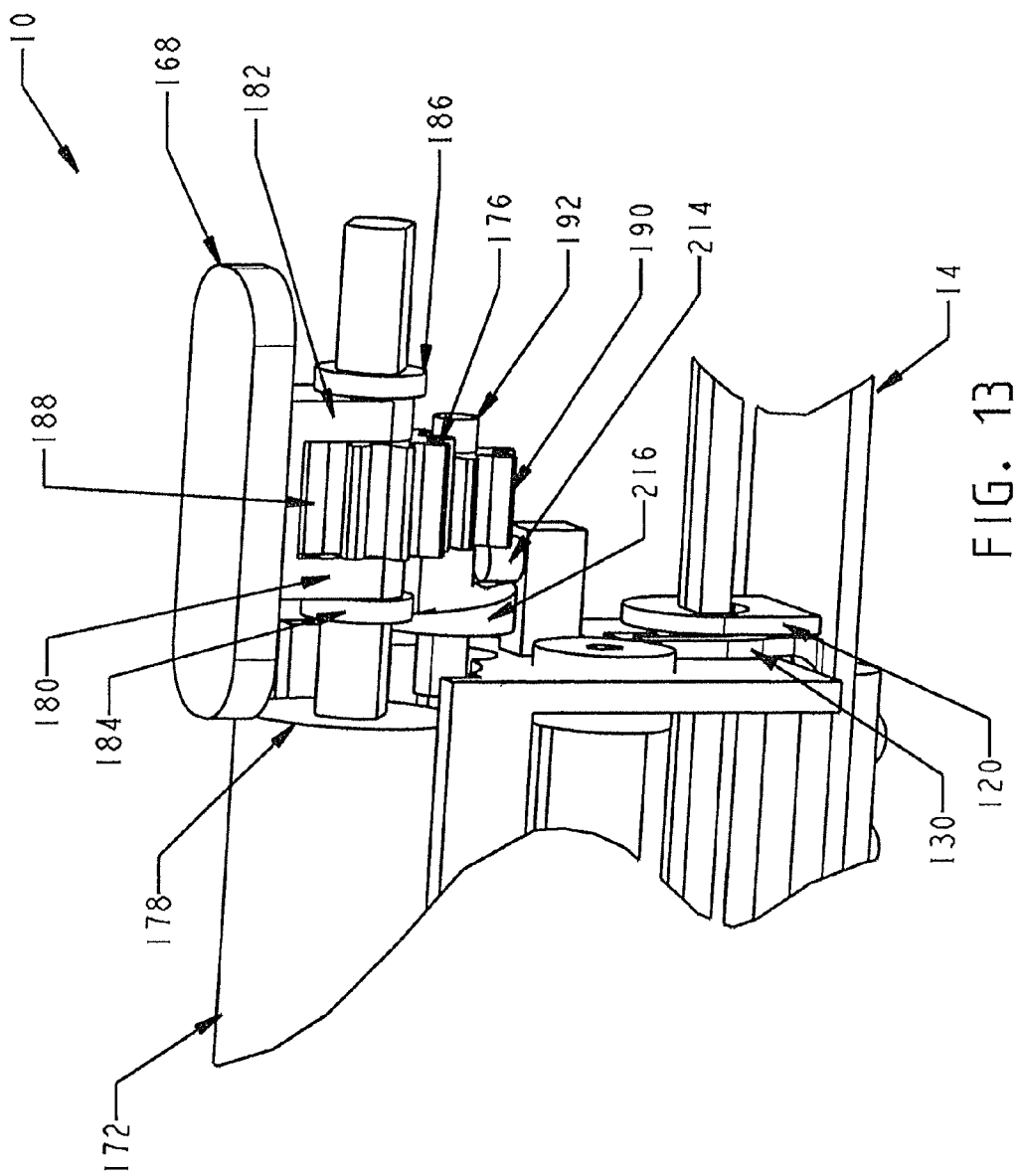
FIG. 13 is a detail perspective view of a slide button, sliding spur gear, and tissue penetration gear of the biopsy device of FIG. 5.

When the slide button 168 is moved distally, the slide spur gear 176 engages a tissue penetration gear 190 that spins on a common shaft centerline 192 forward of a gearbox input gear 196. Gearbox input gear 196 consists of a distal small gear 198 and a proximal large gear 200. The tissue penetration gear 190 has spur gear teeth 206 that engage the slide spur gear 176. A frame hub 212 projects proximally from the frame 204 with a strike pin 214 projecting upwardly from the frame hub 212. In FIGS. 4 and 13, a circular cam wheel 216 is attached to a distal side of the tissue penetration gear 190. Rotating the tissue penetration gear 190 urges the strike pin 214, and thus the frame 204, proximally. In FIG. 2, left and right spring cavities 218, 220 (when viewed from above), formed longitudinally in distal corners of the frame 204, respectively receive inwardly projecting left and right tabs 222, 224 from the cover 20 and receive left and right compression springs 226, 228. Movement of the frame 204 proximally compresses these compression springs 226, 228 that thereafter assert a restoring force.

When the slide button 168 is moved proximally into engagement with the gearbox input gear 196, specifically the distal small gear 198, also engages and turns a translation large input gear 230 whose shaft 232 passes through an aft wall 234 of the frame 204. The proximal large gear 200 of the gearbox input gear 196 engages and turns a rotation small input gear 236 whose shaft 238 passes through the aft wall 234. The frame 204 includes a carriage recess 240, defined between a partition 242 and the aft wall 234, that contains longitudinally aligned left side lead (translation) screw 244 and right-side rotation spur gear 246 that are attached for rotation respectively with the shafts 232, 238. The partition 242 is positioned aft of the left and right tabs 222, 224 of the cover 20 and also defines in part the left and right spring cavities 218, 220. An unlocking cam 247 projects proximally from and is longitudinally centered on the aft wall 234 above the position of the lead (translation) screw 244 and rotation spur gear 246.

Figure 19:
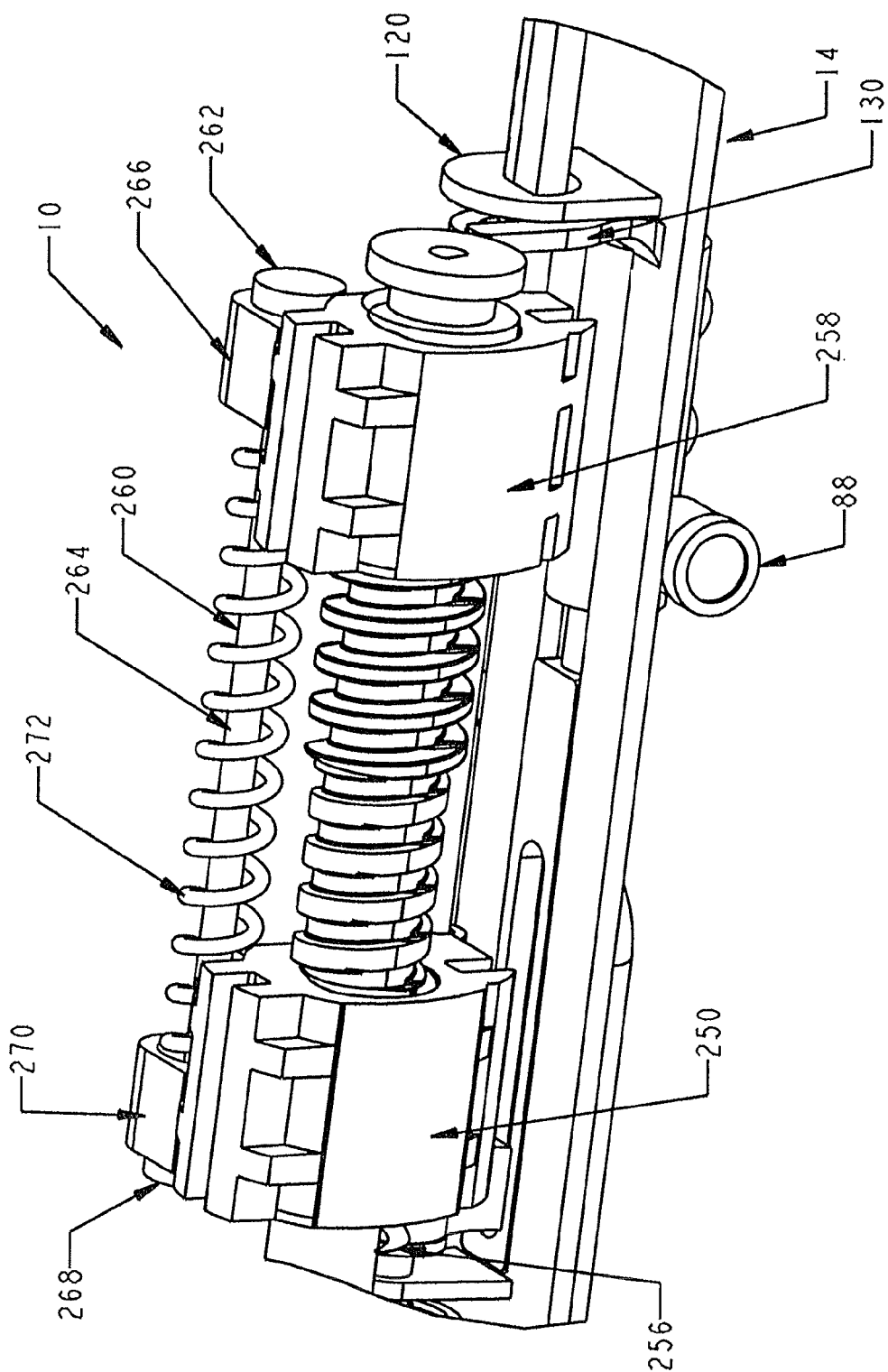
FIG. 19 is a left perspective detail view of the carriages, lead screw, and sliding pin of the biopsy device of FIG. 18 with the housing removed.

The rotation spur gear 246 engages the cutter gear 44 when the disposable probe 14 is inserted, imparting a rotation as the cutter tube 40 and cutter gear 44 translate longitudinally in response to the rotation of the lead (translation) screw 244. This translation is caused by lead screw threads 248. In particular, a distal cutter carriage 250 is longitudinally moved on the lead screw threads 248. Distal and proximal J-hook extensions 252, 254 project downwardly from the distal cutter carriage 250 to engage the distal and proximal annular recesses 54, 56 of the cutter gear 44 (FIG. 3). Distal of the cutter carriage 250, a biasing spring 256 urges against the cutter carriage 250, which assists in engagement of the lead screw threads 248 with the distal cutter carriage 250. With reference to FIGS. 4 and 19, a sliding pin 260 has a proximal carriage sliding pin retainer 266 attached to a proximal straw carriage 258. Shaft 264 also passes through a distal carriage sliding pin retainer 270 attached to the distal cutter carriage 250. Sliding pin 260 has a proximal end 262 and a distal end 268 to prevent the sliding pin 260 from disengaging from the carriage sliding pin retainers 266, 270. A sliding pin spring 272 resides on the sliding pin 260 and is constrained at each end by carriage sliding pin retainers 266, 270.

Figure 11:
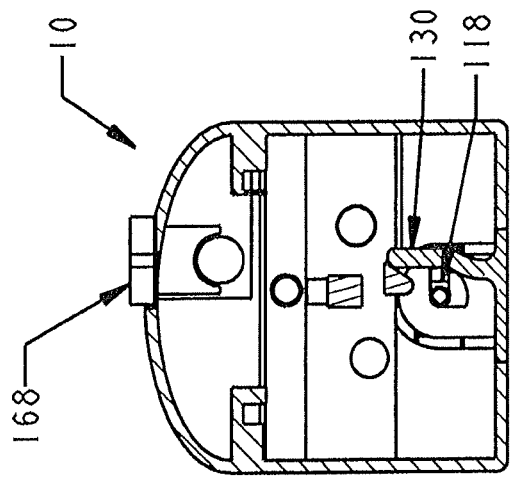
FIG. 11 is a front view of the biopsy device of FIG. 7 taken in cross section along lines 11-11 through a bayonet locking member disengaged from the stacking straw assembly by attaching the disposable probe assembly to the reusable hand piece.
Figure 10:
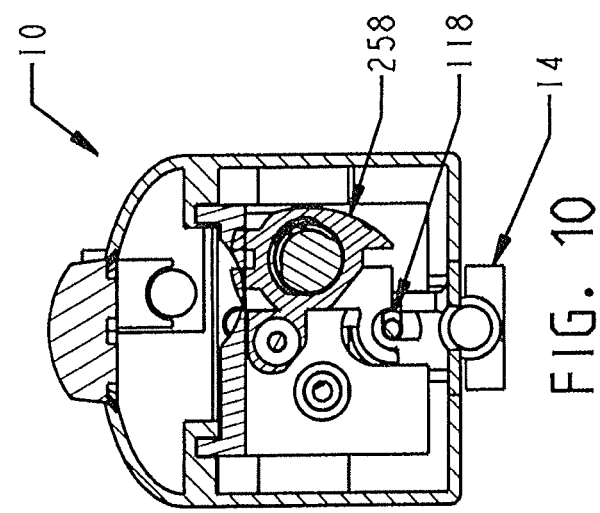
FIG. 10 is a front view of the biopsy device of FIG. 7 taken in cross section along lines 10-10 through a proximal straw carriage and stacking straw assembly.
Figure 9:
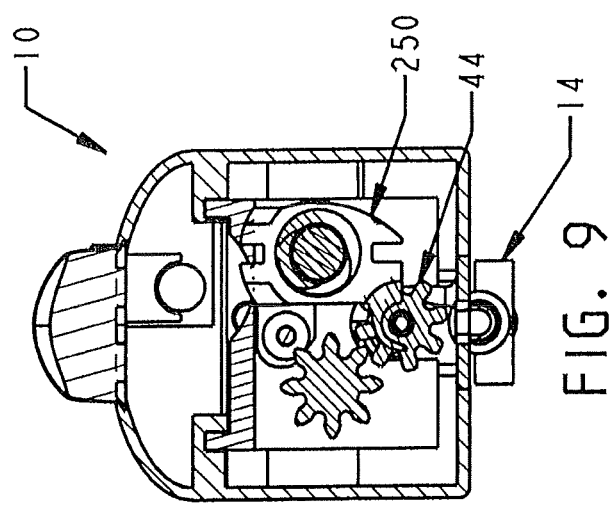
FIG. 9 is a front view of the biopsy device of FIG. 7 taken in cross section along lines 9-9 through a distal cutter carriage engagement to a cutter gear.

With the components FIGS. 1-4 now introduced, a sequence of use of the biopsy device 10 will be described. The interfacing vacuum lumen 16 is attached to the disposable probe assembly 14 (FIGS. 1-2). The disposable probe assembly 14 is installed into the reusable hand piece 12 (FIGS. 5-8). In so doing, the distal cutter carriage 250 engages the cutter gear 44 (FIG. 9), the proximal straw carriage 258 engages the locking strip 118 of the stacking straw assembly 100 (FIG. 10), and the bayonet locking member 130 is deflected by the unlocking cam 247, longitudinally unlocking from the alignment locking slot 132 of the locking strip 118 (FIG. 11) allowing longitudinal movement of the cutter tube 40 and the straw stacking assembly 100.

Figure 12:
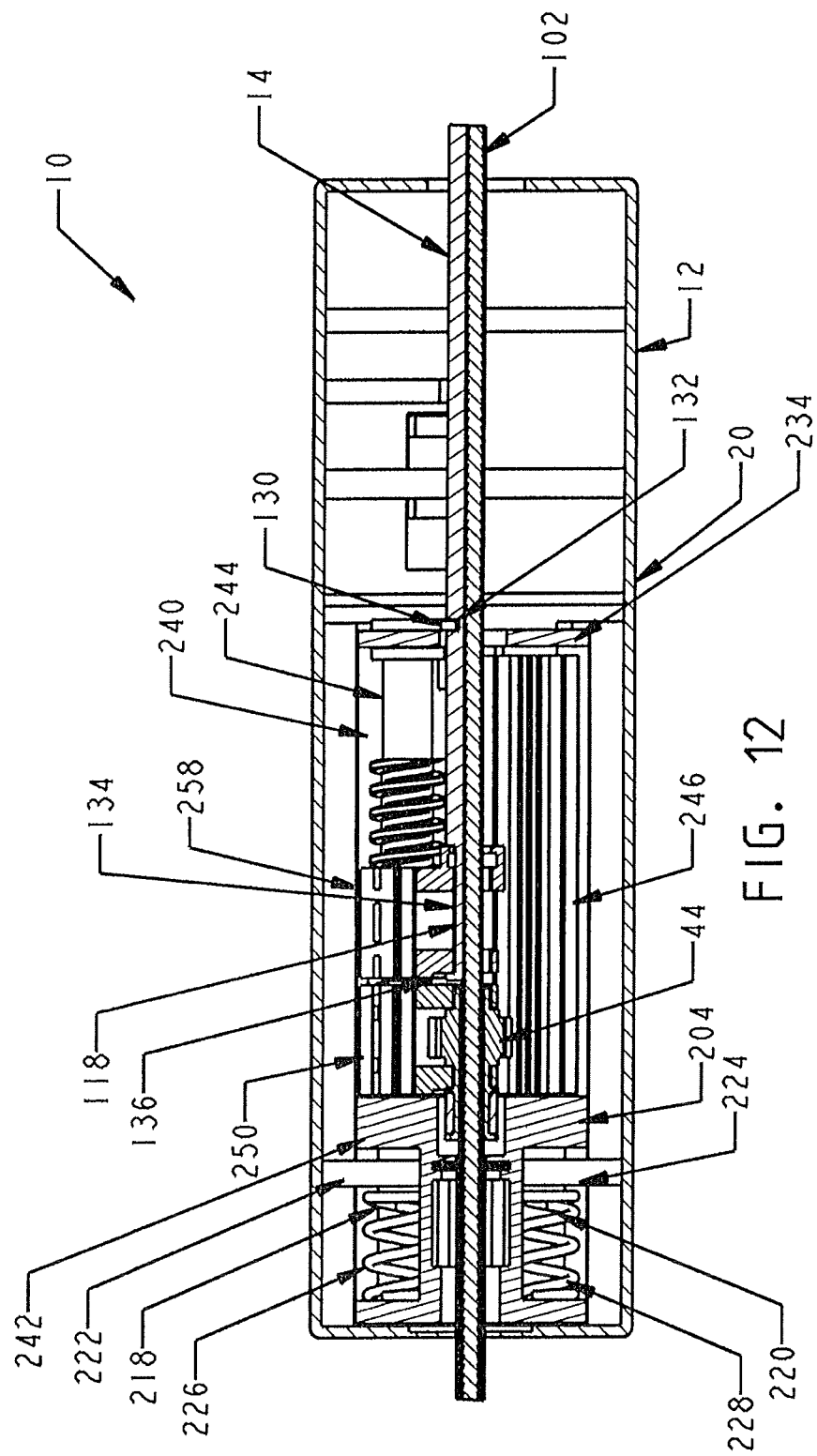
FIG. 12 is a bottom view of the biopsy device of FIG. 7 taken in horizontal cross section along lines 12-12 through the probe and stacking straw assembly.
Figure 14:
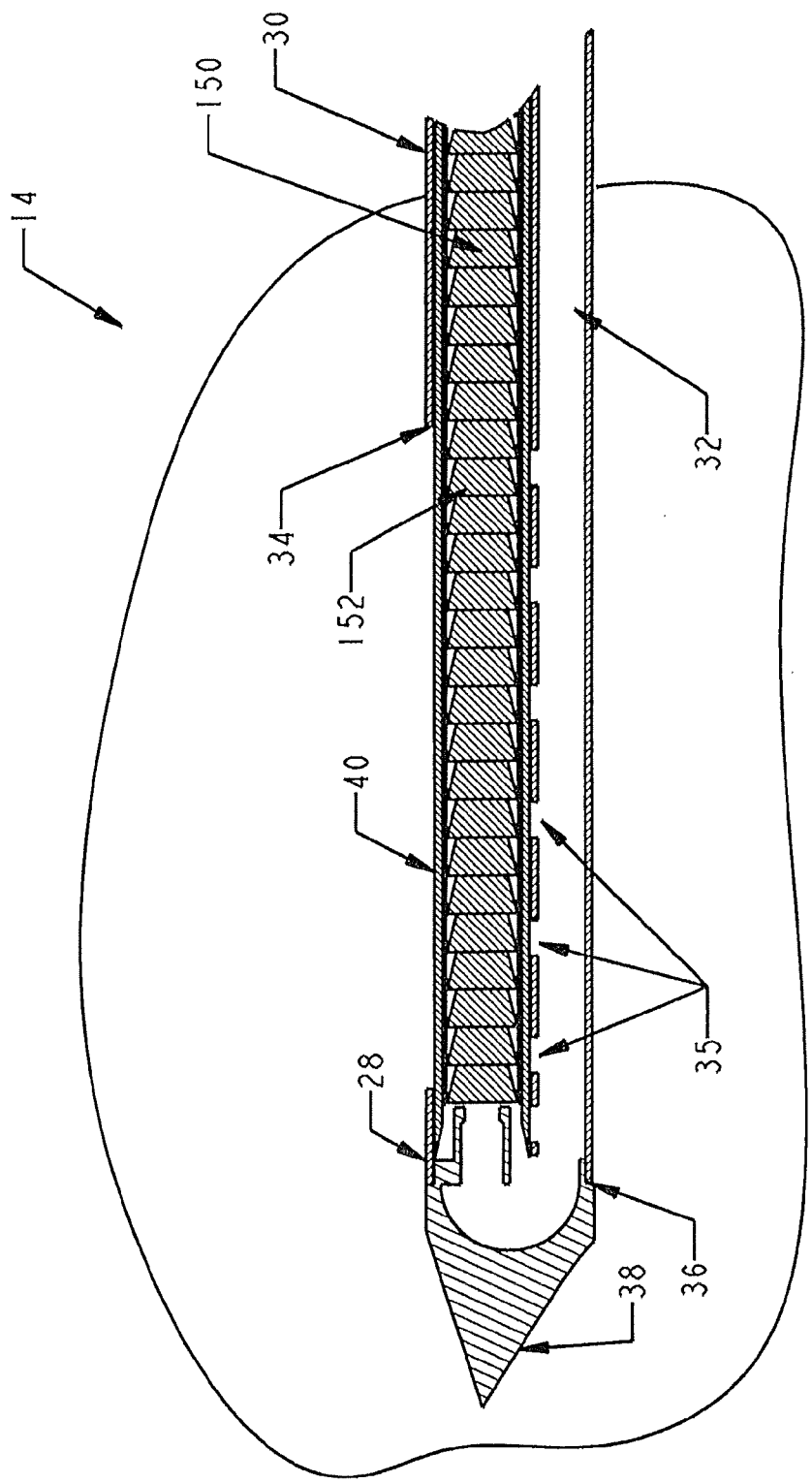
FIG. 14 is a left side view of the probe inserted into tissue of the biopsy device of FIG. 12 in longitudinal cross section exposing the distally translated cutter tube, elongate straw, and indicator tube.

In FIGS. 12, 14, the cutter and straw carriages 250, 258 may initially be distally advanced to close the side aperture 34 of its probe tube 30 with the cutter tube 40 and the stacking straw assembly 100 also fully distally advanced to minimize proximal extension of its elongate straw 102.

In FIG. 13, the piercing tip 38 of the core biopsy needle (probe) assembly 28 is assisted in penetrating tissue by moving the slide button 168 distally to a "tissue insertion mode" wherein the slide spur gear 176 engages the tissue penetration gear 190. Depression of the forward motor rotation key 162 turns these gears 176, 190 causing the circular cam wheel 216 to turn against strike pin 214 that creates proximal longitudinal motion of frame 204 and core biopsy needle (probe) assembly 28 of approximately 0.1 inch at a rotation rate of 7 cycles per second. Left and right compression springs 226, 228 provide the restoring distal longitudinal motion to frame 204 and disposable probe 14 as left and right compression springs 226, 228 are repeatedly compressed between the forward surface of the left and right spring cavities 218, 220 as the frame 204 and the left and right tabs 222, 224 of the housing 20. The restoring distal longitudinal motion to frame 204 and core biopsy needle (probe) assembly 28 result in a corresponding distal motion of piecing tip 38 that assists in penetrating tissue.

Figure 15:
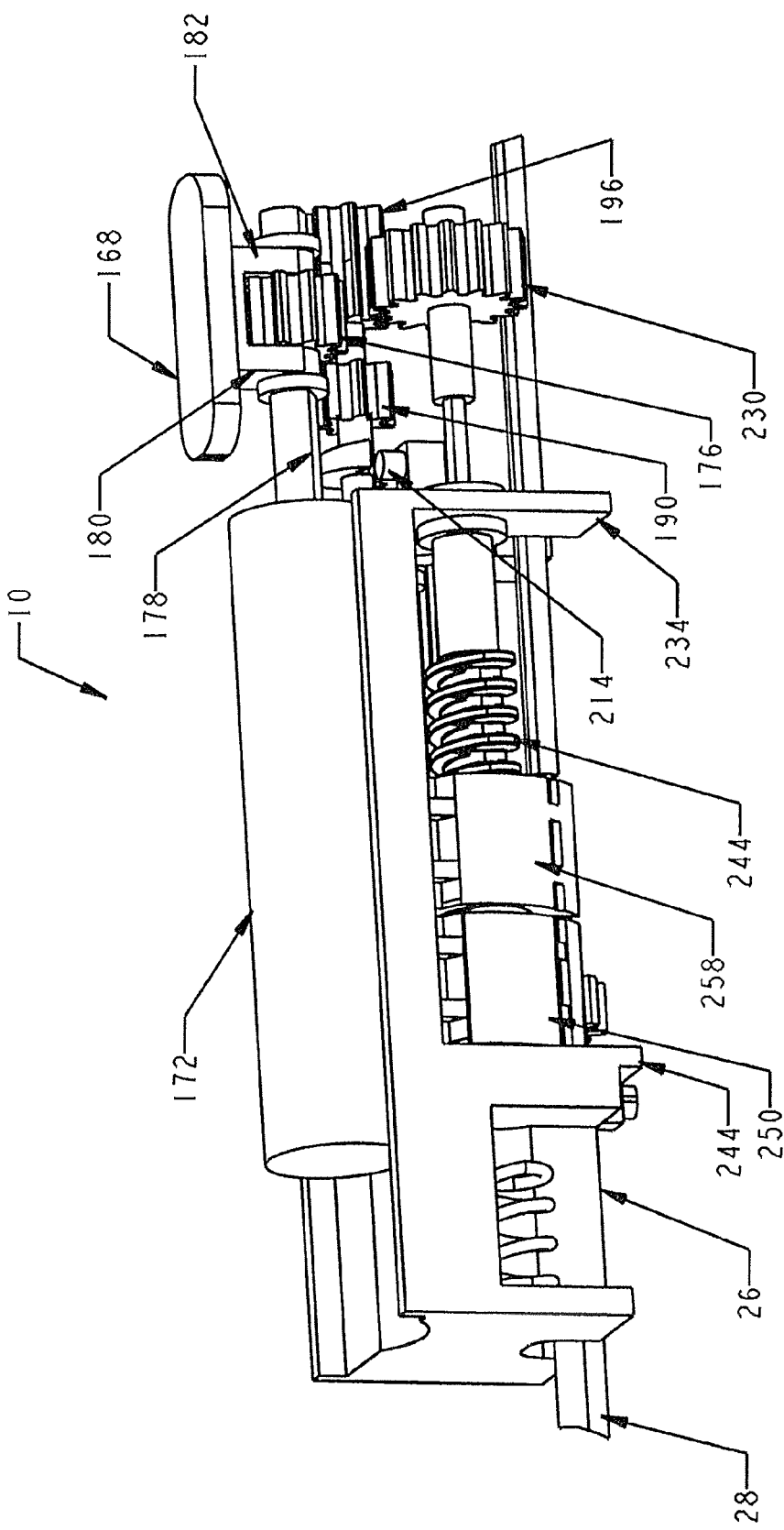
FIG. 15 is a left perspective view of the biopsy device of FIG. 12 with the housing removed.

In FIG. 15, with the side aperture 40 positioned within the tissue to take samples, the slide button 168 is moved proximally to engage the slide spur gear 176 with the distal small gear 198 of the gearbox input gear 196. When the forward motor rotation key 162 is depressed, the DC motor 172 rotates in a forward direction, turning the slide spur gear 176, which turns the distal small gear 198 that directly turns the translation large input gear 230 that is connected by the shaft 232 through the aft wall 234 of the frame 204 to the lead (translation) screw 244. Meanwhile, the proximal large gear 200 of the gearbox input gear 196 rotates the small input gear 236 that turns shaft 238 through aft wall 234 to turn the rotation spur gear 246.

Figure 16:
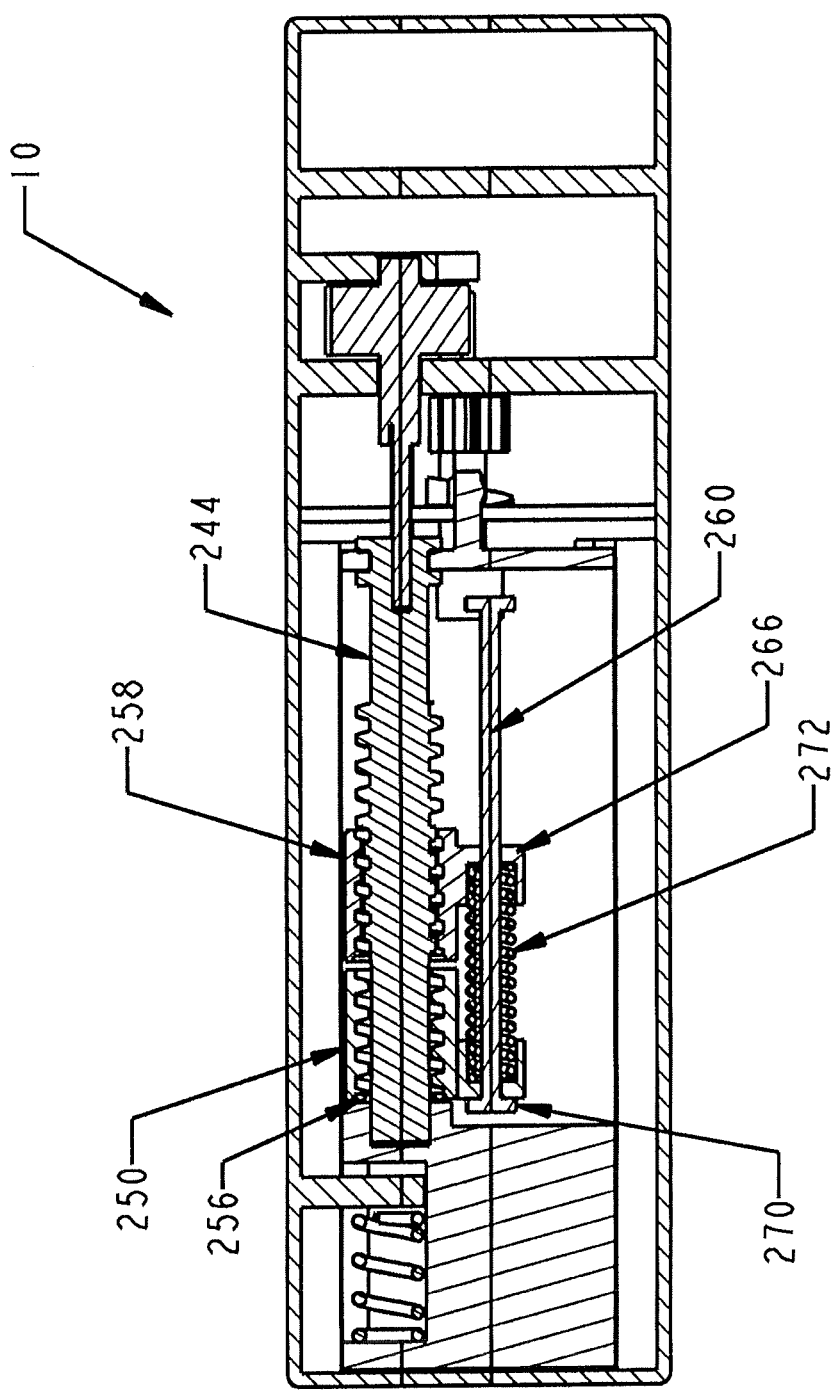
FIG. 16 is a bottom view of the biopsy device of FIG. 6 taken in cross section along staggered lines 16-16 through a lead (translation) screw and a slide pin engaged to the cutter and straw carriages.
Figure 17:
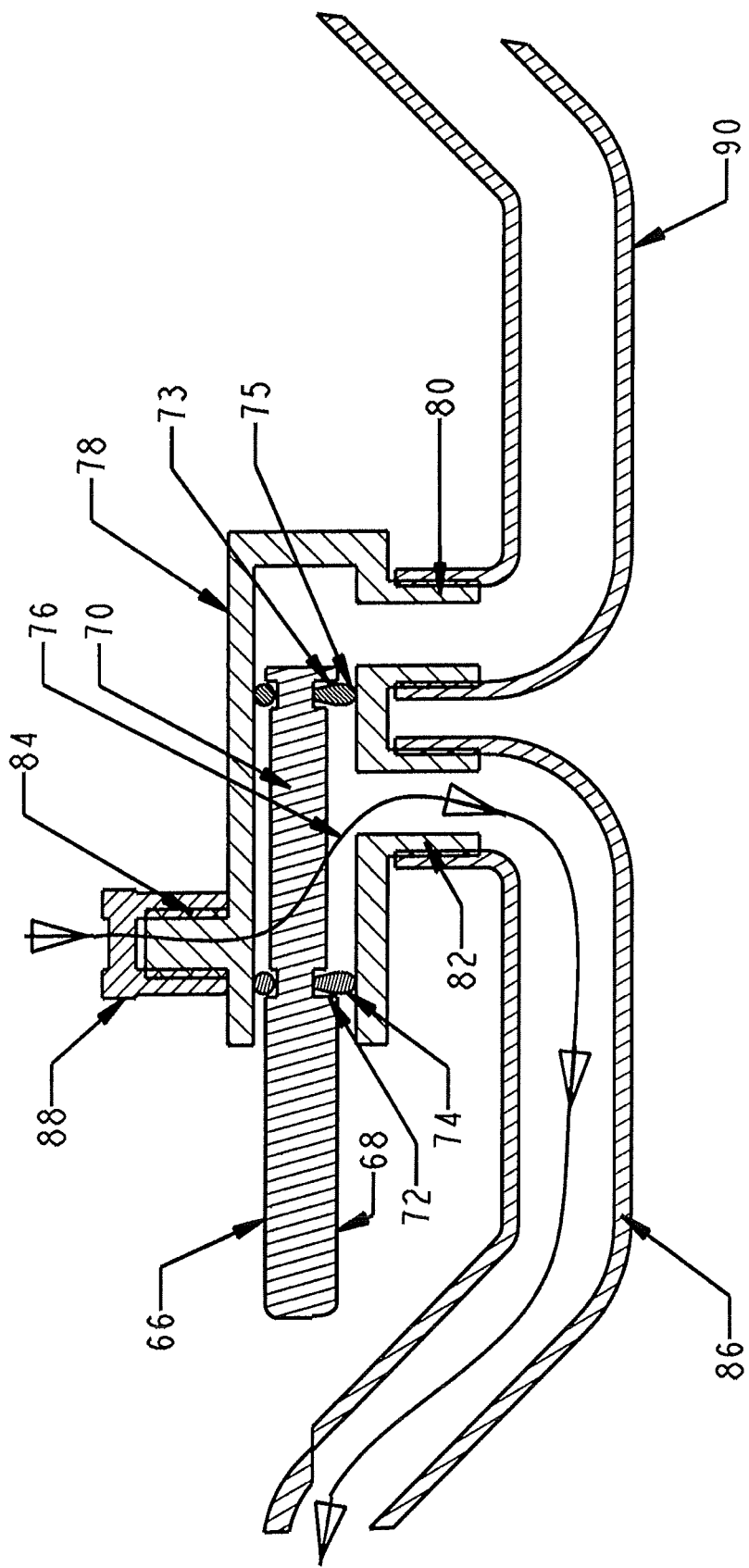
FIG. 17 is a bottom view of the biopsy device of FIG. 6 taken in horizontal cross section along lines 17-17 through a pneumatic valve that sequences vacuum assistance corresponding to cutter position.

With the carriages 250, 258 distally advanced as depicted in FIGS. 15-16, the cylindrical proximal portion 70 of the vacuum valve actuator 68 is also distally positioned as depicted in FIG. 17. The hose nib 88 is thus in fluid communication through the distal port 84, through the distally open cylindrical valve bore 76 between distal and proximal dynamic O-ring seals 74, 75 to the center port 82 through the distal vacuum conduit 86 to the vacuum lumen 32.

Figure 18:
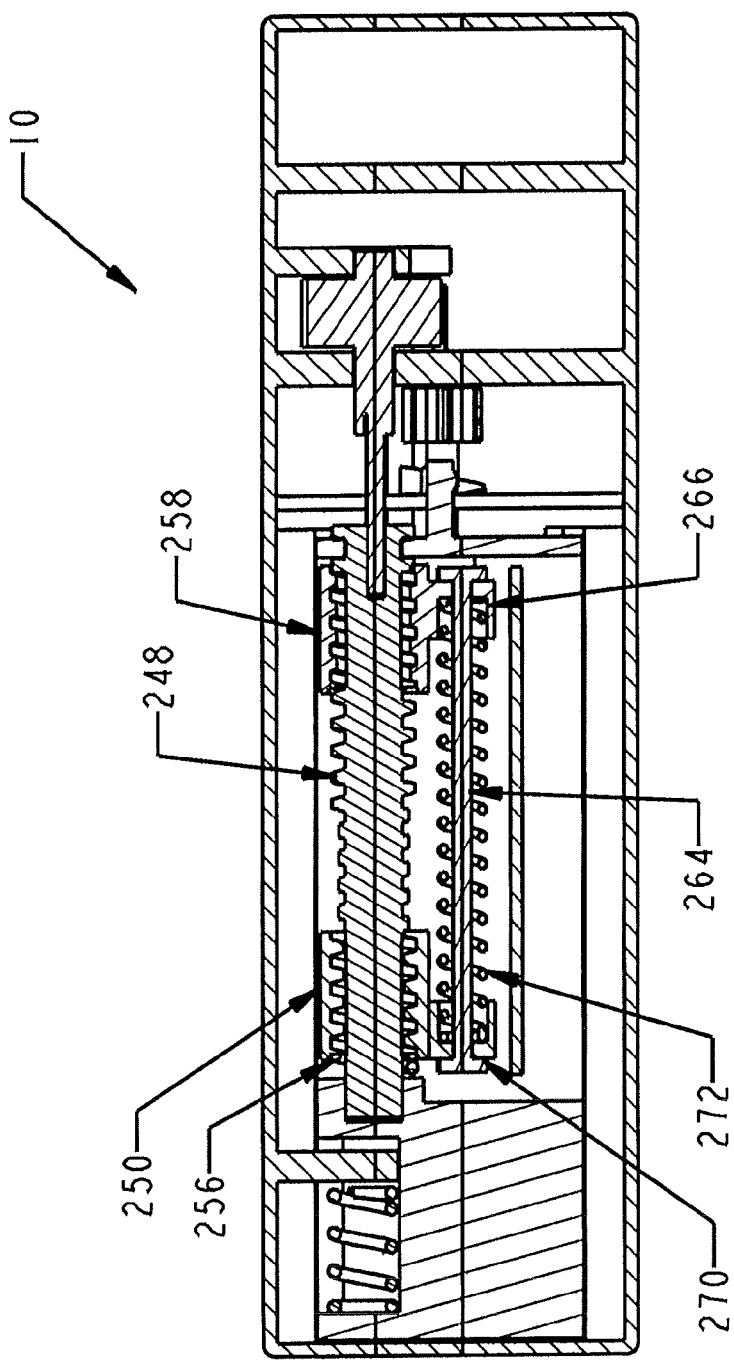
FIG. 18 is a bottom of the biopsy device of FIG. 16 in cross section after proximal retraction of the straw carriage.
Figure 20:
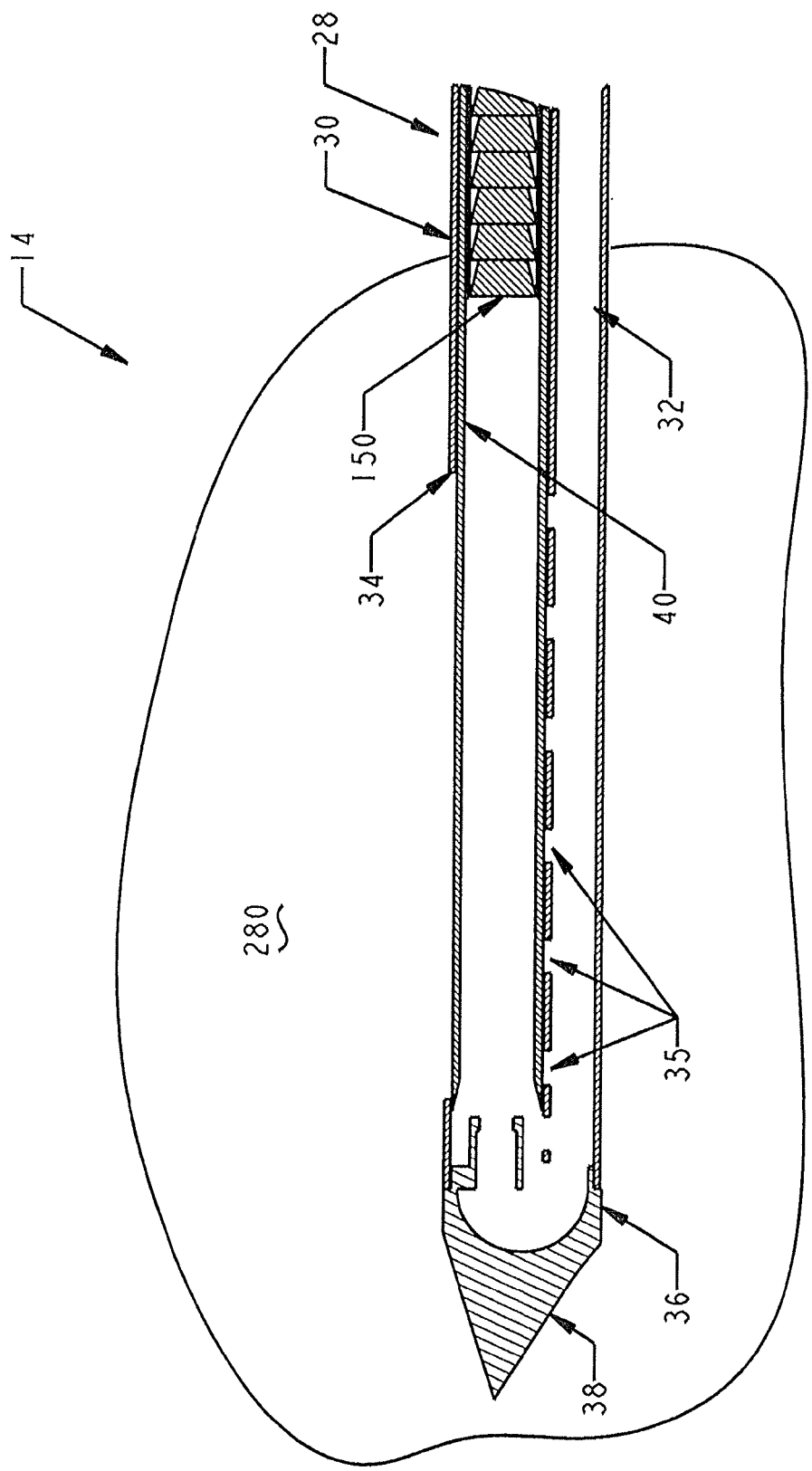
FIG. 20 is a left view in elevation of the probe in longitudinal cross section of the biopsy device of FIG. 18 with the elongate straw and indicator tube retracted.
Figure 21:
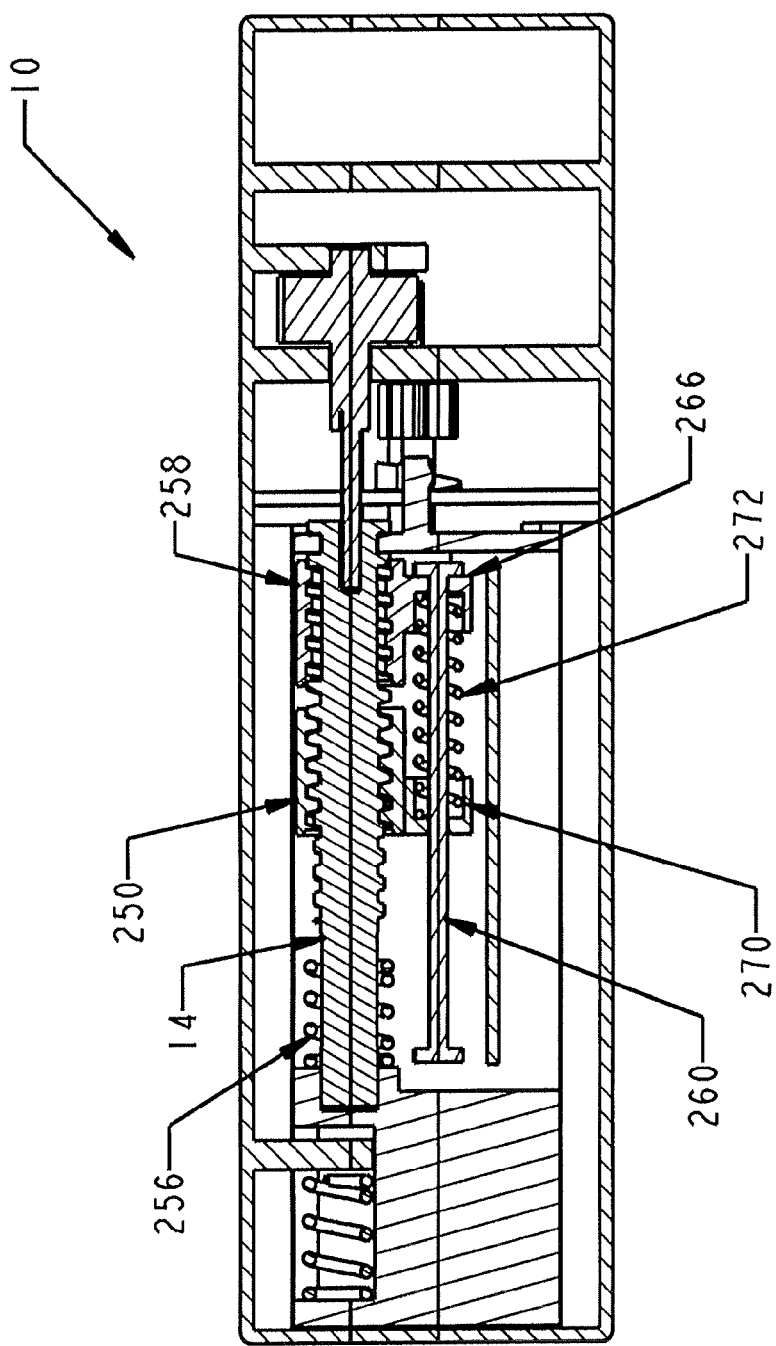
FIG. 21 is a bottom of the biopsy device of FIG. 18 in cross section with both the cutter carriage and straw carriage retracted.
Figure 22:
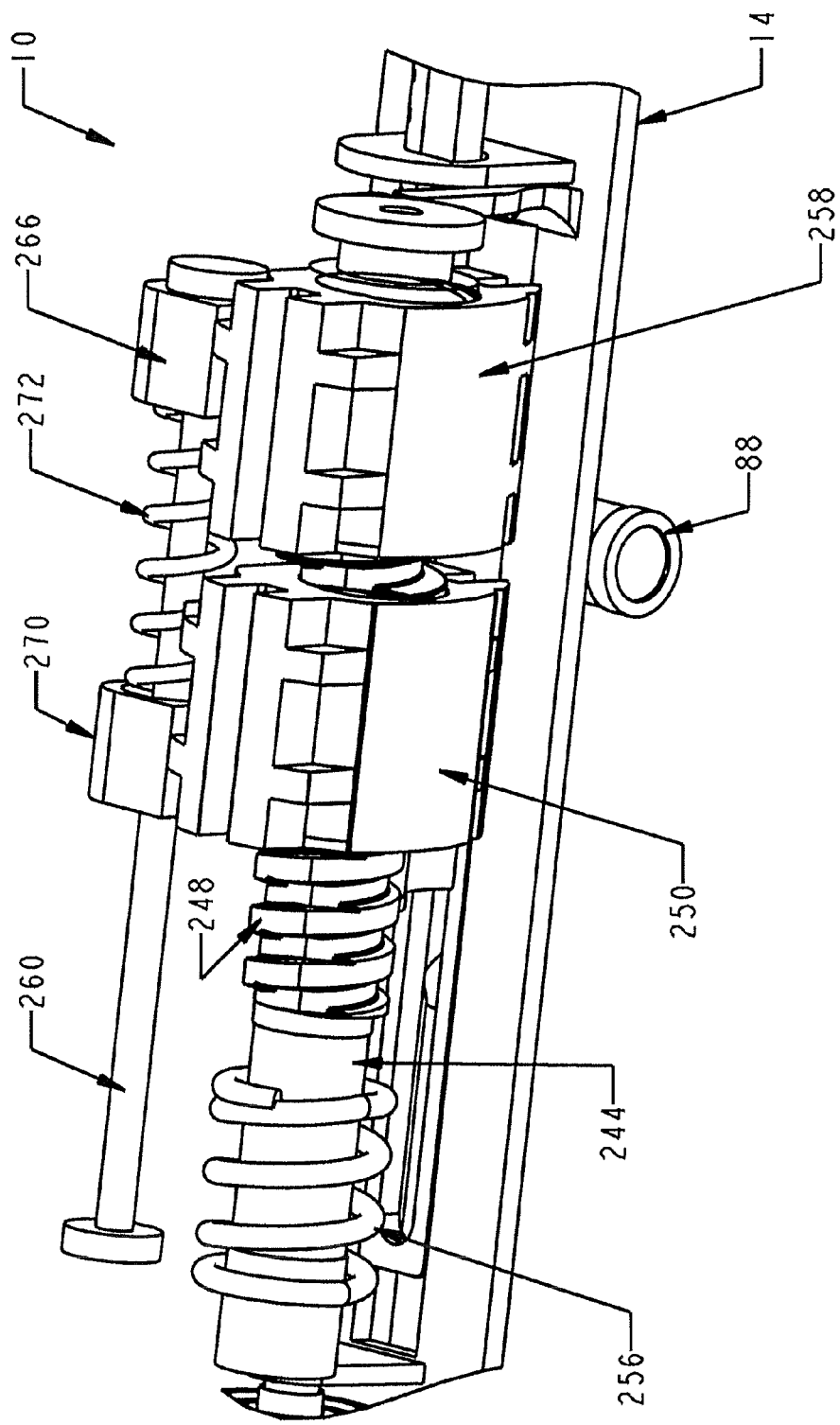
FIG. 22 is a left perspective detail view of the carriages, lead screw, and sliding pin of the biopsy device of FIG. 21.

In FIGS. 18-19, depression of the reverse motor rotation key 164 causes the lead (translation) screw 244 to rotate in a reverse direction. Sliding pin spring 272 between the distal cutter carriage 250 and the proximal straw carriage 258 urges the proximal straw carriage 258 into engagement with the lead screw thread 248, causing the straw carriage 258 to move proximally as the cutter carriage 250 free wheels on an unthreaded distal portion of the lead screw 244. The straw carriage 258 draws back the elongate straw 102 and the indicator tube 150 (FIG. 20). As the straw carriage 258 approaches the proximal portion of the lead screw 244, the distal end 268 of sliding pin 260 contacts the distal carriage sliding pin retainer 270 on distal cutter carriage 250, pulling the distal cutter carriage 250 onto the lead screw thread 248. Thereafter, the cutter carriage 250 and the cutter tube 40 are retracted as the straw carriage 258 free wheels (FIGS. 21-22).

Alternately, sliding pin spring 272 may be replaced with a ball detent mechanism (not shown) located on frame 204 that would engage with a small depression in proximal straw carriage 258. This alternate mechanism in conjunction with biasing spring 256 would cause both the distal cutter carriage 250 and proximal straw carriage 258 to retract simultaneously from their fully distal position and to advance sequentially from their fully proximal position (i.e., cutter carriage 250 would fully advance and then the straw carriage 258 would advance).

Figure 23:
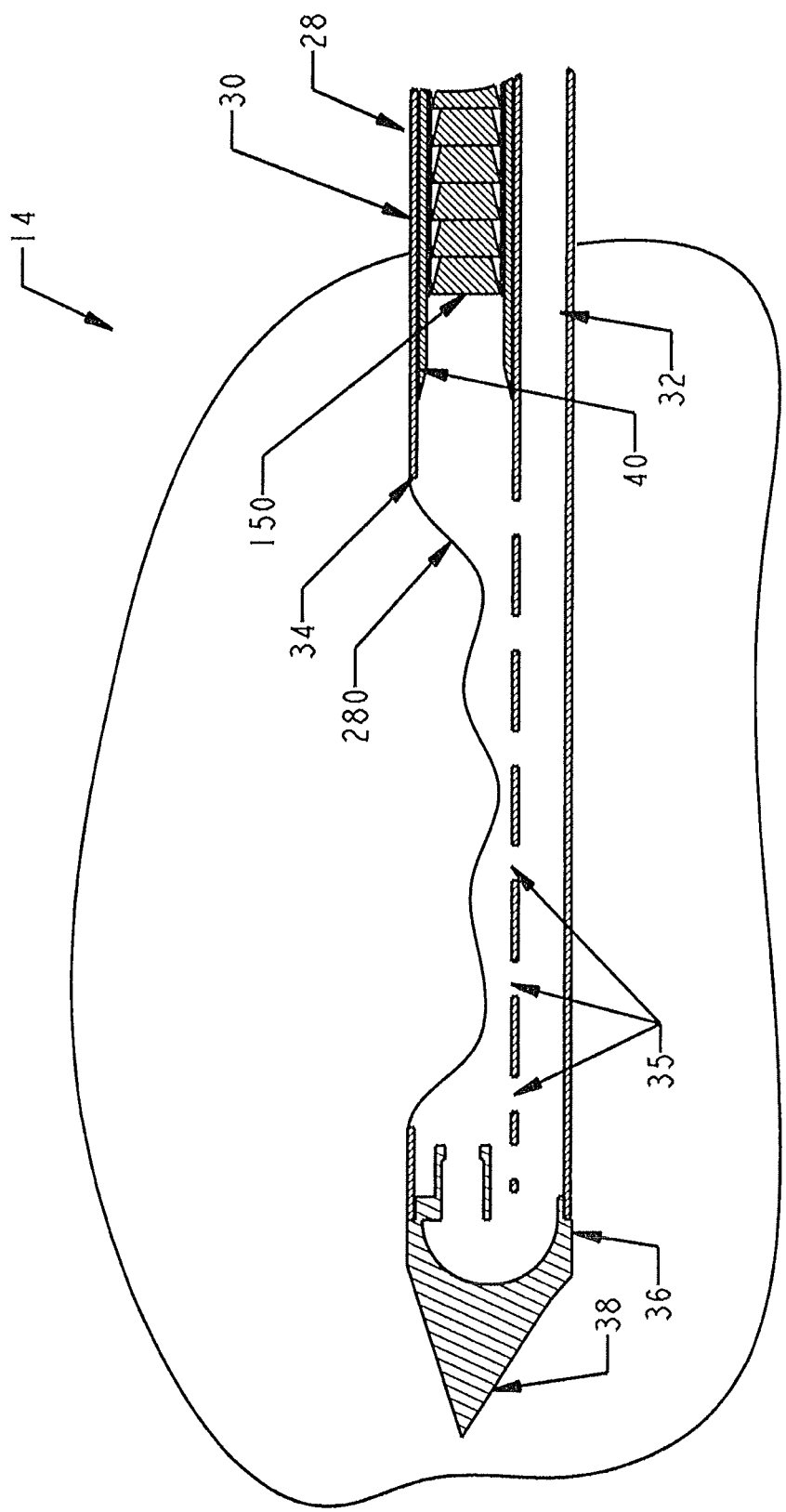
FIG. 23 is a left view in elevation of the probe in longitudinal cross section of the biopsy device of FIG. 21 with vacuum assistance prolapsing tissue into the side aperture.
Figure 24:
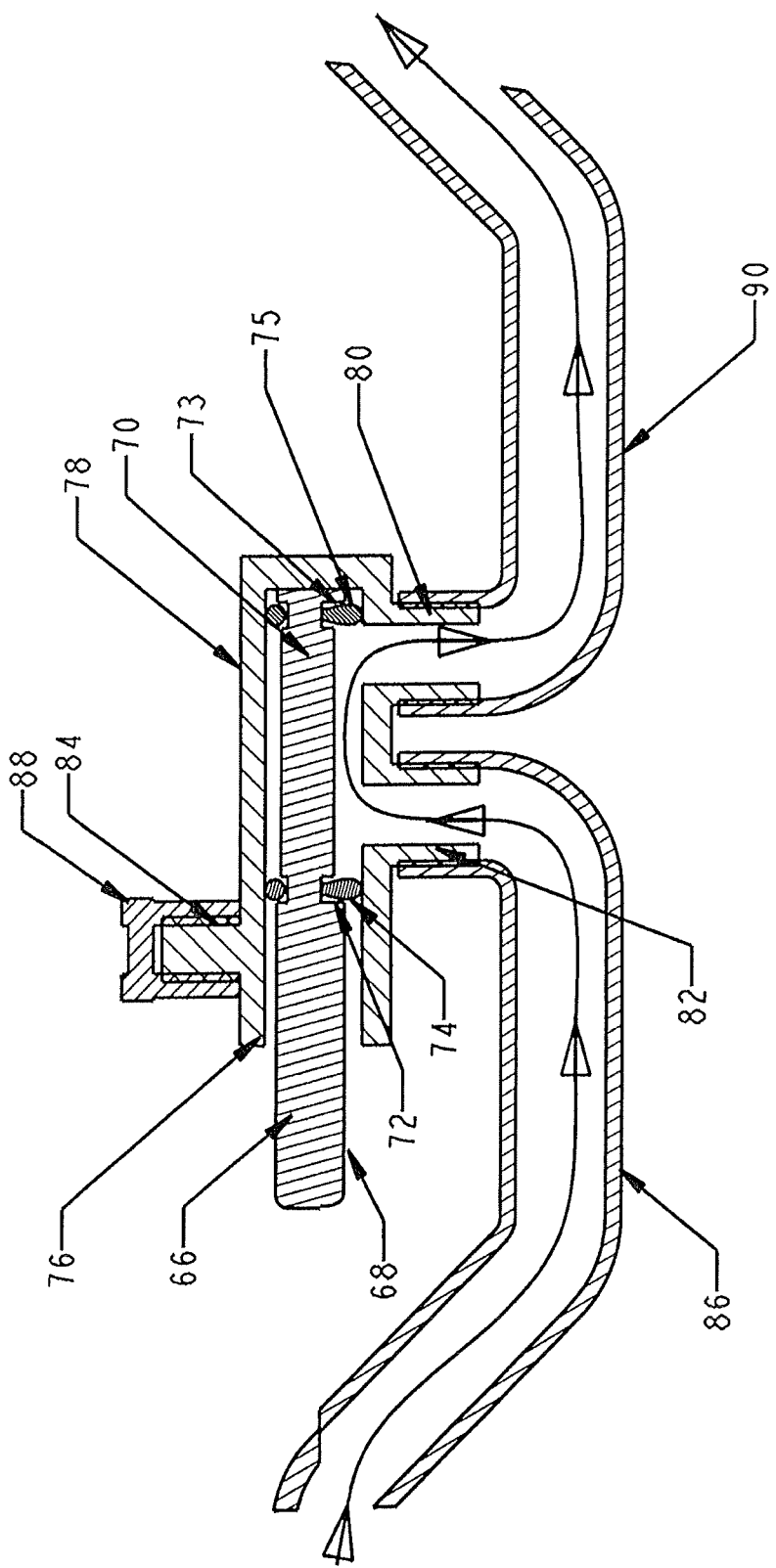
FIG. 24 is a bottom view of the pneumatic valve in horizontal cross section of the biopsy device of FIG. 21.

At the end of the proximal movement of the cutter tube 40, vacuum valve actuator 68 is moved proximally such that the distal and proximal dynamic O-ring seals 74, 75 bracket the proximal port 80 and center port 82 of the distally open cylindrical valve bore 76. Thereby, the interfacing vacuum conduit 16 draws air through the proximal vacuum conduit 90, through the valve body 78, through the distal vacuum conduit 86, and ultimately from the vacuum lumen 32 (FIG. 24). In FIG. 23, this suction draws tissue 280 into the side aperture 34 of the probe assembly 28.

It should be appreciated that in the illustrative version, the distal cutter carriage 250 does not freewheel (FIG. 21) in its proximal-most position. Instead, rotation of the motor is stopped as the distal cutter carriage 250 is about to contact the proximal straw carriage 258 with closed-loop control based on an encoder (not shown) coupled to the DC motor 172 enabling accurate positioning of the motor output shaft 174. Alternatively, freewheeling may be incorporated at the proximal-most position of the distal cutter carriage 250 by adding a section of no helical threads to the proximal end of the lead (translation) screw 244 equal to the longitudinal thickness of the distal cutter carriage 250.

It should further be appreciated that free wheeling may be provided for cutter translation even without stacking straw sample retraction to avoid reliance upon other structures to block further translation or more elaborate closed loop position control.

Figure 25:
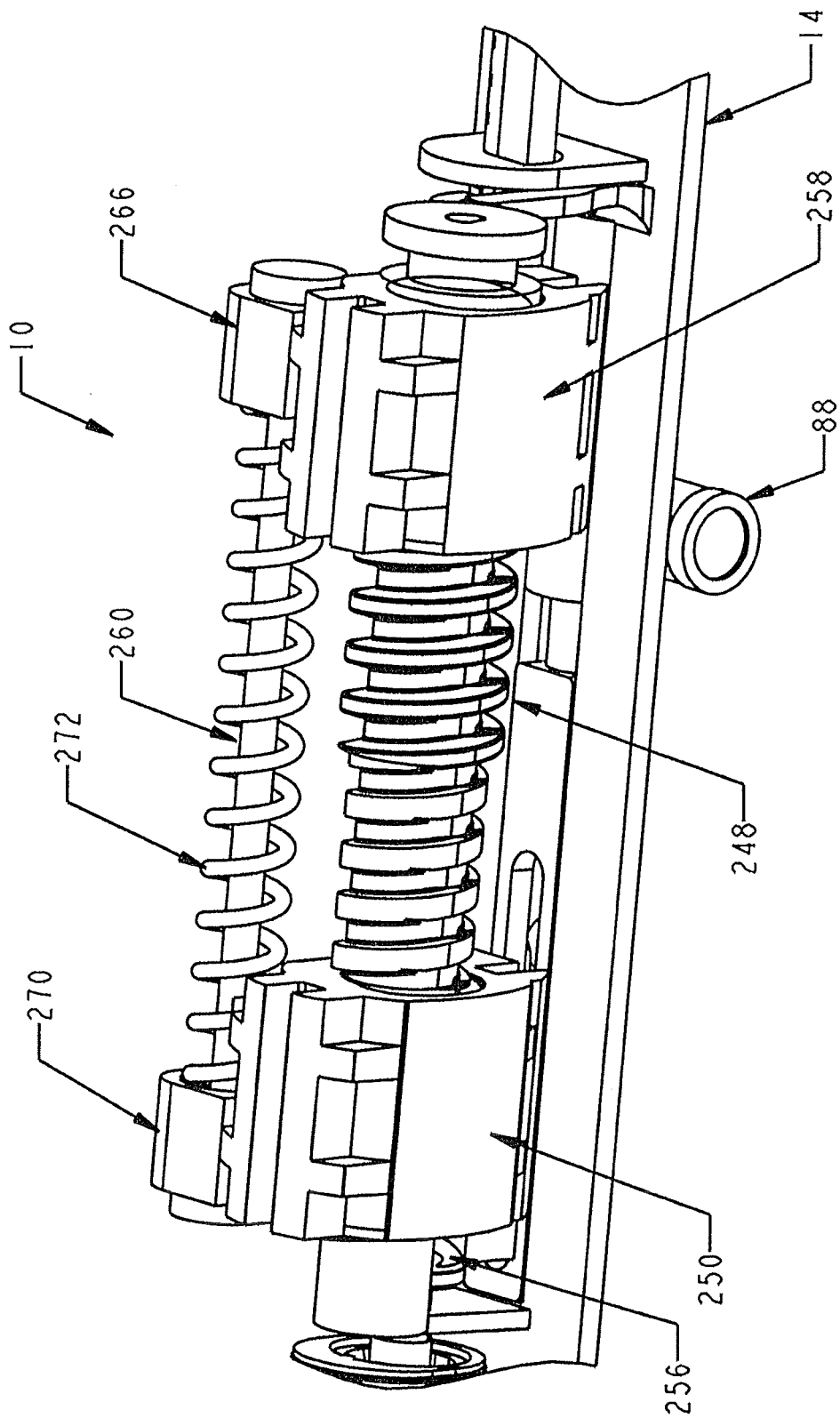
FIG. 25 is a left perspective detail view of the carriages, lead screw and sliding pin of the biopsy device of FIG. 21 after distal translation of the cutter carriage.
Figure 26:
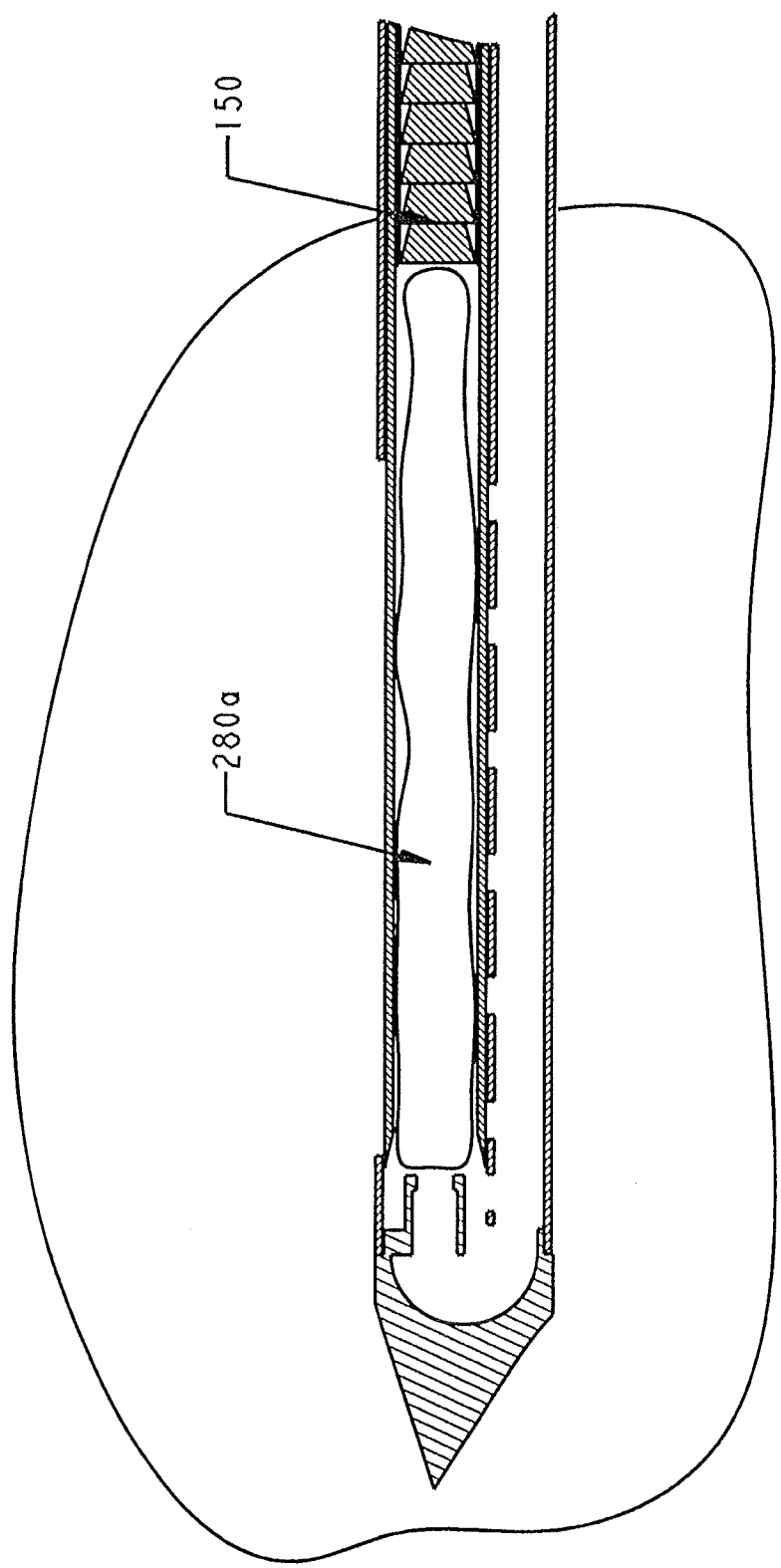
FIG. 26 is a left side view of the probe in longitudinal cross section of the biopsy device of FIG. 25 after severing tissue.

The forward motor rotation key 162 is depressed to advance the cutter tube 40, rotating lead (translation) screw 244 and rotation spur gear 246, as depicted in FIG. 25. Due to sliding pin spring 272 between carriages 250, 258, only the distal cutter carriage 250 engages with the lead screw threads 248 of the lead (translation) screw 244 and translates distally initially cutting tissue 280, as depicted in FIG. 26. Once the distal cutter carriage 250 approaches its distal-most position, the sliding pin 260 pulls the proximal straw carriage 258 into engagement with the lead screw threads 248 of the lead (translation) screw 244. As the cutter carriage 250 freewheels, the elongate straw 102 is distally translated to encompass a first severed tissue sample 280a, displacing proximally the indicator tube 150 a corresponding amount.

Figure 27:
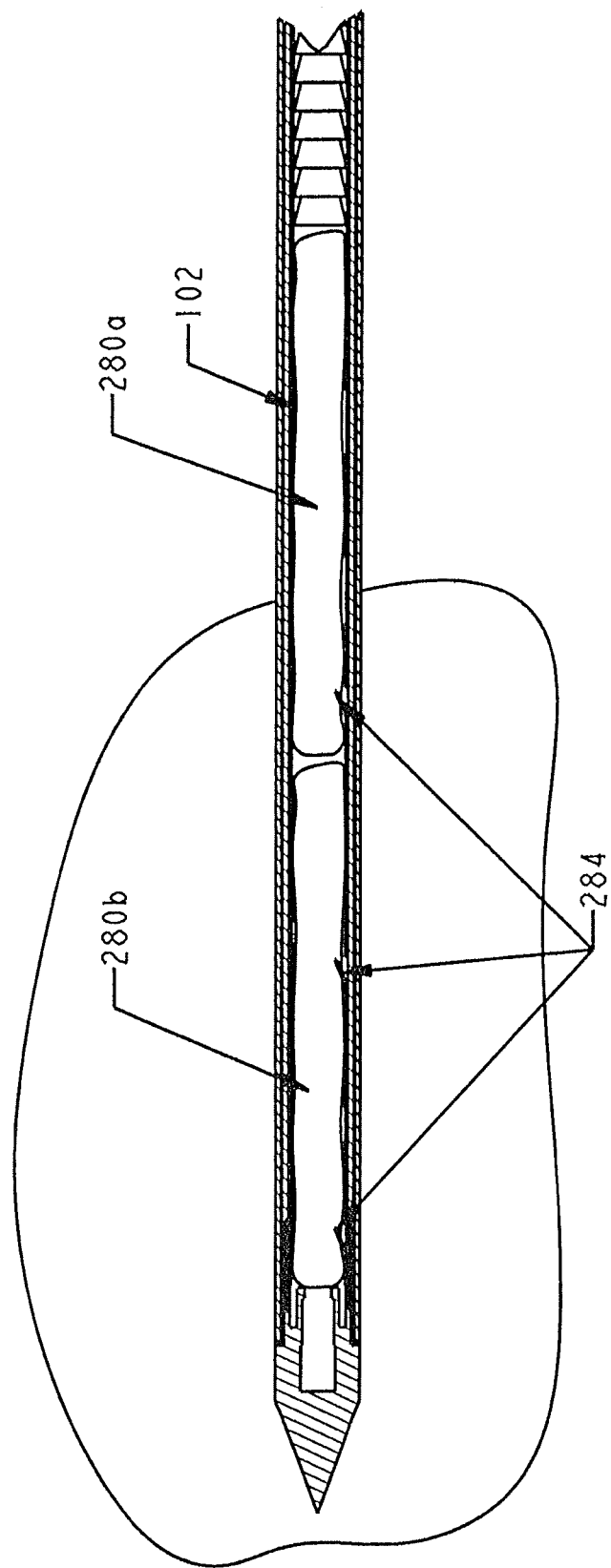
FIG. 27 is a left side view of the probe in longitudinal cross section of the biopsy device of FIG. 26 with distally translated cutter and straw carriages after taking two samples held in the elongate straw by bent up tabs with corresponding proximal extrusion of the indicator tube.

At this point, depression of the reverse motor rotation key 164 causes retraction of the proximal straw carriage 258 (FIG. 18) with the side aperture 134 communicating with atmospheric pressure (FIG. 17) as previously discussed so that the first severed tissue sample 280a remains within the elongate straw 280a. It should be appreciated that repeating the retraction and advancement of the cutter carriage 250 thereafter results in a second severed tissue sample 280b being encompassed by the elongate straw 102 and the indicator tube 150 being further proximally displaced thereby as depicted in FIG. 27. An additional retention feature is depicted in FIG. 27 wherein small bent-up, proximally directed tabs 284 formed in the elongate straw 102 resist distal movement of the severed tissue samples 280a, 280b. This automated sequencing of the cutter and straw carriages 250, 258 during retraction and advancement may be repeated a number of times to take a plurality of samples without withdrawing the probe assembly 28 from tissue 280. The surfaces of the elongate straw 102 may be coated with lubricous materials to aid in proximal movement of tissue through the elongate straw 102 and to reduce friction between the elongate straw 102 and the cutter tube 40. Likewise, to aid in proximal movement of tissue through the elongate straw 102, the diameter of the elongate straw 102 and the cutter tube 40 may be increased slightly some distance proximal from their distal end to reduce the friction of the tissue through the elongate straw 102.

Figure 28:
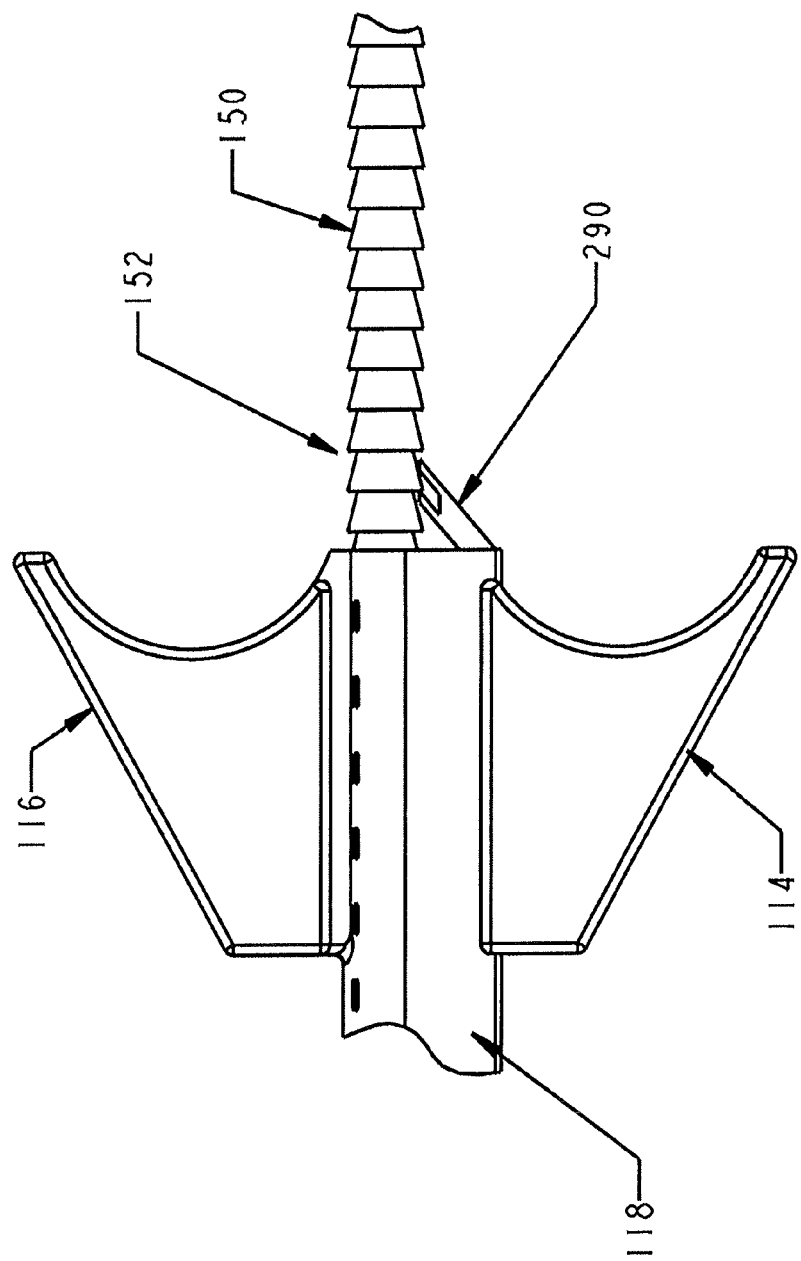
FIG. 28 is a left side detail view in elevation of a proximal portion of the stacking straw assembly including a mechanical diode preventing distal movement of the indicator tube into the elongate straw.

In FIG. 28, a proximal end of the stacking straw assembly 100 includes a one-way latch (mechanical diode) 290 that engages the stacked cone shaped outer surface 152 of the indicator tube 150 as it proximally extends out of the elongate straw 102 preventing its being pneumatically drawn back into the elongate straw 102 when subsequently exposed to vacuum pressure.

Figure 32:
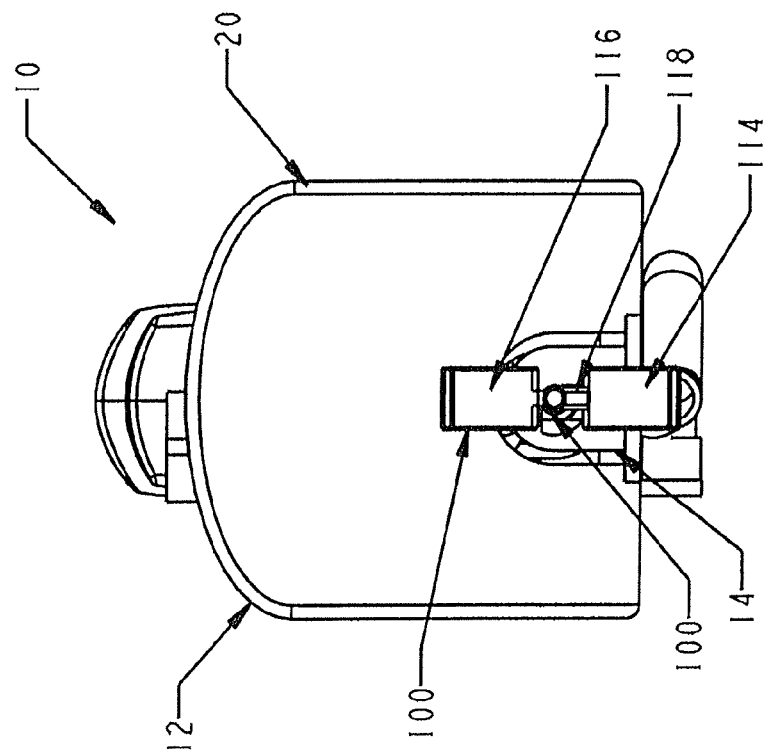
FIG. 32 is an aft view in elevation of the biopsy device of FIG. 29 with the stacking straw assembly rotated a quarter turn into engagement.
Figure 31:
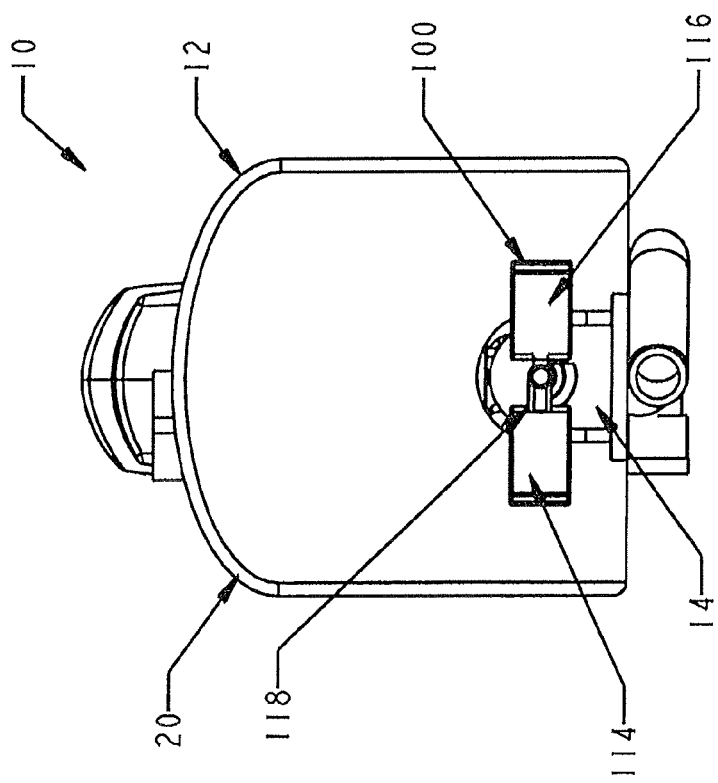
FIG. 31 is an aft view in elevation of the biopsy device of FIG. 30 with the disengaged stacking straw assembly.

In FIGS. 29, 30, the proximal straw carriage 258 is shown to include distal and proximal J-hooks 300, 302 that encompass on three sides the stacking straw assembly 100. In particular, the rectangular recess 134 formed in the locking strip 118 is sized to longitudinally bracket the J-hooks 300, 302 with the distal locking finger 136 preventing retraction as depicted in FIG. 29 when the triangular grips 114, 116 are positioned horizontally (FIG. 31), as would be typical before and during use of the biopsy device 10. The surgeon may wish to segregate samples as they are taken or to take more samples than possible within one stacking straw assembly 100. Extraction and replacement of the stacking straw assembly 100 is allowed by rotating the triangular grips one quarter turn counterclockwise (as viewed proximally) as depicted in FIG. 32, which rotates the locking finger 136 out of alignment with the J-hooks 300, 302 of the straw carriage 258 (FIG. 30). A new stacking straw assembly 100 is then reinserted in reverse fashion.

Figure 33:
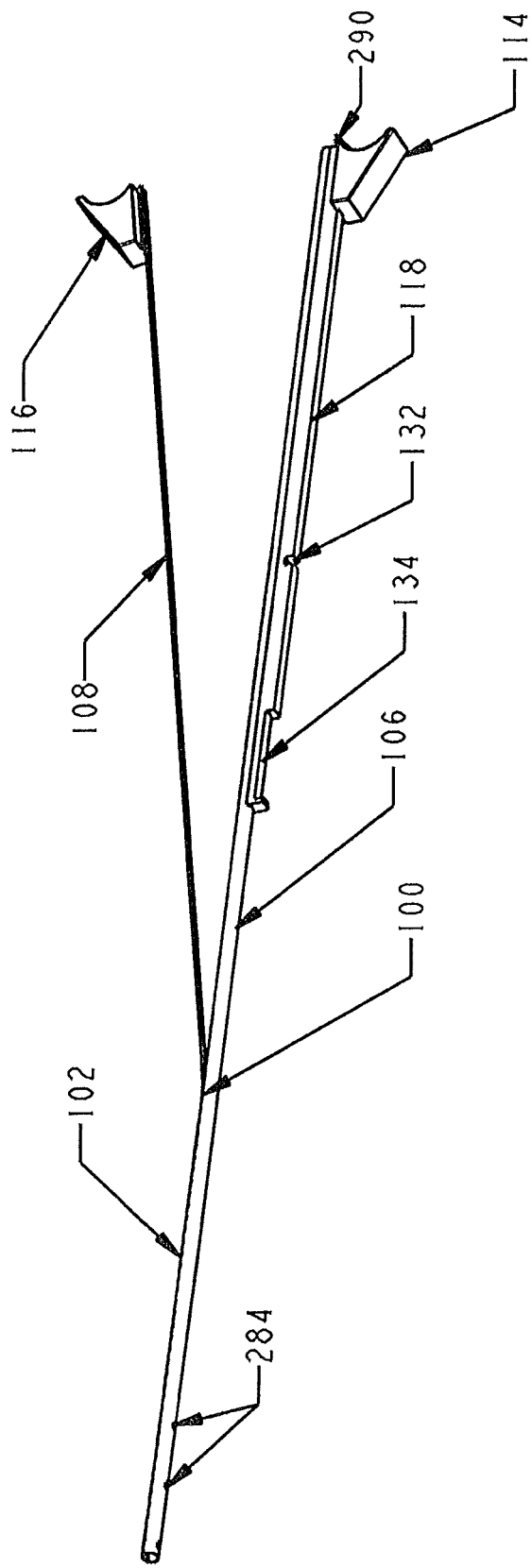
FIG. 33 is a perspective view of the stacking straw assembly of the biopsy device of FIG. 1 after removal and peeling apart to access samples.

In FIG. 33, samples contained in the removed stacking straw assembly 100 may be accessed by pulling apart the triangular grips 114, 116 causing the grooves 104 to peel apart the first and second straw halves 106, 108, which need not be symmetric. The samples may be removed individually or the samples and the straw half 106 portion of the straw 102 in which they are located may be put directly into a formalin solution for pathological preparation. Alternately, the samples contained in the stacking straw assembly 100 can be removed from the elongate straw 102 with a simple plunger-like rod (not shown) eliminating the need to peel apart the straw to access the tissue samples.

Figure 36:
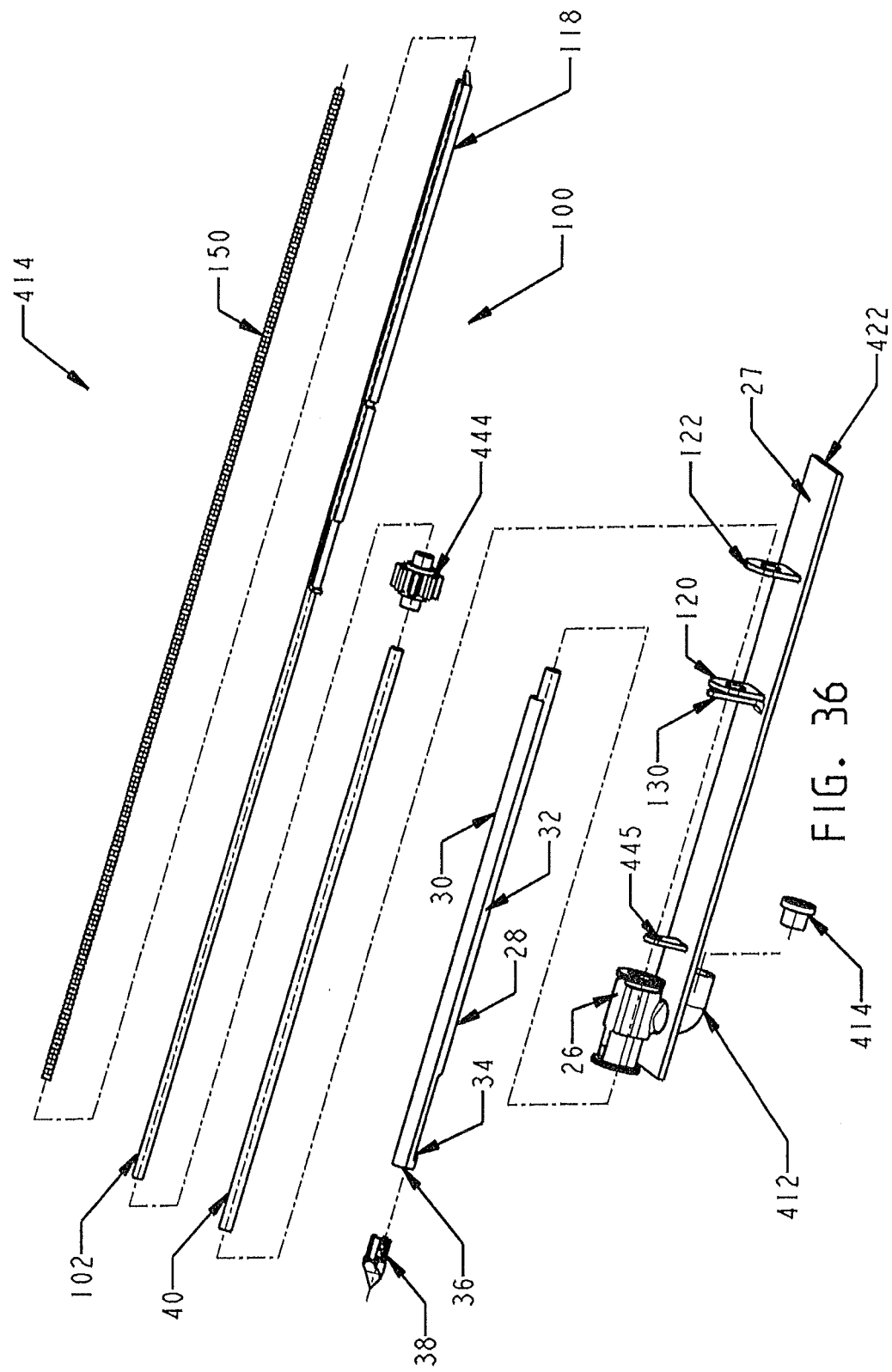
FIG. 36 is a disassembled perspective view of the alternative probe assembly of FIG. 34.

Although the integral vacuum assistance supported by a medical vacuum pump may often be advantageous, some surgeons may desire to palpitate tissue into a side aperture of a probe assembly without the assistance of vacuum. To that end, in FIGS. 34-36, an alternative disposable probe 414 is depicted that omits a vacuum valve capability that responds to the cutter position but is otherwise identical to the aforedescribed disposable probe 14. The modified components of the disposable probe assembly 414 include a substantially rectangular cover 422 sized to close the access trough recess 18 of the reusable hand piece 12 (not shown in FIGS. 34-36). The probe union sleeve 26, attached to the inner surface 27 of the substantially rectangular cover 422, communicates through a short pneumatic conduit 425 that terminates on the outer surface 79 at a hose nib 427. Hose nib 427 may include an air and/or saline filter. Alternatively, hose nib 427 may be connected to a positive pressure source (e.g. fluid pump) or a negative pressure source (e.g., vacuum pump, syringe) to aspirate fluids. Hose nib 427 could also be used to lavage the tissue cavity with saline, pain medication, or bleeding control fluids. A core biopsy needle ("probe") assembly 428 that passes longitudinally through the probe union sleeve 26 differs in that a cutter gear 444 needs only engage and respond to the distal cutter carriage 250 (not shown in FIGS. 34-36) and not also position a pneumatic valve. Cutter guide tab 445 extends out from the inner surface 27 to provide a distal stop for cutter gear 444. Prior to insertion of the disposable probe 414 into the reusable hand piece 12 (not shown in FIGS. 34-36), the bayonet locking member 430 prevents axial movement of the stacking straw assembly 100. The cutter gear 444 and cutter tube 40 cannot move proximally due to contact with the stacking straw assembly 100 and cannot move distally due to contact with the cutter guide tab 445. By securing both the cutter and straw in a fully distal axial position, it insures that when the disposable probe 414 is inserted into the reusable hand piece 12 that the cutter gear 444 and stacking straw assembly 100 align and engage with the correct components within the reusable hand piece 12.

Figure 37:
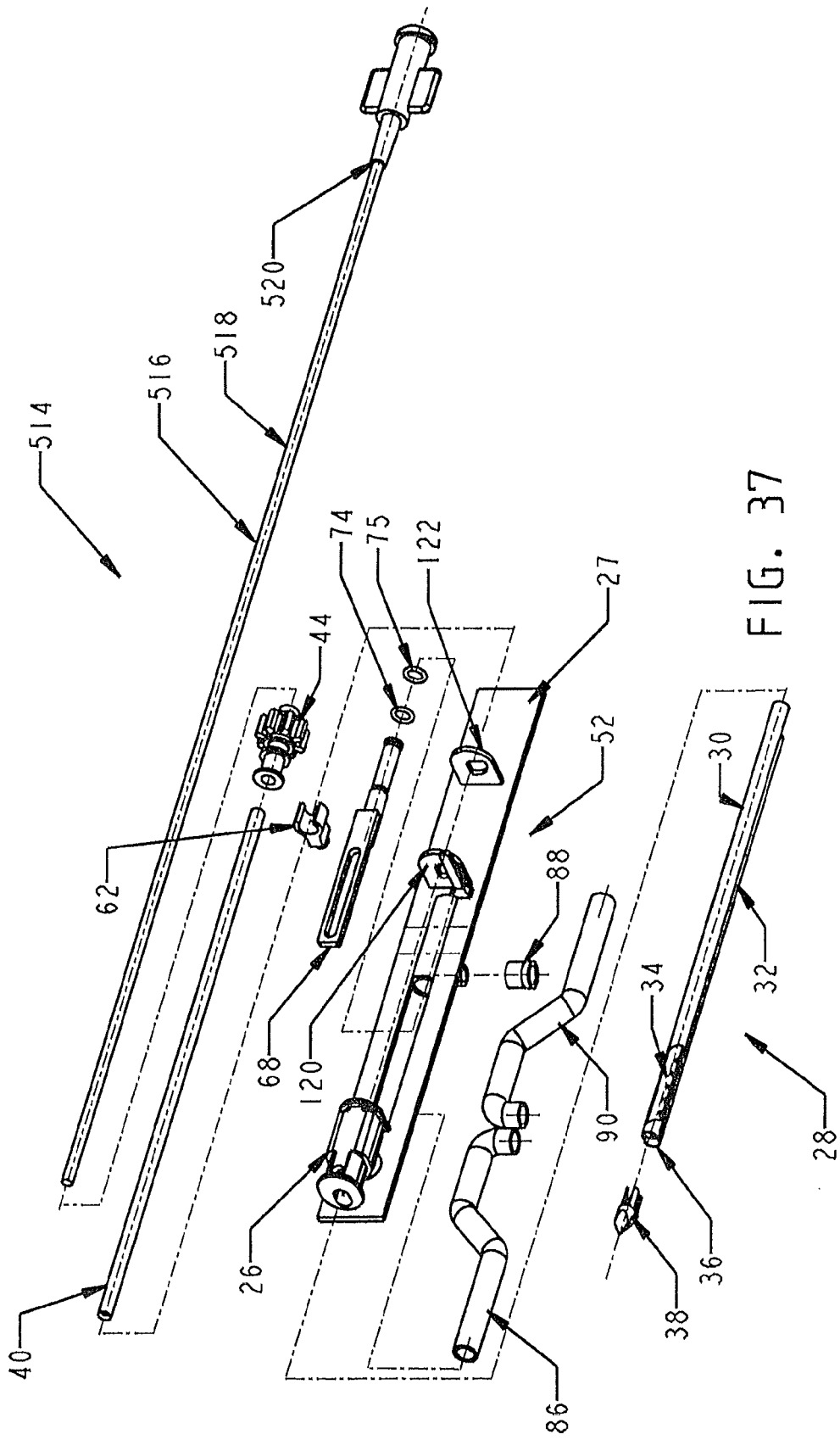
FIG. 37 is a disassembled perspective view of an alternative disposable assembly with a straw assembly having a luer fitting for the reusable hand piece of FIG. 1.

In FIG. 37, an alternative disposable assembly 514 is, as described in FIG. 3 but with the stacking straw assembly 100, replaced with a straw assembly 516 having distal tube 518 attached to a proximally attached luer fitting 520. The straw assembly 516 may be used to flush the cavity (via side aperture 34) with saline, epinephrine (or similar substances that reduce bleeding), or lidocane (or similar substances that reduce pain) by attaching a syringe or similar device (not shown) to the luer fitting 520. To remove the saline, epinephrine, or lidocane from the tissue, the cutter tube 40 may be fully or partially retracted to insure that the valve assist valve assembly 52 is positioned to connect the lateral lumen (distal vacuum conduit 86) with the vacuum source (and not simply atmospheric pressure) as depicted in FIG. 24. The fluid would then be drawn from the tissue cavity (via side aperture 34), through the lateral lumen (distal vacuum conduit 86) and into a canister located in line with the vacuum source (not shown).

Figure 38:
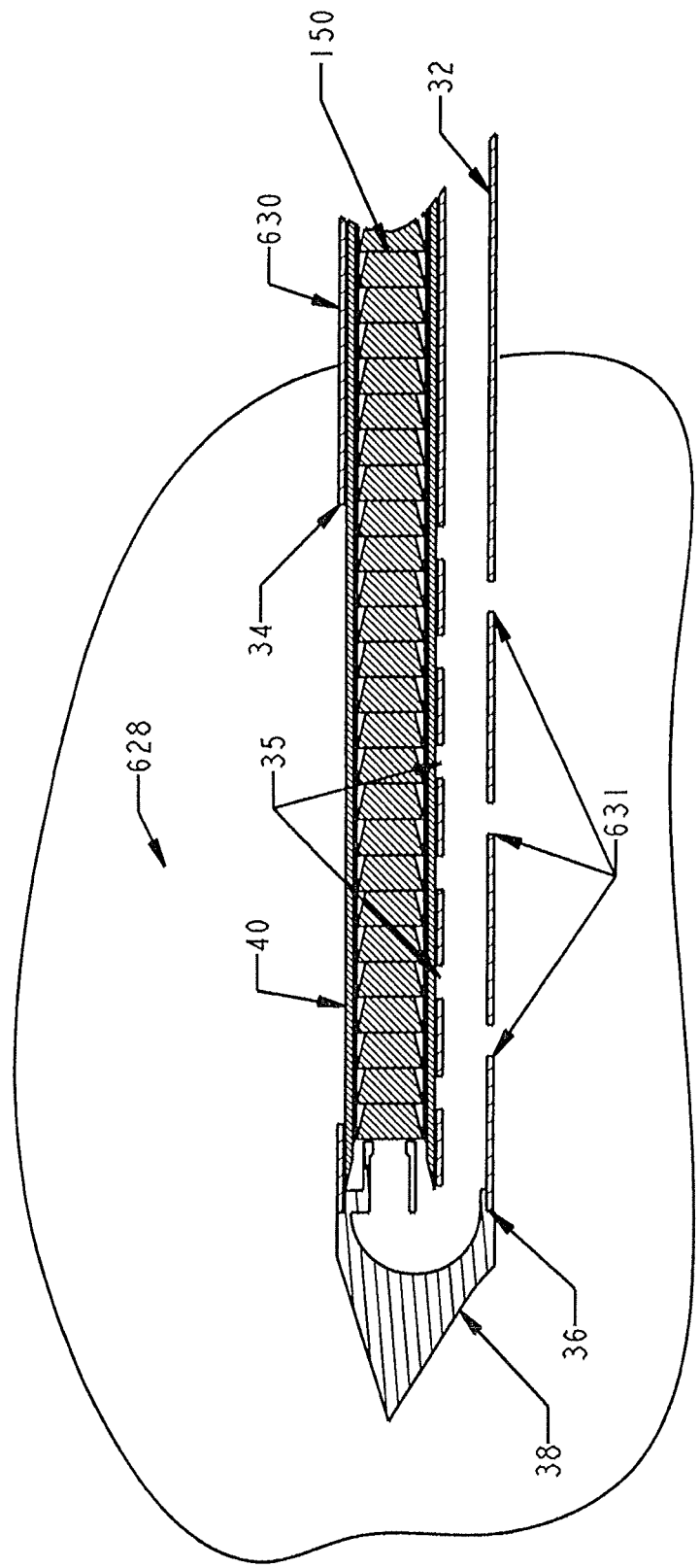
FIG. 38 is a left side view of an alternative probe inserted into tissue for the reusable hand piece of FIG. 1 in longitudinal cross section exposing the distally translated cutter tube, elongate straw, and indicator tube and with through holes in a probe tube.
Figure 39:
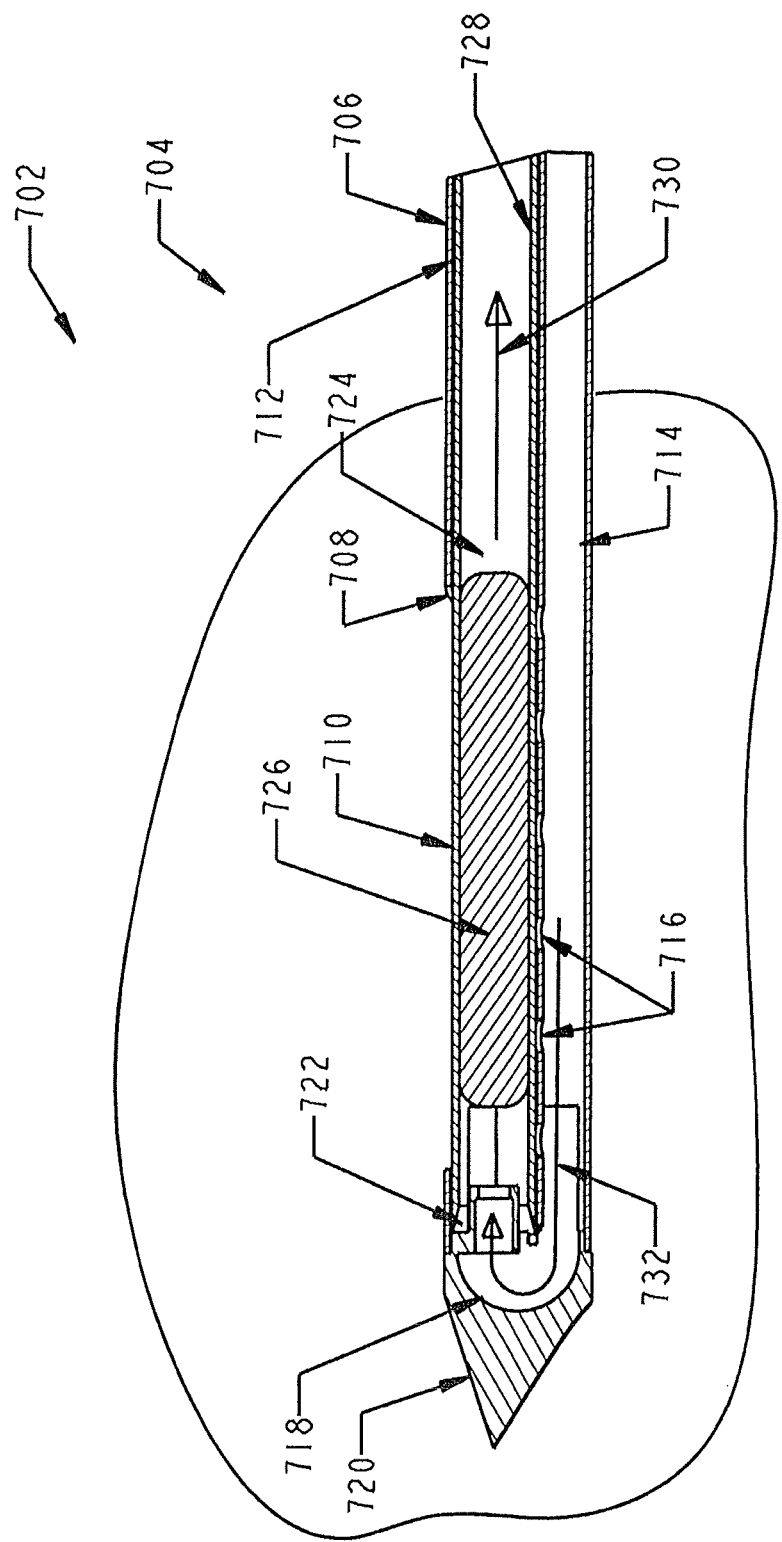
FIG. 39 is a left side view of another alternative probe inserted into tissue for the hand piece of FIG. 1 that employs pneumatic pressure to retrieve tissue samples through the cutter tube rather than a straw assembly.

In FIG. 38, an alternative biopsy needle (probe) assembly 628 is identical to that depicted in FIG. 14 with the exception of a probe tube 630 with through holes 631 placed proximate to the side aperture 34. The vacuum lumen 32 thus communicates with the holes 631 in the probe tube 630 as an alternate means to apply saline, epinephrine, or lidocane to the tissue cavity. These through holes 631 allow the fluid to reach the cavity while the elongate straw 102 and indicator tube 150 remain distally positioned in the cutter tube 40 (i.e., during the middle of a biopsy sampling procedure). In this case, the syringe would be attached to the hose nib 88 via a stopcock fitting (not shown). With the stopcock valve positioned to connect the syringe directly to the needle's lateral lumen (distal vacuum conduit 86), when the syringe is depressed the fluid will enter the lateral lumen (distal vacuum conduit 86) and then flow into the tissue through the through holes 631 in the wall of the probe tube 630. The cutter tube 40 would be positioned distally (side aperture 34 closed) while the fluid is being inserted into the cavity to prevent the tissue indicator tube 150 from being moved proximally due to the fluid pressure. During subsequent sampling cycles, the fluid would then be aspirated from the tissue cavity.

In FIGS. 39-45, an alternative proximal stacking disposable assembly 702 is depicted that may also be used with the reusable hand piece 12. Pneumatic force is employed to retrieve tissue samples rather than a mechanical movement from the reusable hand piece 12 that actuates a straw assembly. To that end, in FIG. 39, a core biopsy needle ("probe") assembly 704 is formed by a probe tube 706 with a distally positioned side aperture 708. A cutter tube 710 is sized to closely fit and translate within an inner diameter (i.e., cutter lumen) 712 of the probe tube 706 with a length sufficient to close the side aperture 708. The probe assembly 704 includes an underlying vacuum lumen 714 that communicates with the cutter lumen 712 via through holes 716 underlying the side aperture 708. Both the probe tube 706 and vacuum lumen 714 distally terminate in open ends that communicate with each other via a curved manifold 718 defined inside of a piercing tip 720 that is attached as a distal-most portion of the probe assembly 704. A distal tissue stop 722 projects from the piercing tip 720 into the distal open end of the probe tube 706 to maintain prolapsed tissue inside a sampling bowl 724 under the side aperture 708 within the cutter lumen 712. Prolapsing occurs under the urging of axial vacuum force through the cutter lumen 712 and lateral vacuum force through the vacuum lumen 714 converging at the side aperture 708. After distal translation of the rotated cutter tube 712, a tissue sample 726 resides within a distal portion of the cutter tube 712, wherein an inner diameter of the cutter tube 712 defines a tissue sample lumen 728 for guiding retrieval of samples 726. Rather than subsequently distally advancing a straw to encompass and retract the tissue sample 726, axial vacuum pressure as depicted by arrow 730 is asserted against a proximal face of the tissue sample 726 through the tissue sample lumen 728 with the cooperation of lateral pneumatic pressure as depicted by arrow 732 through vacuum lumen 14 and curved manifold 718 to a distal face of the tissue sample 726.

In FIGS. 40-45, the portions of the alternative proximal stacking disposable assembly 702 capture these tissue samples 726. A proximal end of the cutter tube 710 extends through a probe union sleeve 734 to attach to a cutter gear 736. A proximal end of the vacuum lumen 714 terminates within the probe union sleeve 734. The alternative proximal stacking disposable assembly 702 includes a substantially rectangular cover 738 sized to close the access trough recess 18 (FIGS. 2, 4), and omits pneumatic valve features. Instead, the distally positioned probe union sleeve 734 attached to an inner surface 740 of the substantially rectangular cover 738 communicates to a distal hose nib 742 formed on an outer surface 744 of the rectangular cover 738 and to the vacuum lumen 714. A hose 746 is attached to the distal hose nib 742 to selectively provide pneumatic vacuum, pneumatic pressure, or fluid transfer (not shown). The alternate proximal stacking assembly 702 could likewise have a vacuum assist valve assembly 052 as depicted in FIG. 2 to selectively provide pneumatic vacuum, pneumatic pressure, or fluid transfer to the vacuum lumen 714.

Figure 40:
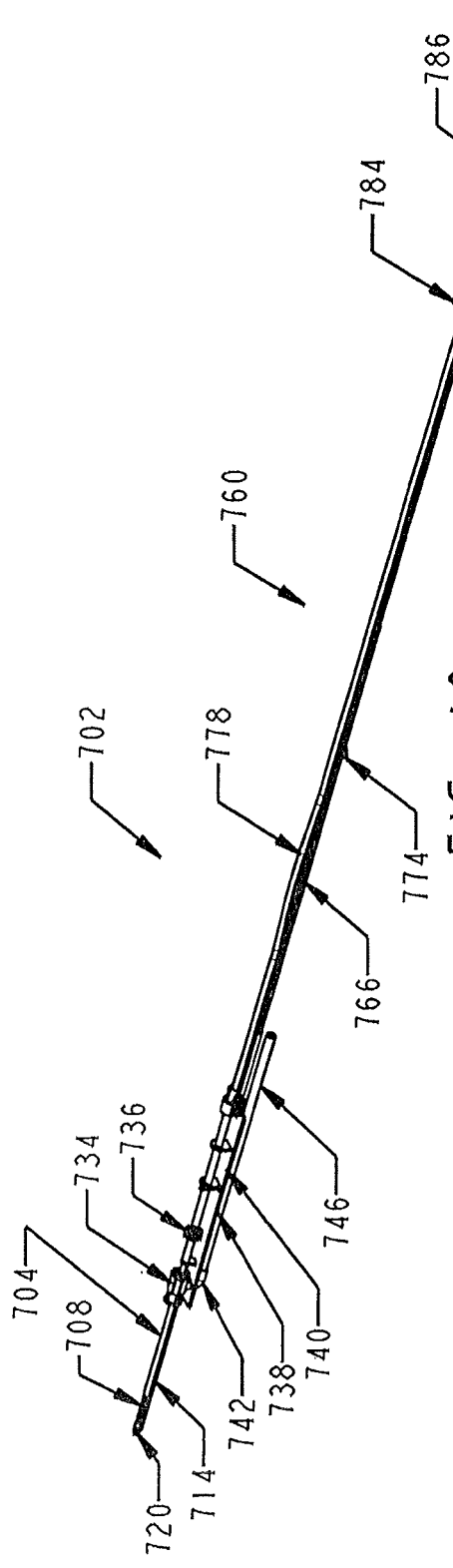
FIG. 40 is a top left perspective view of an alternative proximal stacking disposable assembly incorporating the probe of FIG. 39 and being in an initial state before use.
Figure 42:
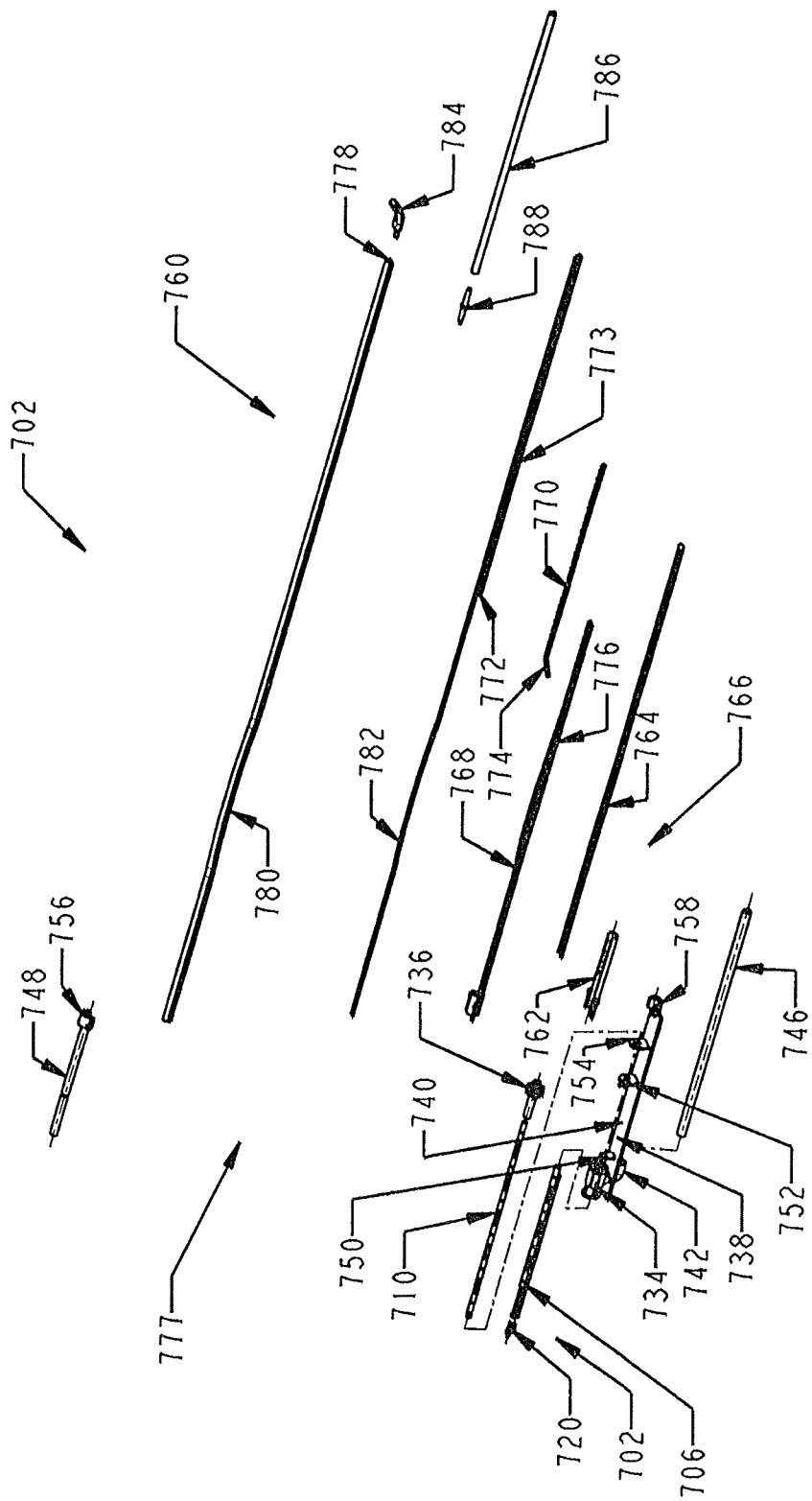
FIG. 42 is a disassembled perspective view of the alternative proximal stacking disposable assembly of FIG. 40.

With particular reference to FIGS. 40, 42, a rear tube 748 is aligned proximally to the cutter tube 710 and coupled for longitudinal movement thereto, although the rear tube 748 is disengaged from the rotational movement of the cutter tube 710. This coupled movement may be achieved by an actuator that engages the distal cutter carriage 250 (FIG. 4) or by a circular lip and groove engagement between the cutter tube 710 and rear tube 748. The inner surface 740 of the rectangular cover 738 includes four support surfaces. First, a cutter guide 750 supports the cutter tube 710 proximal to the probe union sleeve 734 and distal to a most distal position of the cutter gear 736. A distal rear tube guide 752, is proximal to the most proximal position of the cutter gear 736, and a proximal rear tube guide 754, and distal to a most distal position of a proximal locking flange 756 of the rear tube 748, to maintain alignment of the rear tube 748. A bottom half-cylinder locking flange 758 at a proximal end of the rectangular cover 738 cooperates with the proximal locking flange 756 of the rear tube 748 to lock to a sample holding portion 760 of the alternative proximal stacking disposable assembly 702. The sample holding portion 760 extends proximal to the rectangular cover 738 and the reusable hand piece 712 and thus may be readily replaced during a biopsy procedure.

A distal locking half cylindrical portion 762 engages the bottom half-cylinder locking flange 758. The distal locking half cylindrical portion 762 is attached to a proximal half cylindrical portion 764 to form an outer sleeve 766. A reciprocating member 768, which engages the proximal locking flange 756 of the rear tube 748 and is partially encompassed by the outer sleeve 766, engages and distally advances a more proximal rod 770 out of an external vacuum lumen 772 defined as an inner diameter of an external vacuum tube 773. The rod has a down turned distal end 774 that exits an opening 776 in the proximal half cylindrical portion 764. A flexible, peel-apart external tissue tube 777 defining an external tissue lumen 778 is formed from an inwardly open channel 780 closed by an elongate seal 782.

Rod 770 may be formed of a fluoropolymer resin material such as TEFLON™ or other suitable flexible material having a low coefficient of friction. Rod 770 may be sized and shaped to conform closely to the inner diameter (i.e., vacuum lumen 772) of vacuum tube 773. The close fit between rod 770 and vacuum lumen 773, as well as the low friction properties of the rod 770, enable the rod 770 to translate easily within the vacuum lumen 772 without any loss of vacuum force through the distal end of the vacuum lumen 772. The inwardly open channel 780 may advantageously be formed of polyvinyl chloride or another similar type of flexible, water insoluble material so that stacked tissue samples may be visible. A proximal end of the open channel 780 is attached to and closed by a lumen peel tab 784. A proximal end of the external vacuum lumen 772 is attached to a vacuum line 786 via a tubing connector 788.

Figure 41:
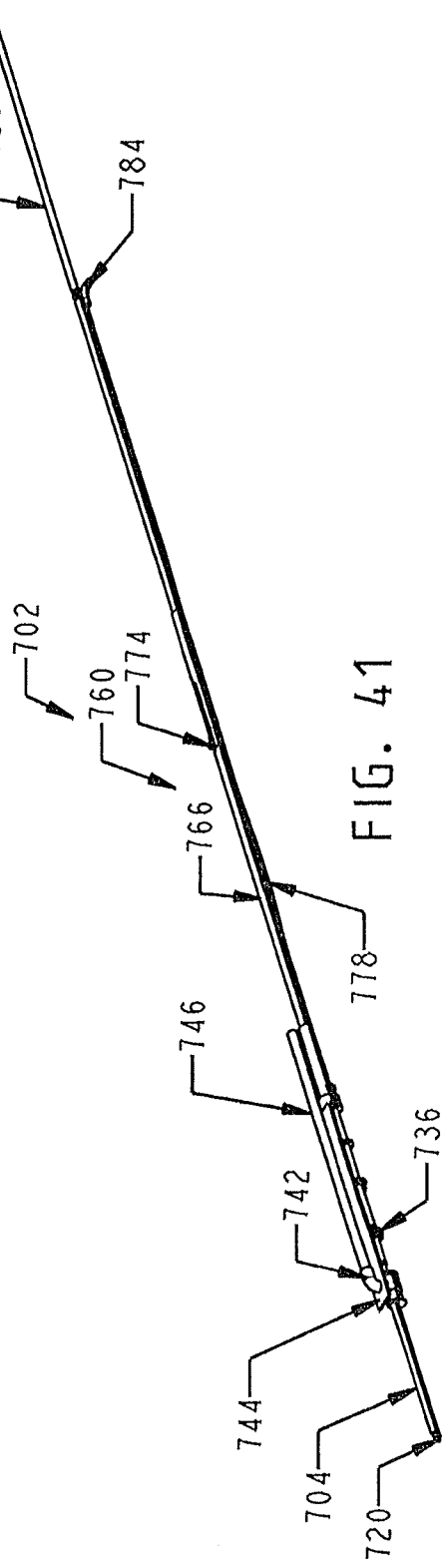
FIG. 41 is a bottom right perspective view of the alternative proximal stacking disposable assembly of FIG. 40.
Figure 45:
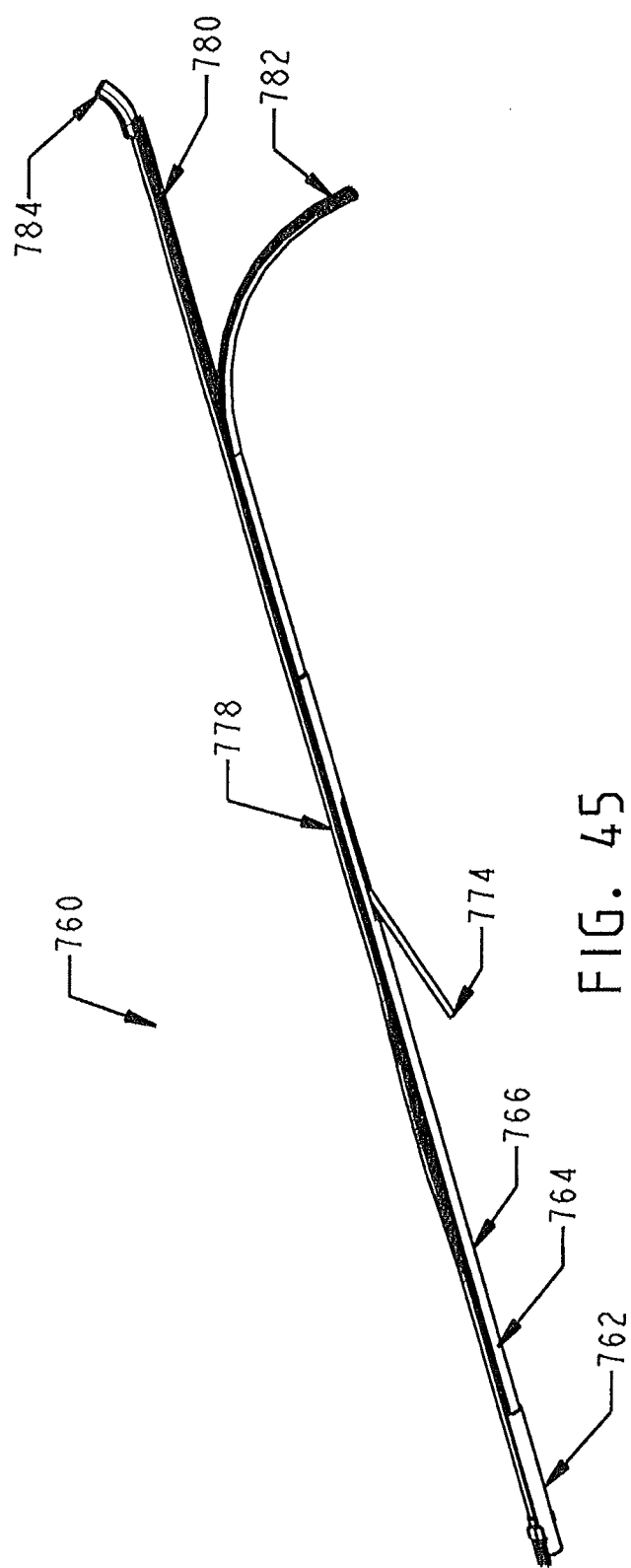
FIG. 45 is a top left perspective view of a flexible, peel-apart external tissue lumen after actuating a lumen peel-apart tab to separate an inwardly open channel holding retrieved tissue samples from an elongate seal.

In FIGS. 40, 41, the alternative proximal stacking disposable assembly 702 is in an initial condition with the rod 770 at its proximal most position in the external vacuum lumen 772. The cutter gear 736 and thus the rear tube 748, reciprocating member 768 and flexible, peel-apart external tissue lumen 778 are in their distal most position. In FIGS. 43, 44, the rod 770 has extruded distally out of the opening 776 in the proximal half cylindrical portion 764 of the outer sleeve 766, denoting reciprocating cycles to retract at least one tissue sample (not shown) that is held within a proximal portion of the external tissue lumen 778. The cutter gear 736 and thus the rear tube 748, reciprocating member 768 and flexible, peel-apart external tissue lumen 778 are in their proximal most positions relative to the outer sleeve 766 and rectangular cover 738. The relative change causes the flexible, peel-apart external tissue lumen 778 to bow away from the outer sleeve 766. In FIG. 45, the lumen peel tab 784 has been pulled to separate the inwardly open channel 780 from the elongate seal 782 to reveal and possibly access stored tissue samples (not shown).

Figure 46:
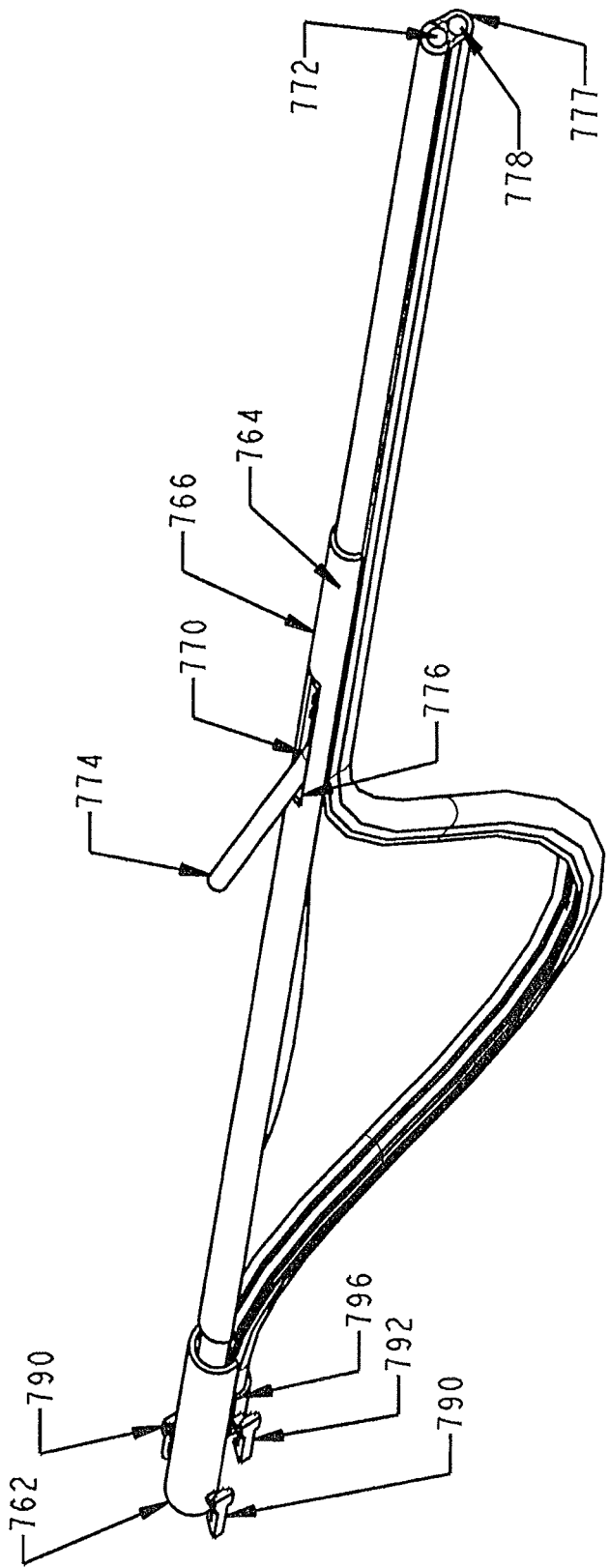
FIG. 46 is a left aft perspective view of the sample holding portion of the alternative proximal stacking disposable assembly of FIG. 40 with a distal portion transversely cut away to expose vacuum and tissue lumens.
Figure 47:
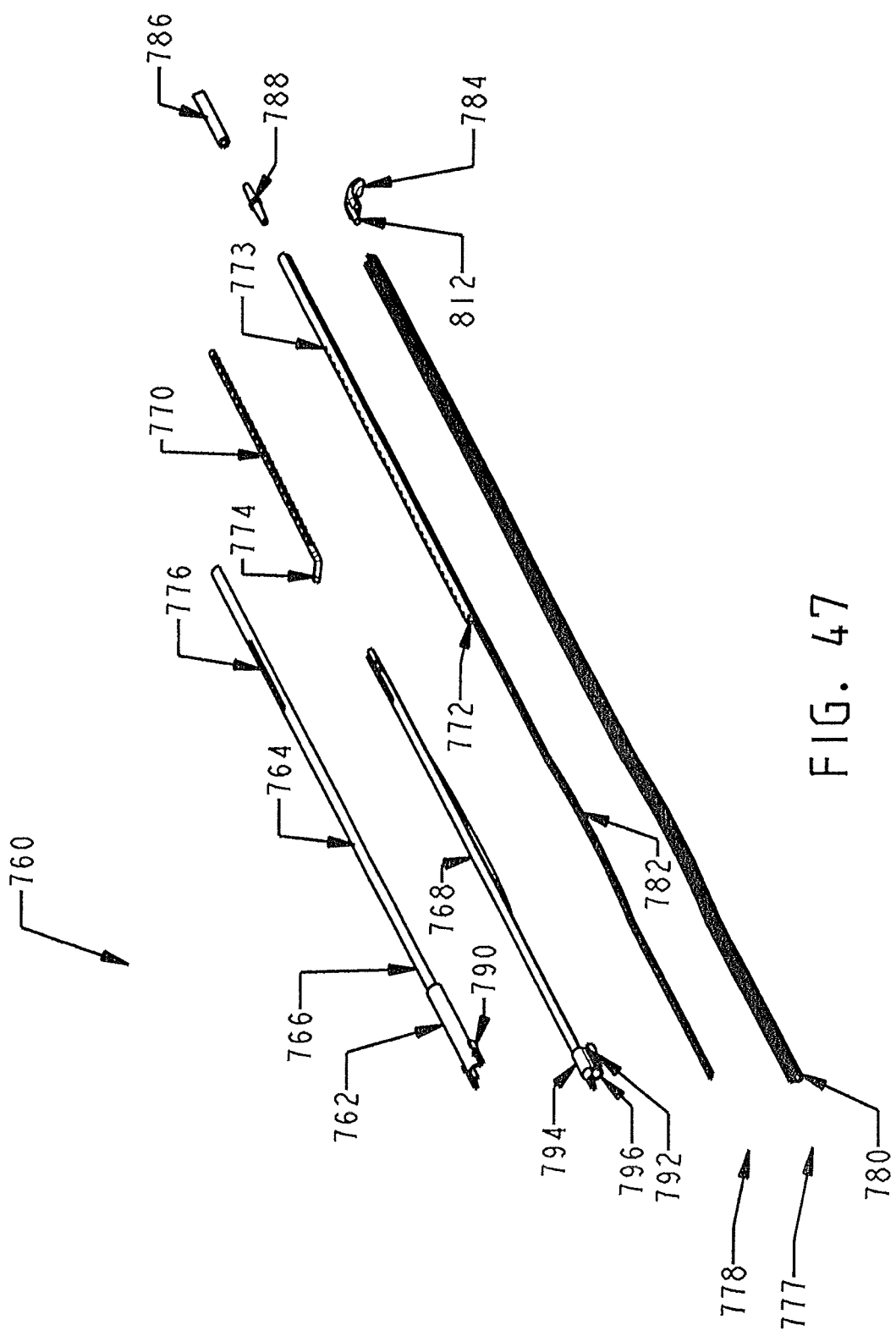
FIG. 47 is a disassembled perspective of the sample holding portion of the alternative proximal stacking disposable assembly of FIG. 40.
Figure 48:
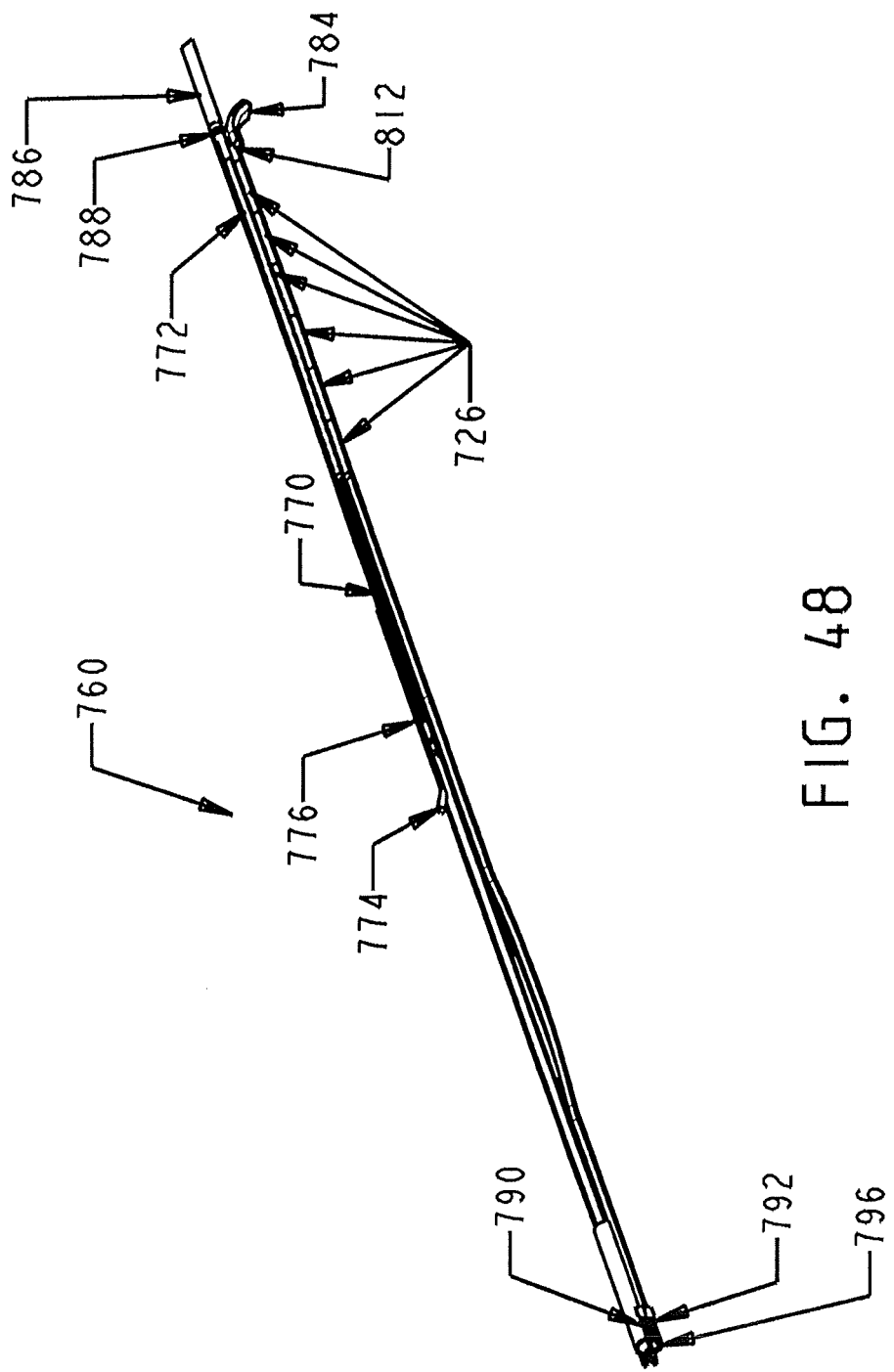
FIG. 48 is a left perspective view of the sample holding portion of the alternative proximal stacking disposable assembly of FIG. 40 formed of a transparent material exposing retrieved tissue samples.

In FIGS. 46-48, the sample holding portion 760 is depicted in greater detail. The distal locking half cylindrical portion 762 of the outer sleeve 766 includes upper lateral locking arms 790 that lock into the bottom half-cylinder locking flange 758 at the proximal end of the rectangular cover 738. In FIGS. 46, 47, aligned below these, lower lateral locking arms 792 of a distal interface portion 794 of the reciprocating member 768 lock into the proximal locking flange 756 of the rear tube 748. The distal interface portion 794 of the reciprocating member 768 includes an axially-extending bore 796 for connecting the external tissue lumen 778 of the sample holding portion 760 to the rear tube 748, maintaining generally coaxial alignment of the probe assembly 702, tissue sample lumen 728, rear tube 748, bore 796, and external tissue lumen 778 to provide an unobstructed passageway for the aspiration of tissue samples from the cutter tube 710.

Figure 49:
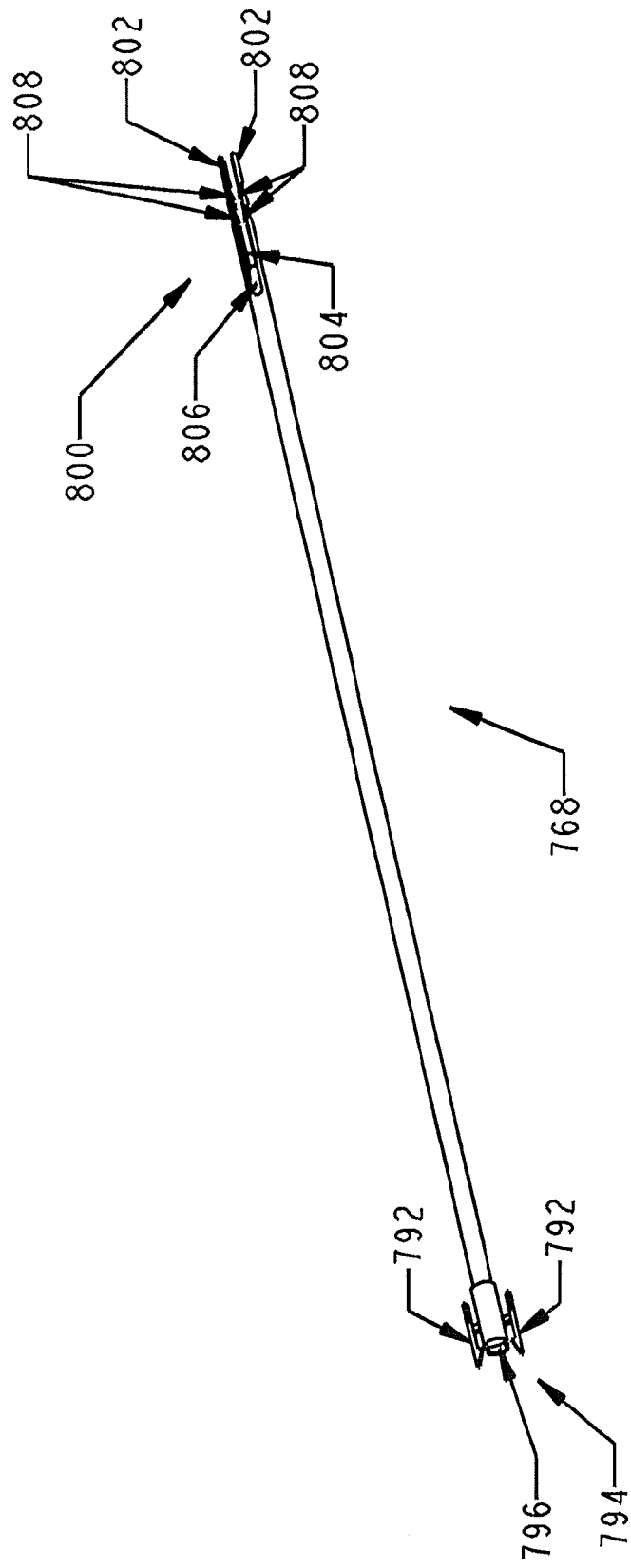
FIG. 49 is a top right perspective view of a reciprocating member of the sample holding portion of the alternative proximal stacking disposable assembly of FIG. 40.
Figure 50:
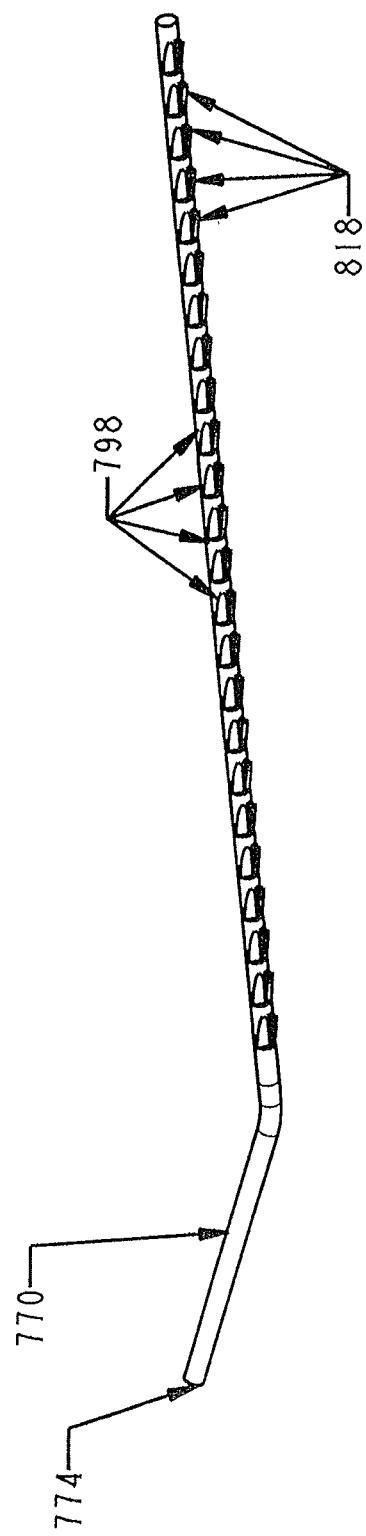
FIG. 50 is a perspective view of a translating flexible rod of the sample holding portion of the alternative proximal stacking disposable assembly of FIG. 40.
Figure 51:
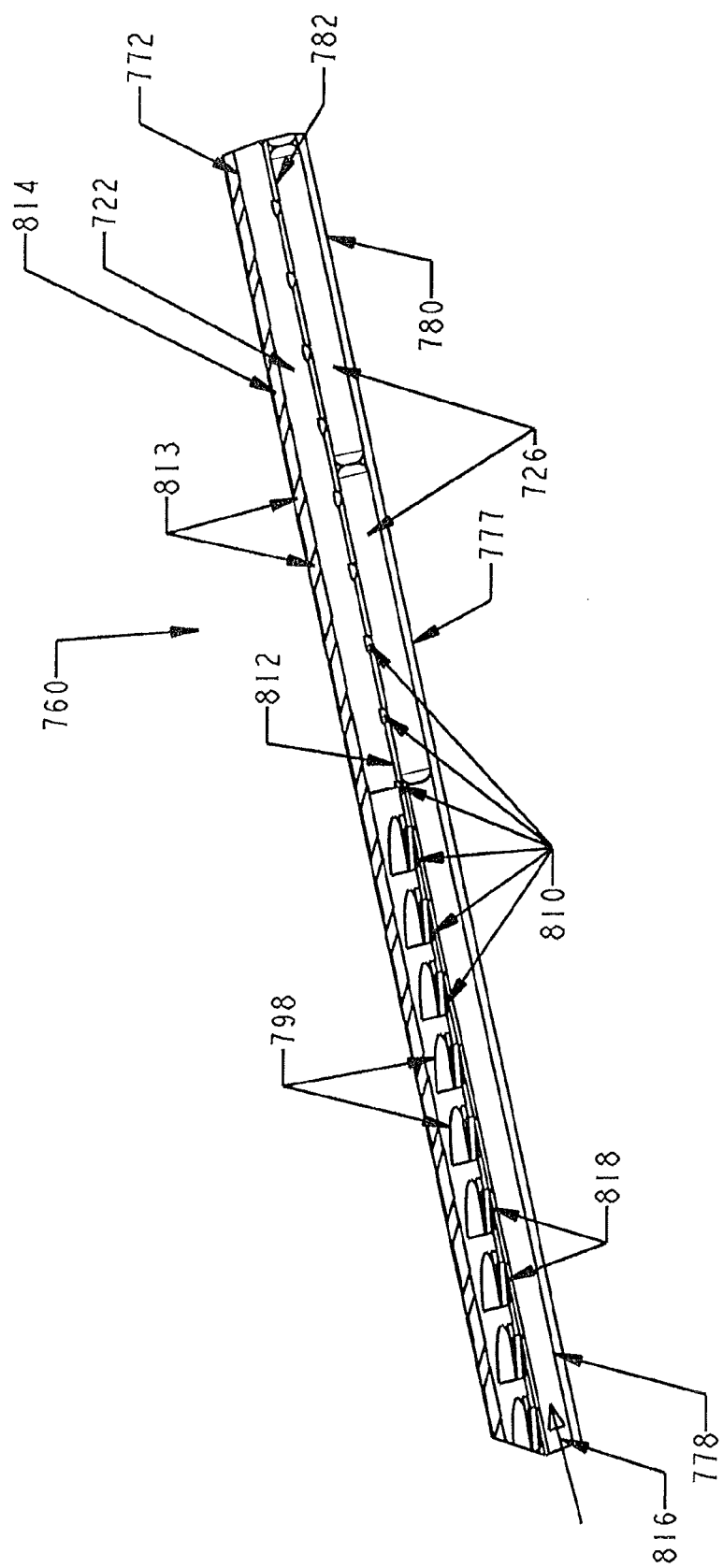
FIG. 51 is a left side view in longitudinal cross section taken through the translating flexible rod of the sample holding portion of the alternative proximal stacking disposable assembly of FIG. 40.

In FIGS. 48, 50-51, the flexible rod 770 may be advanced distally within the external vacuum lumen 772 by the interaction between side ratchet teeth 798 and a pawl-type latching mechanism 800 on the reciprocating member 768, which is shown in greater detail in FIG. 49. Reciprocating member 768 may be supported on lower lateral latch arms 792 and reciprocate as cutter tube 710 is advanced and retracted. Reciprocating member 768 may have a bifurcated proximal end with proximally extending portions 802 separated by an axially extending slot 804. A ramped surface 806 is formed between portions 802 at a distal end of slot 804. Ramped surface 806 may serve to deflect the distal end 774 of rod 770 through the opening 776 in the outer sleeve 766 as the rod 770 is ratcheted out of external vacuum lumen 772. Unidirectional engagement pawls 808 formed to inwardly extend from the proximally extending portions 802 into the axially extending slot 804 engage side ratchet teeth 798 on rod 770 as the rod 770 extends through the axially extending slot 804. The engagement between pawls 808 and side ratchet teeth 798 advances rod 770 distally through vacuum lumen 772.

In FIG. 51, a plurality of small holes 810 may be formed in a center wall divider 812 of the external vacuum tube 773 between external vacuum lumen 772 and tissue lumen 778. Small holes 810 enable vacuum from a source (not shown) connected to vacuum line 786 to communicate from external vacuum lumen 772 into external tissue lumen 778, to provide vacuum in tissue sample lumen 728 in cutter tube 710. Small holes 810 may be spaced along the longitudinal axis of tube vacuum tube 773 and separated by a distance in the range of 0.1 to 4 centimeters. Holes 810 may be oriented at an angle relative to the longitudinal axis of vacuum tube 773. The angle in holes 810 may function as a mechanical diode, in that the edge of the holes 810 opening into the tissue lumen 778 may aid in preventing motion of tissue samples 726 in a distal direction, while permitting tissue samples 726 to move proximally in tissue lumen 778 under vacuum force provided by the vacuum line 786. A tissue sample 726 may continue to slide proximally through the tissue lumen 778 until the sample 726 contacts either a proximal tissue stop 812 attached to the lumen peel tab 784 or a preceding tissue sample 726.

With further reference to FIG. 51, small holes 810 may be formed between lumens 772, 778 by boring top holes 813 into an upper surface 814 of external vacuum tube 773 with the sharpened tip of a drill or other appropriate instrument. The tip of the drill bit or other boring instrument may be directed to pass through vacuum lumen 772 to penetrate the center wall divider 812 that separates the two lumens 772, 778. The proximal half cylindrical portion 764 of the outer sleeve 766 may be securely attached to the upper surface 814 of the external vacuum tube 773 following the drilling of vacuum communication small holes 810 to seal top holes 813. For instance, outer sleeve 766 may be attached to the external vacuum tube 773 by an adhesive or other appropriate type of attachment mechanism.

As tissue samples 726 are stored in tissue lumen 778, the stack of samples 726 will grow in length distally in tissue lumen 778. The samples 726 will tend to block or otherwise restrict flow communication through small holes 810 as the stack of samples 726 extends distally in tissue lumen 778. The translating flexible rod 770 is shown disposed at least partially in vacuum lumen 772. Rod 770 extends axially through vacuum lumen 772 to selectively cover or otherwise block at least some of the small holes 810. Rod 770 may be manipulated, such as by axial movement of rod 770, to selectively expose small holes 810 in the vacuum tube 773 in compensation for those holes 810 blocked by stacked tissue samples 726. For instance, during each cutting cycle, rod 770 may be advanced distally within vacuum lumen 772 to expose or otherwise unblock/open additional small holes 810 as additional samples 726 are stored in tissue lumen 778. The movement of rod 770 maintains a predetermined number of small holes 810 open to provide flow communication between vacuum and tissue lumens 772 and 778 as additional tissue samples 726 are added to the stack of tissue samples 726 in tissue lumen 778, thereby facilitating a generally consistent vacuum force, depicted as arrow 816, in tissue sample lumen 728 in the probe assembly 704 (FIG. 39) throughout multiple cutting cycles.

Figure 52:
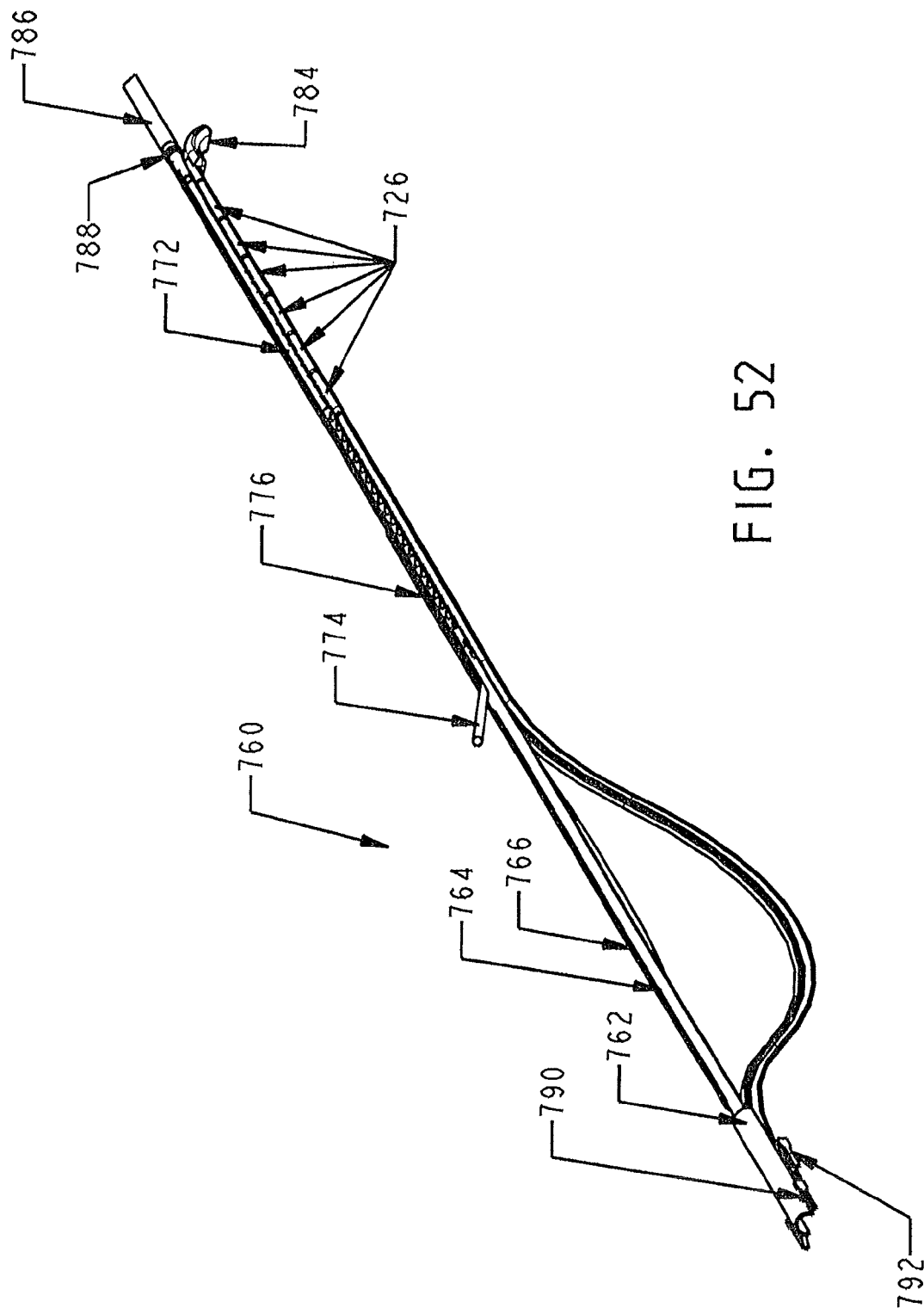
FIG. 52 is a left perspective view of the sample holding portion of the alternative proximal stacking disposable assembly of FIG. 40 with a retracted reciprocating portion.
Figure 53:
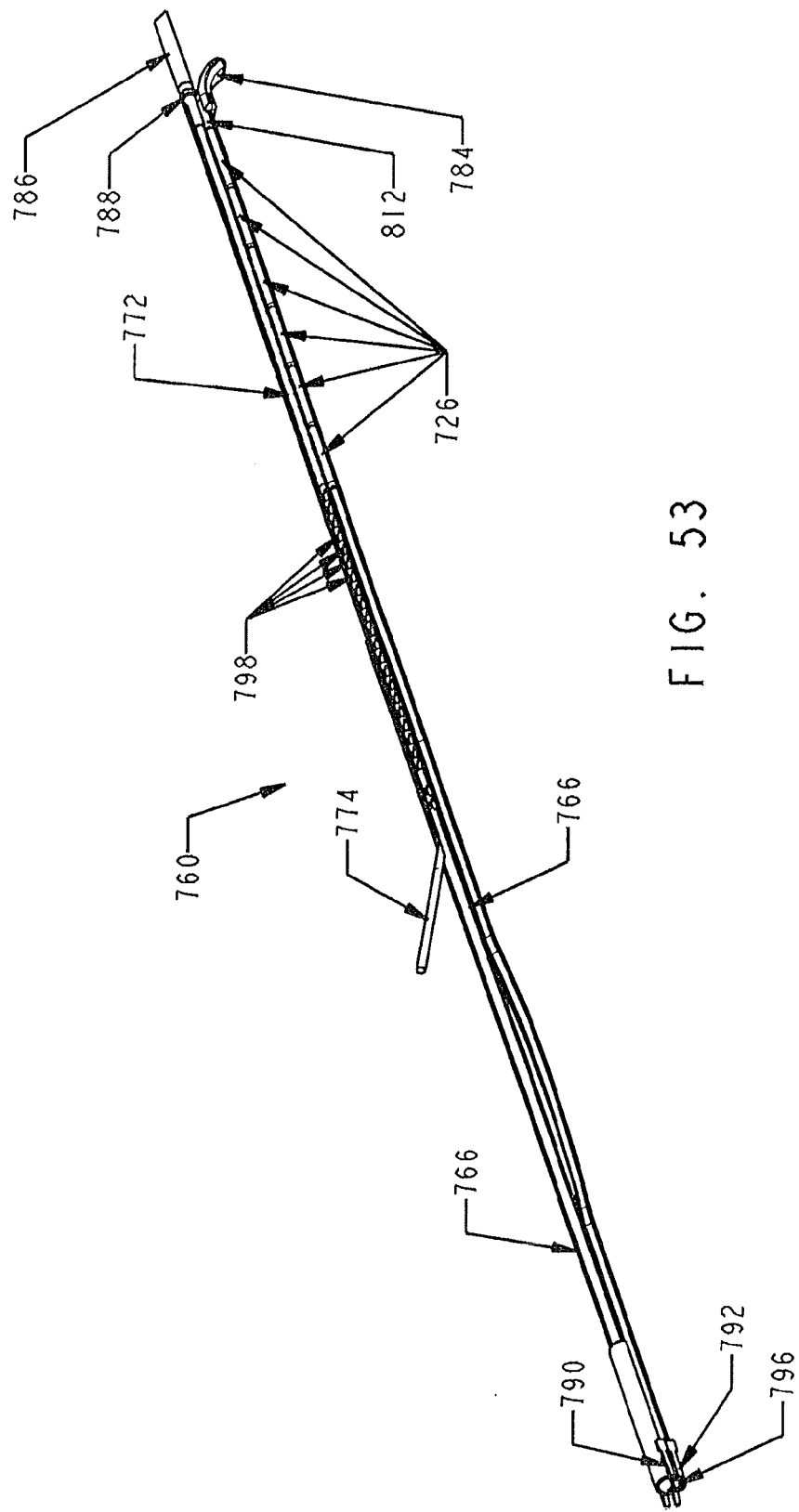
FIG. 53 is a left perspective view of the sample holding portion of the alternative proximal stacking disposable assembly of FIG. 40 with the reciprocating portion subsequently distally advanced.
Figure 54:
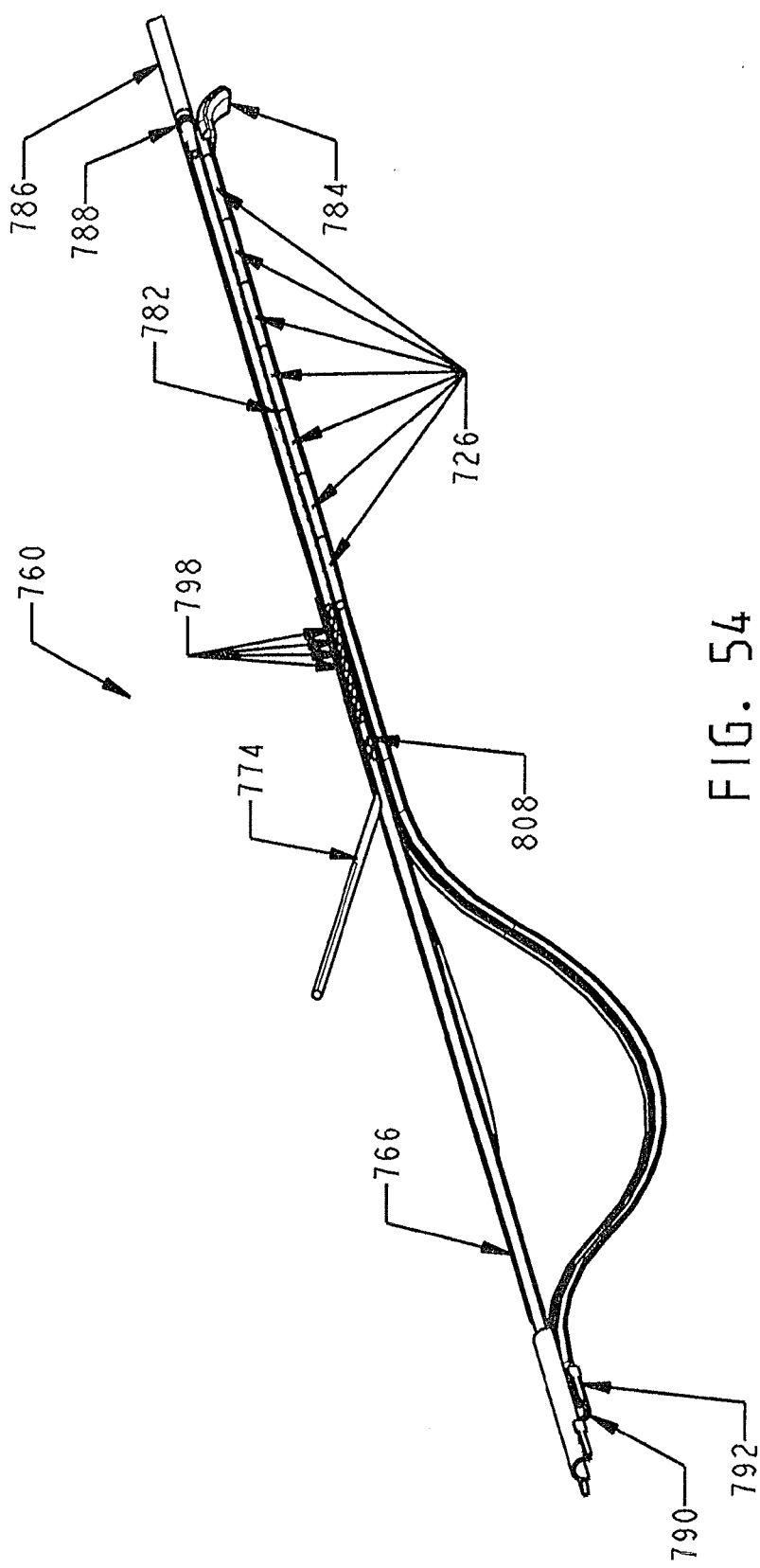
FIG. 54 is a left perspective view of the sample holding portion of the alternative proximal stacking disposable assembly of FIG. 40 with the reciprocating portion subsequently proximally retracted.

Initially as depicted in FIG. 52, flexible rod 770 may be inserted within vacuum lumen 772 such that rod 770 is axially offset within vacuum lumen 772 so as to cover or otherwise block most, but not all, of the small holes 810. For instance, prior to storing any samples 726 in tissue lumen 778, rod 770 may be offset distally within vacuum lumen 772 a distance that is slightly longer than the length of side aperture 708 (FIG. 40). Offsetting rod 770 distally within the vacuum lumen 772 ensures an initial set of small holes 810 are exposed to communicate axial vacuum force 730 to side aperture 708 when cutter tube 710 is in the fully proximal position prior to tissue sampling. The axial vacuum force 730 communicated through the exposed small holes 810 aids in prolapsing tissue into side aperture 708 prior to cutting, as well as pulling the tissue sample 726 proximally into tissue lumen 778 after cutting. As a tissue sample 726 is drawn into and stacked within tissue lumen 778, the tissue sample 726 blocks the previously exposed small holes 810, preventing vacuum from passing into the tissue lumen 778. Rod 770 may be selectively moved a predetermined distance distally that is slightly longer than the length of side aperture 708 to expose additional small holes 810 immediately distal of the most recently acquired tissue sample 726. Rod 770 may be adapted to be automatically advanced distally by the translation of the cutter carriage 250. The newly exposed small holes 810 continue the communication of vacuum force 816 into tissue lumen 778 for the next cutting cycle. As reciprocating member 768 retracts proximally, unidirectional bottom ratchet teeth 818 located on the bottom side of flexible rod 770 engage the small holes 810 within vacuum lumen 772. The engagement between the bottom ratchet teeth 818 and small holes 810 prevents rod 770 from moving proximally within vacuum lumen 772. As pawls 808 move proximally relative to rod 770, the pawls 808 engage the next proximal set of side ratchet teeth 798 on rod 770. This engagement with the next set of side ratchet teeth 798 causes rod 770 to again advance distally when the reciprocating member 768 advances distally during the next cutting cycle to expose additional small holes 810. In the event that the cutter tube 710, and thus the reciprocating member 768, is advanced and retracted without the probe assembly 704 in tissue, the result is that the flexible rod 770 advances too far distally relative to the tissue samples 726; the flexible rod 770 may be rotated a fraction of a turn about its longitudinal axis to disengage side ratchet teeth 798 and pawls 808 allowing the flexible rod 770 to be repositioned proximally within the vacuum lumen 772.

A similar sample holding portion is described in five commonly-owned and co-pending U.S. patent application Ser. No. 10/953,834, "Biopsy Apparatus and Method" END-5469; Ser. No. 10/953,904 "Improved Biopsy Apparatus and Method" END 5470; Ser. No. 10/953,397 "Fluid Control for Biopsy Device" END 5471; Ser. No. 10/953,395 "Biopsy Device with Sample Storage" END 5472; and Ser. No. 10/953,389 "Cutter for Biopsy Device" END 5473, all to Hibner et al. and filed on 29 Sep. 2004, the disclosures of which are hereby incorporated by reference in their entirety.

While preferred embodiments of the present invention have been shown and described herein, it will be obvious to those skilled in the art that such embodiments are provided by way of example only. Numerous variations, changes, and substitutions will now occur to those skilled in the art without departing from the spirit and scope of the appended claims. Additionally, each element described in relation to the invention may be alternatively described as a means for performing that element's function.

For example, one or more sensors may be incorporated into the hand piece 12 to sense the actual position of each carriage or to sense the particular disposable probe assembly assembled into the hand piece 12.

We claim:

1. A biopsy device, comprising:
   (a) a body;
   (b) a needle extending distally from the body, wherein the needle comprises a lumen;
   (c) a cutter, wherein the cutter is movable relative to the needle to sever tissue adjacent to the needle; and
   (d) a valve assembly in fluid communication with the needle, the valve assembly comprising:
      (i) a translating member, and
      (ii) a valve body, wherein the translating member is movable relative to the valve body to change a pneumatic state of the lumen based at least in part on the position of the cutter relative to the needle.

2. The biopsy device of claim 1, wherein the needle comprises a closed tip.

3. The biopsy device of claim 2, wherein the needle comprises a transverse tissue receiving aperture proximal to the closed tip.

4. The biopsy device of claim 3, wherein the lumen is in communication with the transverse tissue receiving aperture.

5. The biopsy device of claim 1, wherein the lumen comprises a first lumen, wherein the cutter is disposed in the first lumen.

6. The biopsy device of claim 5, wherein the needle comprises a second lumen adjacent to the cutter.

7. The biopsy device of claim 6, wherein the needle further comprises a wall separating at least part of the first lumen from at least part of the second lumen, wherein the wall comprises a plurality of openings providing fluid communication between the first lumen and the second lumen.

8. The biopsy device of claim 6, wherein the valve assembly is in fluid communication with the second lumen.

9. The biopsy device of claim 8, wherein the valve body defines a bore, wherein the translating member is slidably disposed in the bore of the valve body.

10. The biopsy device of claim 9, wherein the valve body further comprises a first port and a second port, wherein the first port is in fluid communication with the second lumen, wherein the second port is in fluid communication with atmospheric air.

11. The biopsy device of claim 10, wherein the translating member is translatable within the valve bore to selectively couple the first port and the second port, based at least in part on the position of the cutter in the first lumen.

12. The biopsy device of claim 10, wherein the valve body further includes a third port, wherein the third port is in fluid communication with a vacuum source.

13. The biopsy device of claim 12, wherein the translating member is translatable within the valve bore to selectively couple the first port with either the second port or the third port, based at least in part on the position of the cutter in the first lumen.

14. The biopsy device of claim 1, wherein the cutter defines a first axis, wherein the translating member defines a second axis, wherein the first axis and the second axis are parallel to each other.

15. The biopsy device of claim 1, wherein the body comprises a disposable probe portion and a reusable hand piece, wherein the probe portion is selectively engageable with the hand piece.

16. The biopsy device of claim 15, wherein the needle extends distally from the probe portion, wherein the valve assembly is part of the probe portion.

17. The biopsy device of claim 1, further comprising a carriage coupled with the translating member, wherein the carriage is operable to translate the translating member, wherein the biopsy device further comprises an elongate straw slidingly received in the cutter, wherein the straw is configured to receive tissue samples severed by the cutter.

18. A biopsy device, comprising:
(a) a body;
(b) a needle extending distally from the body;
(c) a cutter, wherein the cutter is movable relative to the needle to sever tissue adjacent to the needle; and
(d) a valve assembly in fluid communication with the needle, the valve assembly comprising:
(i) a translating member, and
(ii) a valve body, wherein the translating member is movable relative to the valve body to change a pneumatic state of the needle based at least in part on the position of the cutter relative to the needle.

19. The biopsy device of claim 18, wherein the needle includes a first lumen and a second lumen, wherein the second lumen is adjacent to the first lumen, wherein the cutter is disposed in the first lumen, wherein the valve body is in fluid communication with the second lumen.

20. A biopsy device, comprising:
(a) a body;
(b) a needle extending distally from the body;
(c) a cutter movable relative to the needle to sever tissue adjacent to the needle; and
(d) a valve assembly in fluid communication with the needle, the valve assembly comprising:
(i) a translating member, and
(ii) a valve body defining a bore and having a first port and a second port in fluid communication with the bore, wherein the first port is further in fluid communication with the needle, wherein the second port is further in fluid communication with atmospheric air, wherein the translating member is movable within the bore of the valve body to selectively couple the first port with the second port based on the longitudinal position of the translating member in the bore.

* * * * *